US010038150B2

(12) United States Patent
Burschka et al.

(10) Patent No.: US 10,038,150 B2
(45) Date of Patent: Jul. 31, 2018

(54) METAL COMPLEXES FOR USE AS DOPANTS AND OTHER USES

(71) Applicant: Ecole Polytechnique Federale de Lausanne (EPFL), Lausanne (CH)

(72) Inventors: Julian Burschka, Darmstadt (DE); Florian Kessler, Hochstadt an der Aisch (DE); Etienne Baranoff, Birmingham (GB); Mohammad Khaja Nazeeruddin, Ecublens (CH); Michael Graetzel, St-Sulpice (CH); Shaik Mohammed Zakeeruddin, Bussigny-Lausanne (CH); Anders Hagfeldt, Lully (CH); Marina Freitag, St-Sulpice (CH); Fabrizio Giordano, St-Sulpice (CH)

(73) Assignee: Ecole Polytechnique Federale de Lausanne (EPFL), Lausanne (CH)

(*) Notice: Subject to any disclaimer, the term of this patent is extended or adjusted under 35 U.S.C. 154(b) by 0 days.

(21) Appl. No.: 15/099,089

(22) Filed: Apr. 14, 2016

(65) Prior Publication Data

US 2016/0233439 A1 Aug. 11, 2016

Related U.S. Application Data

(63) Continuation-in-part of application No. 14/001,307, filed as application No. PCT/IB2012/050870 on Feb. 24, 2012.

(30) Foreign Application Priority Data

Feb. 25, 2011 (EP) .................................. 11156029
Apr. 8, 2011 (EP) .................................. 11161739
(Continued)

(51) Int. Cl.
*H01M 2/16* (2006.01)
*H01L 51/00* (2006.01)
(Continued)

(52) U.S. Cl.
CPC ........ *H01L 51/0083* (2013.01); *C07F 15/065* (2013.01); *H01L 51/002* (2013.01); *H01L 51/4226* (2013.01); *Y02E 10/549* (2013.01)

(58) Field of Classification Search
CPC .. C07F 9/587; C07F 15/06; C09K 2211/1029; C09K 2211/1044; C09K 2211/187
See application file for complete search history.

(56) References Cited

U.S. PATENT DOCUMENTS 6,951,398 B2 * 10/2005 Borra .................... G02B 26/005
264/1.9
2005/0061232 A1 3/2005 Werner et al.
(Continued)

FOREIGN PATENT DOCUMENTS

EP 1160888 A1 12/2001
EP 1095387 B1 3/2004
(Continued)

OTHER PUBLICATIONS

Cho et al. (Macromol. Rapid Commun. 2004, 25, 302-306).*
(Continued)

*Primary Examiner* — Shane Fang
(74) *Attorney, Agent, or Firm* — Taft Stettinius & Hollister LLP

(57) ABSTRACT

The invention relates to electrochemical devices comprising complexes of cobalt comprising at least one ligand with a 5- or six membered, N-containing heteroring. The complex are useful as p- and n-dopants, as over of electrochemical devices, in particular in organic semiconductors. The com-
(Continued)

plexes are further useful as over-discharge prevention and overvoltage protection agents.

19 Claims, 17 Drawing Sheets

(30) Foreign Application Priority Data

Apr. 11, 2011 (EP) .................................. 11161954
Jul. 28, 2011 (EP) .................................. 11175732

(51) Int. Cl.
*C07F 15/06* (2006.01)
*H01L 51/42* (2006.01)

(56) References Cited

U.S. PATENT DOCUMENTS

| | | |
|---|---|---|
| 2006/0250076 A1 | 11/2006 | Hofmann et al. |
| 2010/0140566 A1 | 6/2010 | Zeika et al. |
| 2012/0323007 A1 | 12/2012 | Huang et al. |
| 2014/0060641 A1* | 3/2014 | Nazeeruddin ........ C07D 401/14 136/256 |

FOREIGN PATENT DOCUMENTS

| | | |
|---|---|---|
| WO | 2004097871 A2 | 11/2004 |
| WO | 2005036667 A1 | 4/2005 |
| WO | 2005086251 A2 | 9/2005 |
| WO | 2006010290 A1 | 2/2006 |
| WO | 2010089394 A1 | 8/2010 |
| WO | 2014020499 A1 | 2/2014 |

OTHER PUBLICATIONS

Bai et al. (Chem. Commun., 2011, 47, 4376-4378).*
Hattori et al., J. Am. Chem. Soc. 9 vol. 127, No. 26, 2005 9651.*
International Search Report, European Patent Office, International Application No. PCT/IB2012/050870, Jul. 26, 2012, 5 pages.
Written Opinion of the International Searching Authority; European Patent Office; International Application No. PCT/IB2012/050870; dated Jul. 26, 2012; 6 pages.
Herve Nusbaumer et al.; An Alternative Efficient Redox Couple for the Dye-Sensitized Solar Cell System; Chemistry—A European Journal; 2003; pp. 2756-3763; vol. 9, No. 16; Wiley-VCH Verlag GmbH & Co.
Ronald R. Ruminski et al.; Tris(2,2'-bipyrimidine)cobalt(III, II, I). A Cobalt Polyazine Electrochemical System with Large Storage Capabilities; Inorganica Chimica Acta; 1984; pp. 63-66; vol. 86, No. 1; Elsevier, Switzerland.
Hyo Joong Lee et al.; Regenerative PbS and CdS Quantum Dot Sensitized Solar Cells with a Cobalt Complex as Hole Mediator; Langmuir; 2009; pp. 7602-7606; vol. 25, No. 13.
Petra J. Cameron et al.; Electrochemical Studies of the Co(II-I)Co(II)(dbbip)2 Redox Couple as a Mediator for Dye-Sensitized Nanocrystalline Solar Cells; Coordination Chemistry Reviews; 2001; pp. 1447-1453; vol. 248, No. 13; Elsevier.
C.S. Cha et al.; Polypyridine Complexes of Iron Used as Redox Shuttles for Overcharge Protection of Secondary Lithium Batteries; Journal of Power Sources; 1995; pp. 255-258; vol. 54, No. 2; Elsevier.
Cho et al.; Macromol. Rapid Commun.; 2004; 25; 302-306.

* cited by examiner

H-29    H-30    H-31

M-13    M-14    M-15

N-1    N-2    N-3

N-4    N-5    N-6

N-7    N-8

N-9    N-10    N-11

N-12    N-13    N-14

METAL COMPLEXES FOR USE AS DOPANTS AND OTHER USES

CROSS-REFERENCE TO RELATED APPLICATIONS

This application is a continuation-in-part of U.S. patent application Ser. No. 14/001,307 filed Aug. 23, 2013, which is a U.S. National Phase filing of International PCT Patent Application No. PCT/IB2012/050870 filed Feb. 24, 2012, which claims foreign priority to European Patent Application No. 11156029.8 filed Feb. 25, 2011, European Patent Application No. 11161739.5 filed Apr. 8, 2011, European Patent Application No. 11161954.0 filed Apr. 11, 2011 and European Patent Application No. 11175732.4 filed Jul. 28, 2011. Each of these prior applications is incorporated herein by reference in its entirety.

TECHNICAL FIELD

The present invention relates to novel complexes of transition metals, electrochemical devices comprising the complexes and uses of the complexes in particular in electrochemical devices. The invention further relates to methods of preparing electrochemical devices, and further methods. The present invention relates, in particular, to copper (II) metal organic complexes, dopants comprising one or more copper metal organic complexes, their use as dopant for hole transporting materials and/or for organic hole transport layers, optoelectronic and/or electrochemical devices, in particular solar cells and solid state solar cells comprising said compounds, and a method of synthesis of said metal organic compounds.

BACKGROUND ART AND PROBLEMS SOLVED BY THE INVENTION

Chemical doping is an important strategy to alter the charge transport properties of both molecular and polymeric organic semiconductors, and finds application in organic electronic devices, for instance in organic light-emitting devices (OLEDs). Various materials have been reported for their use as p-dopants, for example, ranging from strongly electron-accepting organic molecules such as 2,3,5,6-tetrafluoro-7,7,8,8-tetracyano-quinodimethane (F4-TCNQ) to transition metal oxides such as $WO_3$ (Meyer, J. et al., *Mater. Chem.* 2009, 19, 702), metal organic complexes such as molybdenum tris-[1,2-bis(trifluoromethyl)ethane-1,2-dithiolene] (Qi, Y. et al., *J. Am. Chem. Soc.* 2009, 131, 12530-12531) and redox active salts such as $NOBF_4$ (Snaith, H. J. et al., *Appl. Phys. Lett.* 2006, 89, 262114) or $(p-BrC_6H_4)_3NSbCl_6$ (Bach, U. et al., *Nature* 1998, 395, 583-585. Many of these materials are usually applied by vacuum deposition techniques and exhibit low solubility in organic solvent, others are facing stability issues or are reactive and prone to side reactions.

It is thus an objective of the present invention to provide a new class of dopants that allows to easily tune the chemical, physical, optical and/or electronic properties of the doping agent in order to carefully adapt it to the desired application. For example, for OLEDs, doping of interfaces might be preferable, which is easier if the dopant is deposited by thermal evaporation. Dopants based on metal complex having negatively charged ligands, for example, may be used to obtain neutral complexes that can be deposited by thermal evaporation. Doping at interfaces by evaporation could be used for OLEDs, organic solar cells and also the solid state dye-sensitized solar cells (ssDCSs).

Furthermore, it is an objective to provide dopants the solubility of which can be adjusted. For example, it is an objective to provide dopants that are easily soluble in organic solvents, that are stable and that do not engage in undesired side reactions in the device. Besides the solubility, the dopants are ideally charged or neutral to use by thermal evaporation in organic light emitting diodes, and solar cells.

Organic hole transporting materials (HTMs) are useful in a wide range of optoelelectronic and/or electrochemical devices and applications, such as in organic electroluminescent (EL) devices, organic light-emitting devices (OLEDs) and in photovoltaic devices, solar cells, dye-sensitized solar cells and solid state solar cells.

In organic light emitting diodes (OLED), one problem of dopants is their diffusion across the different layers of the OLED, leading to a reduction in performance or even loss of function. It would thus be advantageous to provide dopants the diffusion of which can be controlled, for example by using suitable counter ions.

Perovskite-based and other types of solid state solar cells generally contain an organic hole transporting material (HTM) layer, for transporting holes created by charge separation at the light harvester to the counter electrode and/or cathode for filling up by incoming electrons, thereby closing the electric circuit and rendering the devices regenerative. Currently most performing solid state device use doped Spiro-OMeTAD (2,2',7,7'-tetrakis(N,N-di-p-methoxyphenyl amine)-9,9-spirobifluorene) as a HTM.

Dopants are also used in solid state (ss) dye-sensitized solar cell (DSC) applications, in which the liquid electrolyte is replaced by a solid hole transporting material (HTM). In particular when using 2,2',7,7'-tetrakis(N,N-di-p-methoxy-phenyl-amine)-9,9'-spirobifluorene (spiro-MeOTAD) as HTM, high power conversion efficiencies have been yielded. Bach et al. (1998) were the first to report on the use of spiro-MeOTAD in ssDSCs and although research interest to identify competitive alternatives is strong, spiro-MeOTAD is still the system of choice when high efficiencies are demanded. Several intrinsic properties like its glass transition temperature, solubility, ionization potential, absorption spectrum and solid-state morphology make Spiro-MeOTAD a suitable candidate for DSC applications. However, similar to other organic hole conductors including liquid hole conductors, spiro-MeOTAD suffers from a relatively low conductivity in its pristine form. It is an objective to provide dopants that can also be used in liquid organic charge transporting materials.

The high efficiency obtained with hybrid solar cells based on perovskite sensitizers demonstrates their potential for implementation as commercial solar cells. However, the use of organic hole conductors may represent a potential hurdle to the future commercialization of this type of solar cell because of their relatively high cost. While the increased demand would undoubtedly lower the costs in any large-scale commercial endeavor, it is likely to remain expensive due to the synthetic methods and high purity needed for photovoltaic applications. Thus, there is a need to provide further means to improve the conductivity of HTM that allow a more economical preparation of electrochemical devices such as solar cells and solid state solar cells. The development of alternative dopants for HTM is a promising avenue to further improve the performance of solar cells.

High power conversion efficiencies can still be achieved without adding dopant in the HTM layer due to photo-doping (reaction of spiro-MeOTAD with molecular oxygen under illumination). Although it is often believed that chemical p-doping is not necessary to obtain high device performance, photo-doping is clearly a process that is not easy to control.

Further, many of these dopants are usually applied by vacuum deposition techniques and exhibit low solubility in organic solvent, whereas other dopants face stability issues or are reactive and prone to side reactions.

From the above, it is an objective to provide new dopant for HTM, which overcome deficiencies of HTM. There is a need for novel doping materials or new classes of dopants, which can be produced at lower costs and which shall have a low toxicity impact on the environment as being nontoxic. There is also a need for new classes of dopants, that allow easily tuning the chemical, physical, optical and/or electronic properties of the doping agent in order to carefully adapt it to the desired application. It is a further objective to provide new dopants for increasing the conductivity of organic HTM by other and/or additional ways than by photo-doping, in particular for increasing the conductivity of organic charge transporting material in a highly reproducible way in order to fabricate stable electrochemical devices using organic charge transporting materials. Furthermore, dopants with an adjustable solubility, in particular in organic solvents, stable and not promoting any undesired side reactions in the device are also highly demanding.

It is an objective of the invention to provide means for increasing conductivity of charge transporting materials, in particular of hole and/or electron transporting materials, such as, for example, organic conductors or semiconductors.

It is also an objective of the invention to provide a means to improve charge collection and/or charge transfer, for example at the interface, in particular in case dopants are applied by evaporating the dopant.

With respect to solid state dye-sensitized solar cells (ssDSCs) it is noted that Bach et al (1998) already employed (p-BrC$_6$H$_4$)$_3$NSbCl$_6$ as a chemical p-dopant but up to the present date, no detailed study on p-type doping in dye solar cells has been reported. Surprisingly, the use of chemically p-doped spiro-MeOTAD has gradually diminished and most of the recent publications on spiro-MeOTAD-based ssDSCs do not follow this strategy. The reason, why high power conversion efficiencies can still be achieved, is the device fabrication under atmospheric conditions and a facile reaction of spiro-MeOTAD with molecular oxygen under illumination, a process referred to as photo-doping. Therefore, it is currently believed that chemical p-doping is not necessarily the key to high performance. On the other hand, photo-doping is clearly a process that is not easy to control. Therefore, it is an objective of the present invention to provide means of increasing conductivity of organic charge transporting materials by other and/or additional ways than by photo doping. It is in particular an objective to increasing conductivity of organic charge transporting material in a highly reproducible way and to fabricate stable electrochemical devices using organic charge transporting materials.

With respect to rechargeable batteries, such batteries are used in many electronic devices, in particular portable devices, such as cell phones, laptops, tablet computers (iPad, etc), portable computer game consoles and so forth, for example. Rechargeable batteries, in particular lithium-ion batteries, may experience thermal runaway resulting in overheating. Sealed cells will sometimes explode violently. Lithium-ion batteries can rupture, ignite or explode when exposed to high temperature. For example, short-circuiting may cause the cell to overheat and possibly catch fire. It is an objective of the invention to provide ways for preventing or reducing the risk of explosion and/or the risk of overdischarging.

It is also an objective of the invention to provide agents that can be used for protecting electronic devices, in particular electrochemical devices against overvoltage.

The present invention addresses the problems and objectives depicted above, which are part of the present invention.

SUMMARY OF THE INVENTION

The present inventors provide complexes of transition metal complexes, in particular of cobalt, that have several useful properties when used in electrochemical devices. In particular, the complexes are useful as dopants in electronic hole and/or electron transport layers. It has surprisingly been found that the complexes of the invention are suitable to increase the conductivity and charge carrier mobility of organic charge transporting materials. The conductivity of these materials (organic HTM) is increased by the use of these complexes in order to improve the device performance by other or additional ways than photo-doping and in a highly reproducible way.

Further these novel doping complexes or new classes of dopants can be produced at lower costs. Such doping complexes have an adjustable solubility, in particular in organic solvents, stable and do not promote any undesired side reactions in the device are also highly demanding In an aspect, the invention provides a dopant comprising a complex of formula (XX)

wherein
  M is selected from Cu$^{2+}$, Pd$^{2+}$, Au$^{2+}$, Ag$^{2+}$, and V$^{2+}$;
  n is an integer selected from 1, 2, 3 or 4;
  m is an integer selected from 0, 1, 2, or 3;
  La is a ligand independently selected from mono-, bi-, or tridentate ligands comprising a moiety independently selected from a moiety according to any one of formulae (XX-1) to (XX-69)

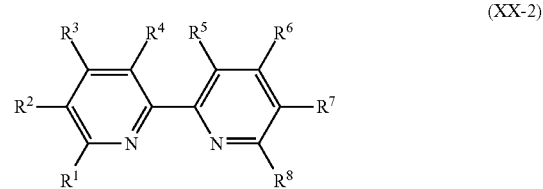

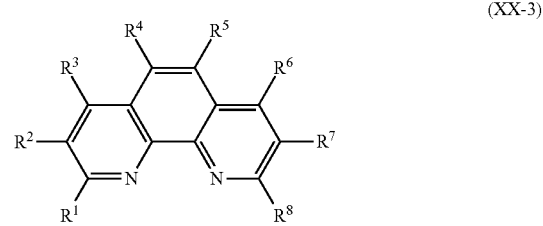

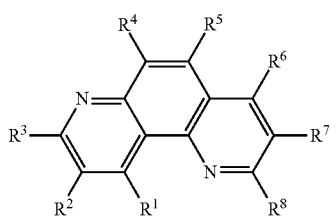
(XX-4)
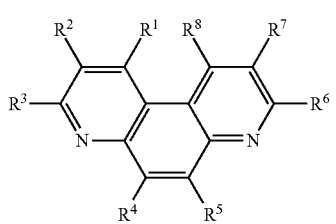
(XX-5)
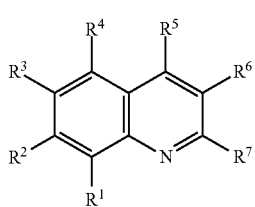
(XX-6)
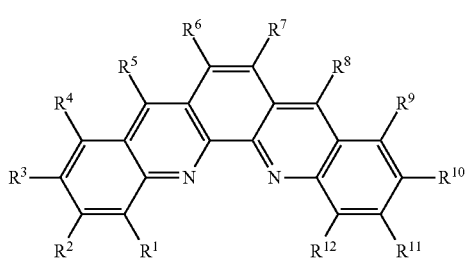
(XX-7)
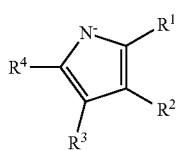
(XX-8)
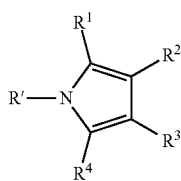
(XX-9)
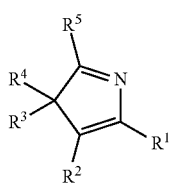
(XX-10)
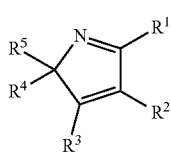
(XX-11)
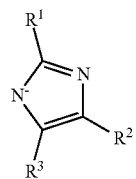
(XX-12)
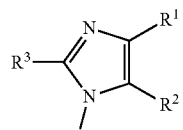
(XX-13)
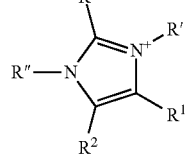
(XX-14)
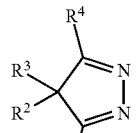
(XX-15)
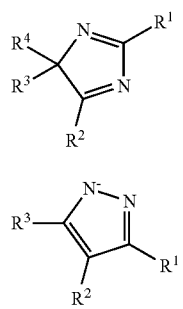
(XX-16)
(XX-17)
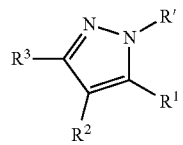
(XX-18)
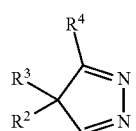
(XX-19)
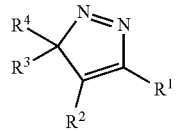
(XX-20)
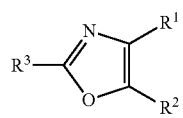
(XX-21)

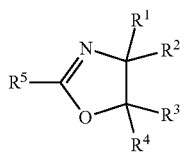 (XX-22)
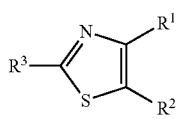 (XX-23)
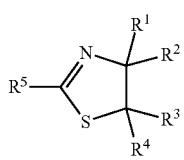 (XX-24)
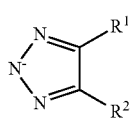 (XX-25)
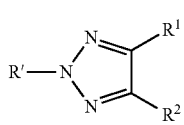 (XX-26)
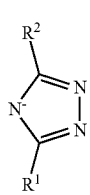 (XX-27)
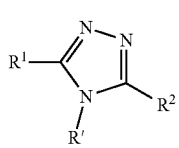 (XX-28)
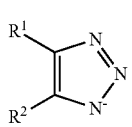 (XX-29)
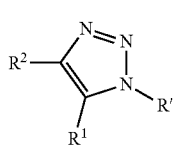 (XX-30)
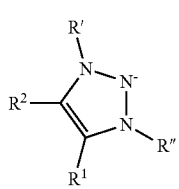 (XX-31)
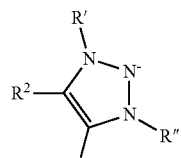 (XX-32)
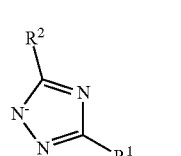 (XX-33)
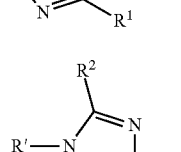 (XX-34)
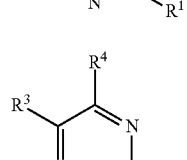 (XX-35)
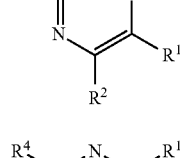 (XX-36)
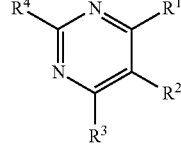 (XX-37)
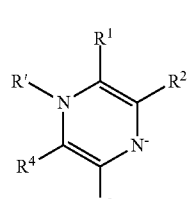 (XX-38)
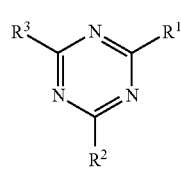 (XX-39)

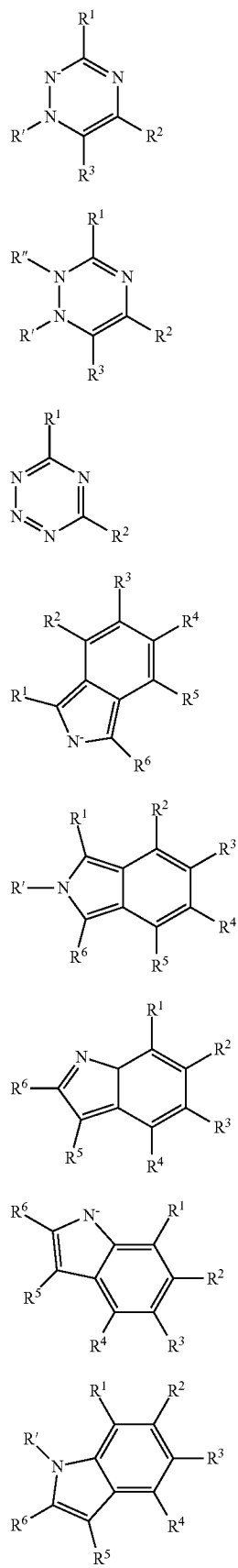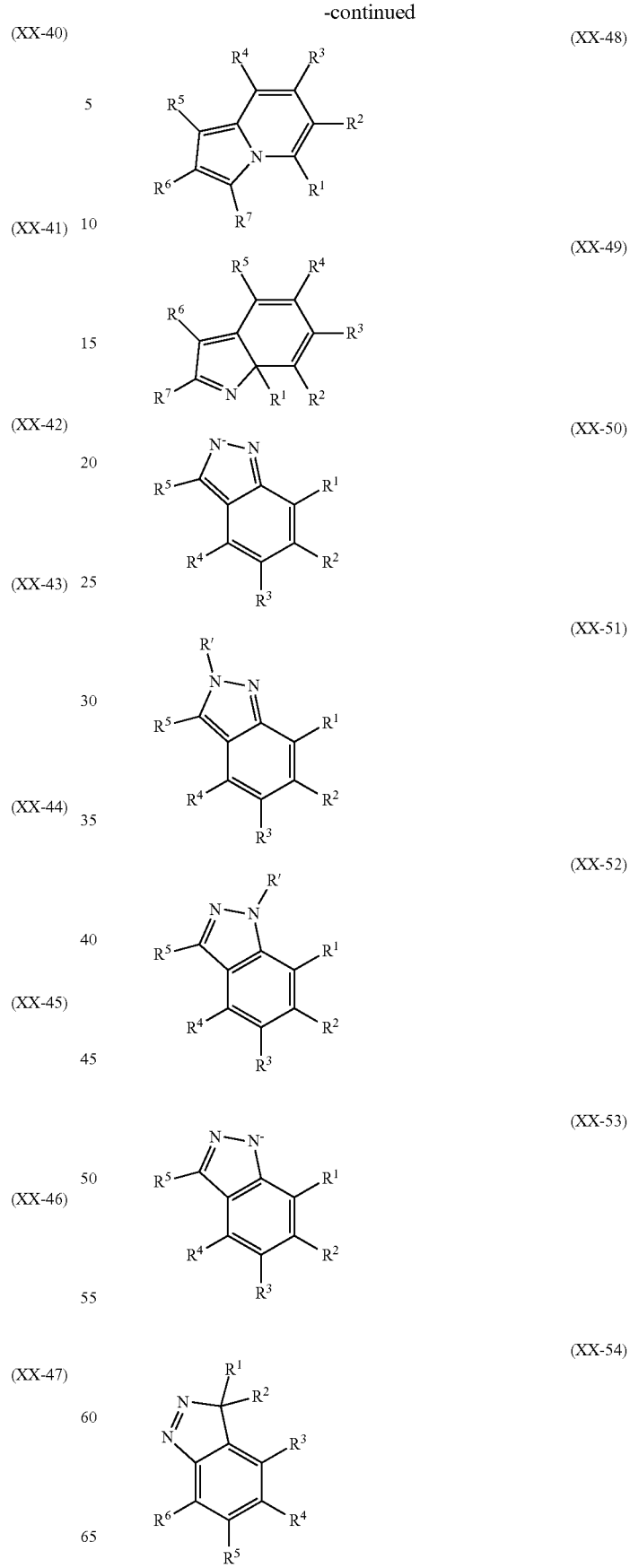

-continued
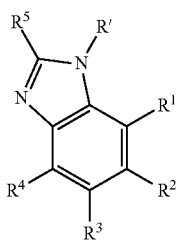
(XX-55)
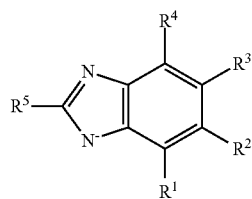
(XX-56)
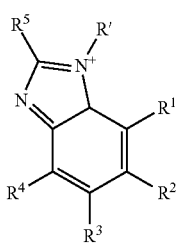
(XX-57)
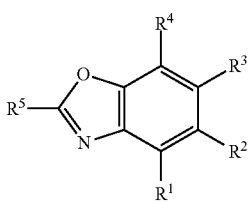
(XX-58)
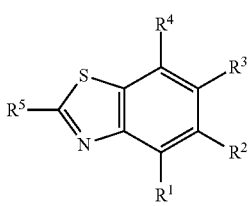
(XX-59)
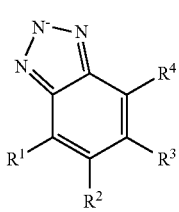
(XX-60)
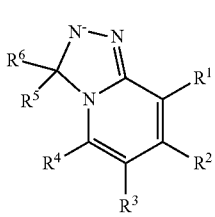
(XX-61)
-continued
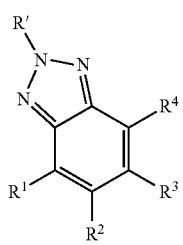
(XX-62)
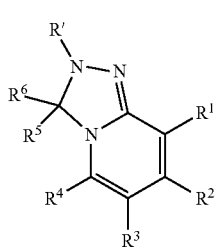
(XX-63)
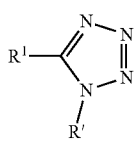
(XX-64)
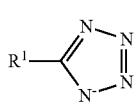
(XX-65)
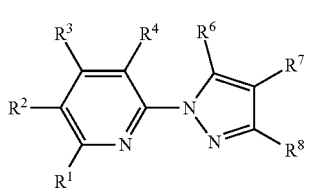
(XX-66)
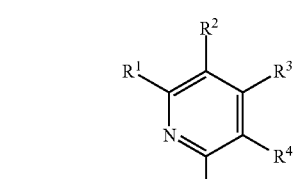
(XX-67)

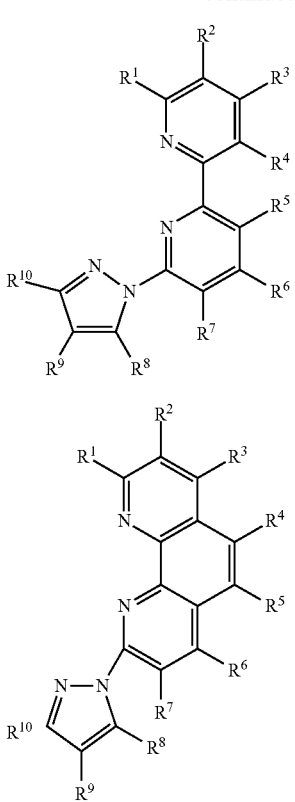

(XX-68)

(XX-69)

wherein:

R$^1$, R$^2$, R$^3$, R$^4$, R$^5$, R$^6$, R$^7$, R$^8$, R$^9$, R$^{10}$, R$^{11}$ and R$^{12}$ of moieties (XX-1) to (XX-69) are independently selected from H, halogen, Cl$^-$, Br$^-$, I$^-$, —NO$_2$, —OH, —NH$_2$, —COOH, —CN, —OCN$^-$, isocyanate group, sulfonyl group and substituents comprising 1 to 40 carbons and 0 to 20 heteroatoms and/or groups selected from —O—, —C(O)—, —C(O)O—, —S—, —S(O)—, SO$_2$—, —S(O)$_2$O—, —N=, —P=, —NR$^{13}$—, —PR$^{13}$—, —P(O)(OR$^{13}$)—, —P(O)(OR$^{13}$)O—, —P(O)(NR$^{13}$R$^{13}$)—, —P(O)(NR$^{13}$R$^{13}$R$^{13}$)O—, —P(O)(NR$^{13}$R$^{13}$)NR$^{13}$—, —S(O)NR$^{13}$—, and —S(O)$_2$NR$^{13}$, with R$^{13}$ being independently selected from H, C1-C6 alkyl, C4-C20 aryl group, C4-C20 arylalkyl group and C4-C20 heteroaryl group, wherein the heteroatom is selected from N, S, or O, and said alkyl, arylalkyl and heteroaryl groups being optionally perfluorinated;

R' and R" are independently selected from —CH$_2$R$^1$, —CHR$^1$R$^2$ and —CR$^1$R$^2$R$^3$, R$^1$R$^2$ and R$^3$ being defined as above; and Xb is a monodentate co-ligand independently selected from H$_2$O, Cl$^-$, Br$^-$, I$^-$, CN$^-$, NCO$^-$, NCS$^-$, NCSe, NH$_3$, NR$_7$R$_8$R$_9$, or PR$_7$R$_8$R$_9$, wherein R$_7$, R$_8$, and R$_9$ are selected independently from substituted or unsubstituted C1-C20 alkyl, C2-C20 alkenyl, C2-C20 alkynyl, and C4 to C20 aryl.

In a further aspect, the invention provides an electrochemical and/or optoelectronic device comprising a dopant of the invention comprising a complex of formula (XX).

In an aspect, the invention provides a complex of formula (I):

$$M(La)_n(Xb)_m \qquad (I)$$

wherein:

M is a metal selected from first row transition metals, in particular cobalt, nickel, copper, and from Ru, Os, Rh, Ir, Pd, Pt, Au, and Ag;

n is an integer from 1 to 6 and a is a consecutive number of a first set consisting of the integers of 1 to n (1, . . . , n), so that there are n ligands L1, . . . , Ln;

m is 0 or an integer from 1 to 5 and b is a consecutive number of a second set consisting of 0 and integers of 1 to m (0, . . . , m), so that if m>0 there are m ligands X1, . . . , Xm;

wherein n+m equal the appropriate number of ligands present on metal M;

any La (L1, . . . , Ln) is independently selected from a mono-, bi-, or tridentate ligand, with the proviso that at least one of said La (L1, . . . , Ln) comprises a substituted or unsubstituted ring or ring system comprising a five- and/or six-membered, N-containing heteroring, said five- or six-membered heteroring, respectively, comprising at least one double bond;

Xb is independently a monodentate co-ligand.

In an aspect, the present invention provides a doped charge transporting material comprising an organic hole or electron transporting material and the complex of formulae (I).

In an aspect, the present invention provides an electrochemical and/or optoelectronic device comprising said complex of the invention. Preferably, the device is a photoelectrochemical device.

In an aspect, the present invention provides an electrochemical device comprising a first and a second electrode and, between said first and second electrode, an organic charge transport layer, said charge transport layer comprising the complex of formula (I)

In an aspect, the present invention provides a photoelectric conversion device comprising a light absorption layer (3) and an electron or hole conducting, organic charge transport layer (6), said charge transport layer comprising the complex of formula (I).

In an aspect, the present invention provides the use of the complex of the invention as a redox active agent of an electrochemical device.

In an aspect, the invention provides the use of complexes of the invention as a dopant for doping an organic semiconductor, a charge injection layer, a hole blocker layer, an electrode material, a transport material, a memory material, or combinations comprising two or more of the aforementioned.

In an aspect, the invention provides the use of the complex of the invention as a dopant, in particular as a p-dopant or as an n-dopant.

In an aspect, the invention provides the use of a complex of the invention for increasing one or more selected from conductivity, charge density and/or charge mobility of an organic charge transporting material.

In an aspect, the invention provides the use of the complex of the invention for increasing the conductivity of an organic semiconductor.

In an aspect, the invention provides the use of the complex of the invention as an additive of an organic semiconductor.

In an aspect, the invention provides the use of the complex of the invention as an overvoltage protection agent.

In an aspect, the invention provides the use of the complex of the invention as an over-discharge prevention agent.

In an aspect, the invention provides the use of the complex of the invention as an explosion prevention agent in rechargeable batteries.

In an aspect, the invention provides the use of the complex of the invention in redox batteries. The complex of the invention is thus useful to improve charge collection and or charge transfer at interfaces.

In an aspect, the invention provides the use of the complex of the invention in layers applied by evaporation.

In an aspect, the present invention provides a method of preparing a charge transporting material, the method comprising the step of providing an organic charge transporting material, and, adding thereto the complex of formula (I).

In an aspect, the present invention provides a method of preparing an electrochemical device, the method comprising the steps of providing a first and a second electrode and providing, between said first and second electrode, an organic charge transporting material comprising the complex of formula (I).

In an aspect, the invention provides a method for doping an organic charge transporting material, the method comprising the step of adding, to said material, the complex of formula (I).

In an aspect, the invention provides a method for increasing the conductivity of an organic semiconductor, the method comprising the step of adding, to said semiconductor, the complex of formula (I).

In an aspect, the invention provides a method for preventing over-discharge of a rechargeable battery, the method comprising the step of adding the complex of formula (I) to the battery.

Further aspects and embodiments of the present invention are described below.

BRIEF DESCRIPTION OF THE FIGURES

In the figures.

DETAILED DESCRIPTION OF THE EMBODIMENTS

Figure 1:
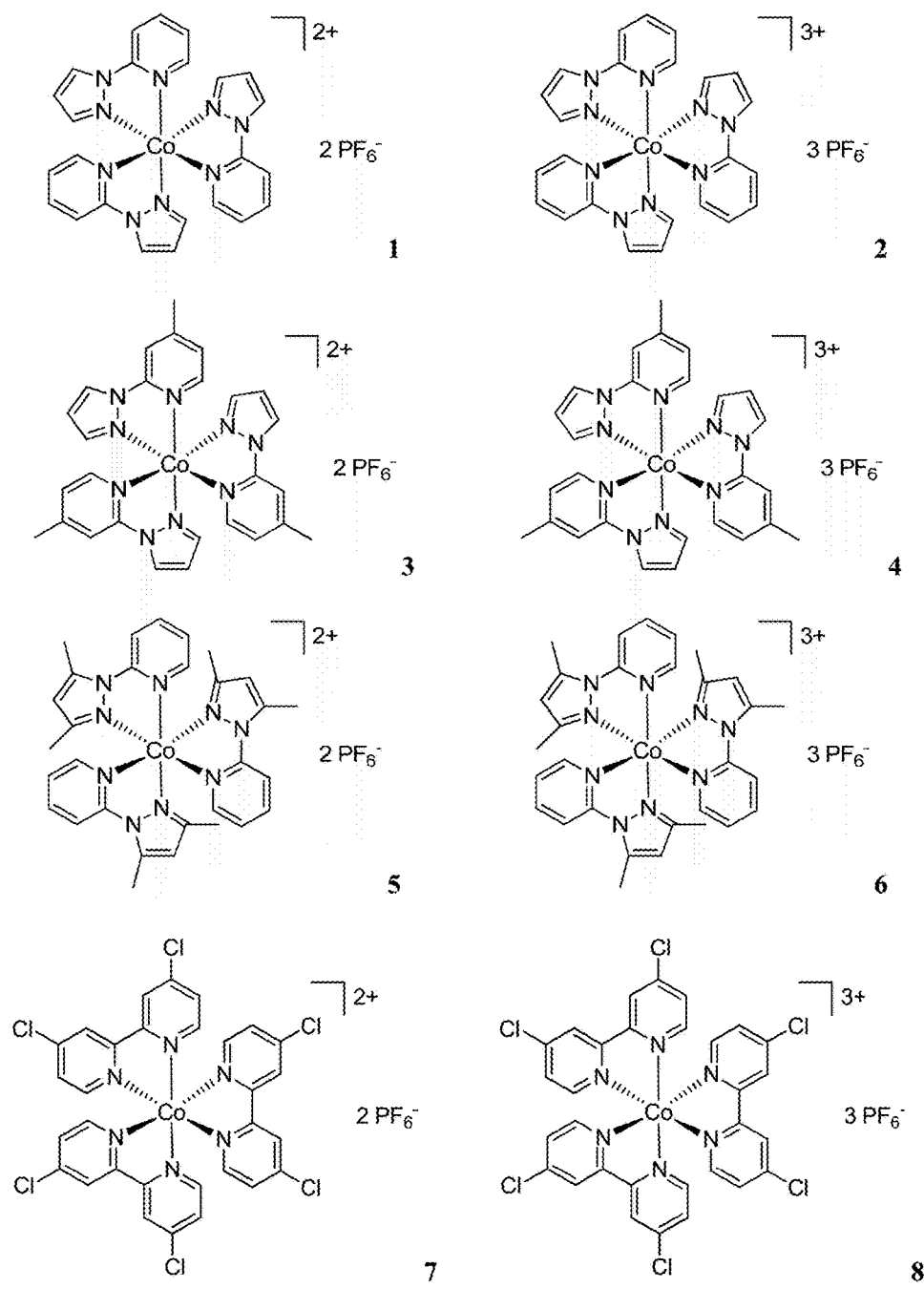
FIG. 1 shows exemplary complexes 1-8 and their salts in accordance with the present invention.

The present invention relates to complexes comprising a metal atom selected from first row transition metals and/or from metals of groups 8 to 11 of the periodic table, in particular the platinum group metals (Ru, Os, Rh, Ir, Pd, Pt), Silver (Ag) and Gold (Au).

According to an embodiment, the metal atom M may thus be selected preferably from the metals Sc, Ti, V, Cr, Mn, Fe, Co, Ni, Cu, Ru, Pt, Rh, Ir and Zn. Preferably, the metal M is selected from Co, Rh, Ir, Ni, Cu, Ru and Pt.

According to an embodiment, M is selected from Fe, Co, Ni, and Cu.

According to an embodiment, the complexes of the invention comprise a metal atom selected from cobalt (Co), rhodium (Rh), and iridium (Ir). Most preferably, M is cobalt (Co).

The term "comprising", for the purpose of the present specification, is intended to mean "includes, amongst other". It is not intended to mean "consists only of".

As the complex of the invention may form a redox couple, the metal atom M may be present at different oxidation levels in the complex of the invention. For example, the metal atom may be present in the +II and/or +III oxidative states. These oxidation numbers may apply, for example, if M is cobalt.

The complex comprises one or more ligands, preferably two or more ligands. According to an embodiment, the complex comprises at least one N-containing heteroring and/or a ring system comprising at least one N-containing heteroring. Said heteroring and/or ring system may be substituted or unsubstituted. Preferably, the heteroring is a five- or six-membered heteroring comprising at least one nitrogen atom and preferably comprising at least one double bond.

According to a preferred embodiment, the complex of the invention comprises a structure of formula M (La)n (Xb)m as defined above as formula (I).

Since n may be an integer from 1 to 6, the complex of formula (I) contain at least one but possibly up to six ligands La. Accordingly, the coordination number of the complex of the invention is preferably four (4) or six (6), meaning that there are preferably four or six donor atoms of ligands (with the preferred or according metals) that are attached to the metal (M). In other words, the ligands (La)n (L1, . . . , Ln) and (Xb)m (if applicable) together provide four, more preferably six donor atoms that are bound to the metal M by a coordinate covalent bond.

The different embodiments of the complex of formula (I) are shown below in the case of coordination number is 6. The same applies analogously in case the coordination number is 4.

In case n is 1 and L1 is a monodentate ligand, m is 5:
(II) M L1 X1 X2 X3 X4 X5, wherein X1 to X5 may be the same or different.

In case n is 1 and L1 is a bidentate ligand (m is 4):
(III) M L1 X1 X2 X3 X4, wherein X1 to X4 may be the same or different.

In case n is 1 and L1 is a tridentate ligand (m is 3):
(IV) M L1 X1 X2 X3, wherein X1 to X3 may be the same or different.

In case n is 2 and L1 and L2 are both monodentate ligands (m is 4):
(V) M L1 L2 X1 X2 X3 X4, wherein L1 and L2 may be the same or different, and any one of X1 to X4 may be the same or different.

In case n is 2 and L1 and L2 are both bidentate ligands (m is 2):
(VI) M L1 L2 X1 X2, wherein L1 and L2 may be the same or different, and X1 and X2 may be the same or different.

In case n is 2, L1 and L2 are a mono- and a bidentate ligands, respectively (m is 3):
(VII) M L1 L2 X1 X2 X3, wherein L1 and L2 are different any one of X1 to X3 may be the same or different.

In case n is 2 and L1 and L2 are a mono- and a tridentate ligand, respectively (m is 2):
(VIII) M L1 L2 X1 X2, wherein L1 and L2 are different and any one of X1 and X2 may be the same or different.

In case n is 2, L1 is a bidentate ligand and L2 is a tridentate ligand (m is 1):
(IX) M L1 L2 X1, wherein L1 and L2 are different.

In case n is 2 and L1 and L2 are both tridentate ligands (m is 0):
(X) M L1 L2, wherein L1 and L2 may be the same or different.

In case n is 3 and L1, L2 and L3 are all monodentate ligands (m is 3):
(XI) M L1 L2 L3 X1 X2 X3, wherein any one of L1 to L3 may be the same or different and any one of X1 to X3 may be the same or different.

In case n is 3 and L1, L2 and L3 are all bidentate ligands (m is 0):
(XII) M L1 L2 L3, wherein any one of L1, L2 and L3 may be, independently, the same or different from any other of L1, L2, L3, respectively. For example, L1 to L3 may all be the same.

In case n is 3, L1 is a bidentate ligand and, L2 and L3 are both monodentate ligands (m is 2):
(XIII) M L1 L2 L3 X1 X2, wherein L1 is different from L2 and L3, L2 and L3 may be the same or different, X1 and X2 may be the same or different.

In case n is 3, L1 and L2 are both bidentate ligands and L3 is monodentate:
(XIIIa) M L1 L2 L3 X1

In case n is 3, L1 is a tridentate ligand, L2 and L3 are both monodentate ligands (m is 1):
(XIV) M L1 L2 L3 X1, wherein L1 is different from L2; L3 and L2 may be the same or different.

In case n is 3, L1 is a tridentate ligand, L2 is a bidentate ligand and L3 is a monodentate ligand (m is 0):
(XV) M L1 L2 L3, wherein L1, L2 and L3 are all different.

In case n is 4, L1 is a bidentate ligand, L2 to L4 are monodentate ligands (m is 1):
(XVI) M L1 L2 L3 L4 X1, wherein L1 is different from L2 to L4; and any one of L2 to L4 may be the same or different.

In case n is 4, L1 is a tridentate ligand, L2 to L4 are monodentate ligands (m is 0):
(XVII) M L1 L2 L3 L4, wherein L1 is different from L2 to L4; and any one of L2 to L4 may be the same or different.

In case n is 4 and L1 to L4 are all monodentate ligands (m is 2):
(XVIII) M L1 L2 L3 L4 X1 X2, wherein any one of L1 to L4 may be the same or different and X1 and X2 may be the same or different.

In case n is 4, L1 and L2 are both bidentate ligands and L3 and L4 are monodentate:

(XVIIIa) M L1 L2 L3 L4, wherein L1 and L2 may be the same or different, and, independently, L3 and 14 may be the same or different.

In case n is 5, L1 is a bidentate ligand and L2 to L5 are all monodentate ligands (m is 0):

(XIX) M L1 L2 L3 L4 L5, wherein L1 is different from L2 to L5 but L2 to L5 may be the same or different.

In the other cases where n is 5 (or 6), m is 1 (or 0, respectively), L1 to L5 (or L1 to L6, respectively), are all monodentate ligands, which may be the same or different.

From the above it becomes apparent that the complexes of the invention may be homoleptic (contain identical ligands La with m being 0) or heteroleptic (containing at least two different ligands).

According to an embodiment, the complex of the invention is selected from the complexes of formulae (II) to (XIX) above.

Preferably, n is 1, 2 or 3, more preferably 2 or 3. If n is 2, L1 and L2 are preferably identical. If n is 3, L1 to L3 are preferably identical.

According to an embodiment of the complex of the invention, n is 2 (M L1 L2) or 3 (M L1, L2, L3) and m is 0 in both cases.

According to an embodiment, the complex of the invention comprises at least 2 or at least 3 ligands La of identical structure (L1=L2 or L1=L2=L3, respectively).

According to an embodiment, the complex of the invention is overall neutral, or carries an overall positive or negative charge. As can be seen from the ligands of the invention as detailed elsewhere in this specification, the charge of the entire complex can be adjusted to be neutral or even negatively charged, in the oxidized or reduced state, as desired, by selecting appropriate negatively charged ligands. For the purpose of the present specification it is considered to be advantageous to be capable of adjusting the charge of the complex, in order to adjust said charge in dependency of other constituents of the electrochemical device of the invention. In particular, the charge of complex can be adjusted to be neutral or negatively charged, so as to avoid electrostatic interactions with other constituents of the electrochemical device.

Herein below, preferred embodiments of the at least one ligand in the complex of the invention are given, said ligand comprising a substituted or unsubstituted ring or ring system comprising a five-membered heteroring and/or a six-membered heteroring. These embodiments also apply for the ligands La (L1, . . . Ln) of the complex of formula (I).

The five- or six membered, N-containing heteroring may be, independently provided as an unsubstituted or substituted heteroring. The heteroring may be fused to another ring or ring system, and/or two substituents of/on a carbon of the heteroring may form a ring, which may result in a spiro compound in which one of the rings is said five- or six membered heteroring. Furthermore, the five- or six membered heteroring may be connected by a covalent bond to another ring or ring system, for example to a pyridine ring or to a polycyclic system containing one or more pyridine rings.

Preferably, said substituted or unsubstituted five- or six membered, N-containing heteroring comprises at least one double bond. According to an embodiment, the five- or six membered heteroring comprises at least two double bonds. According to an embodiment, the five- or six membered heteroring is preferably aromatic.

According to a preferred embodiment, the complex of the invention comprises at least one, more preferably at least two, even more preferably at least three bidentate ligands La, which may be the same or different.

According to another, still more preferred embodiment, the complex of the invention comprises at least one, preferably at least two tridentate ligands La, which may be the same or different.

According to an embodiment, at least one of said n ligands La (L1, . . . , Ln) comprises a pyridine ring (six-membered, N-containing heteroring) or a ring system comprising a pyridine ring connected by a covalent single bond or fused to a further heteroring, which may be five- and/or to a six-membered, wherein said pyridine ring or a ring system comprising a pyridine ring and said further heteroring, independently, may or may not be further substituted.

According to an embodiment, said further five- or six membered heteroring comprises at least one heteroatom selected from the group of N, O, P and S, preferably at least one N.

According to an embodiment, if said ligand La comprises a five-membered heteroring, said five-membered, N-containing heteroring comprises two or more (preferably up to 4) heteroatoms. Preferably, at least a first heteroatom is nitrogen, and at least a second heteroatom or further heteroatom is/are selected, independently, from N, O, P and S. Preferably, said second heteroatom is N, and, if applicable, further heteroatoms (the third, fourth, etc.) are selected independently, from N, O, P and S, preferably they are N.

According to an embodiment, any La (L1, . . . , Ln) ligand is independently selected from substituted and unsubstituted pyridine or polypyridine, substituted and unsubstituted pyrazole, substituted and unsubstituted pyrazine, substituted and unsubstituted triazole, substituted and unsubstituted pyridazine, substituted and unsubstituted imidazole; wherein substituents are independently selected from hydrocarbons comprising 1 to 40 carbons and 0 to 20 heteroatoms, halogen, (—F, —Cl, —Br, —I), —NO$_2$, —NH$_2$ and —OH.

According to an embodiment, any one of said n ligands La (L1, . . . , Ln) is, independently, selected from compounds of formulae (1)-(63) below:

(1)

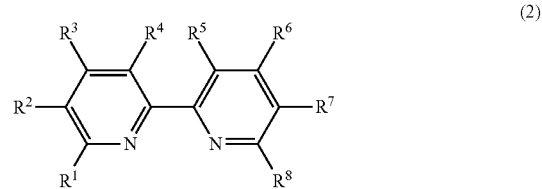

(2)

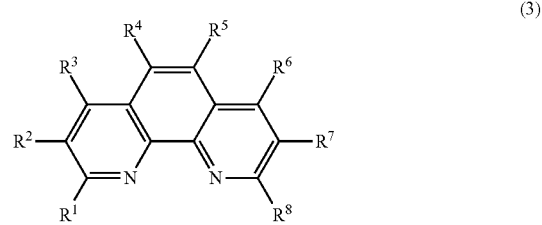

(3)

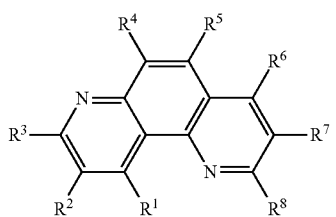
(4)
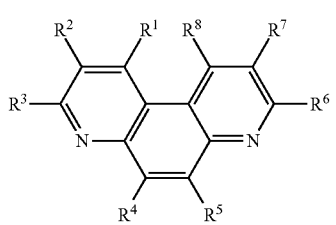
(5)
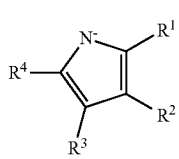
(6)
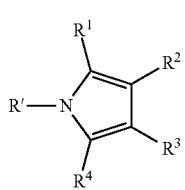
(7)
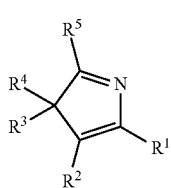
(8)
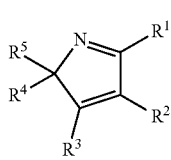
(9)
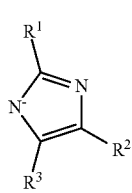
(10)
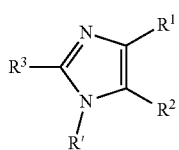
(11)
(12)
(13)
(14)
(15)
(16)
(17)
(18)
(19)
(20)
(21)

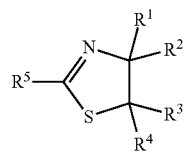 (22)
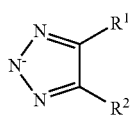 (23)
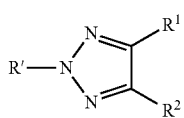 (24)
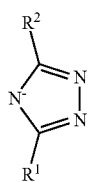 (25)
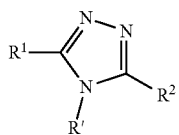 (26)
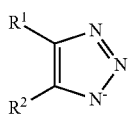 (27)
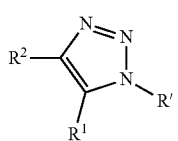 (28)
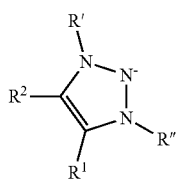 (29)
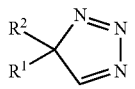 (30)
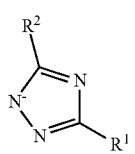 (31)
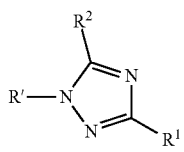 (32)
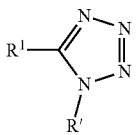 (33)
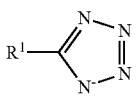 (34)
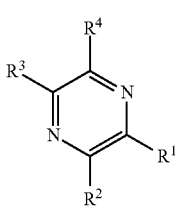 (35)
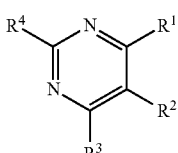 (36)
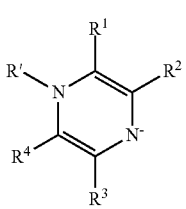 (37)
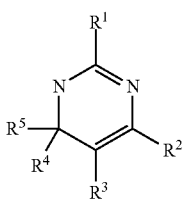 (38)
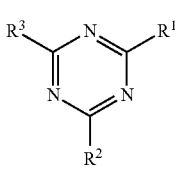 (39)
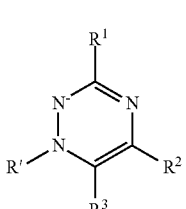 (40)
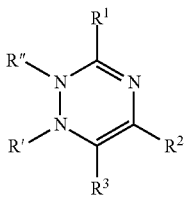 (41)

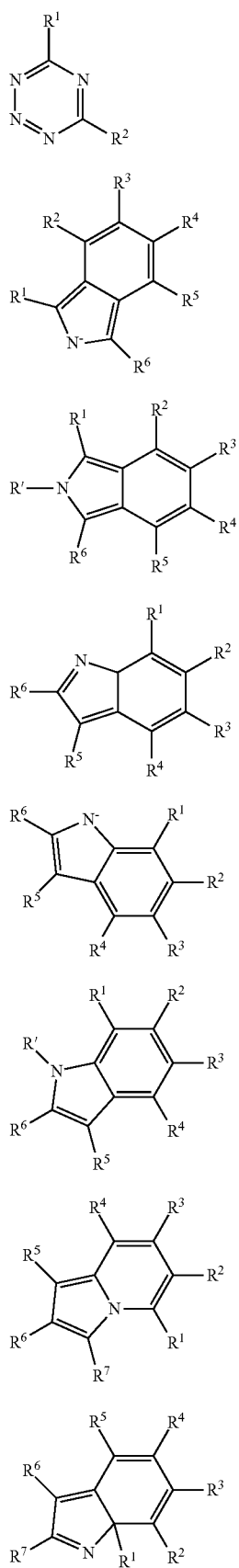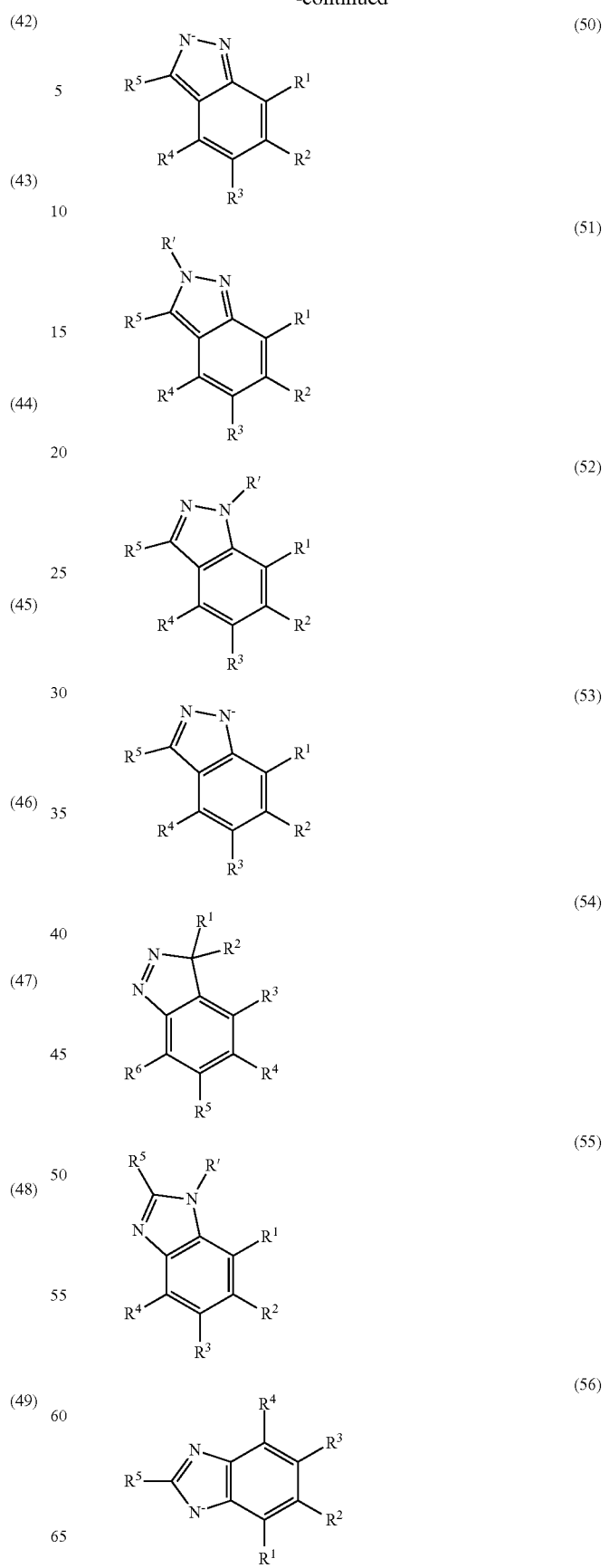

-continued

(57) 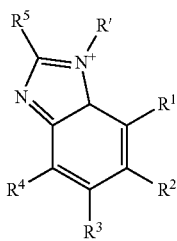

(58) 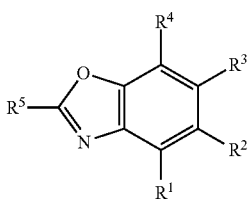

(59) 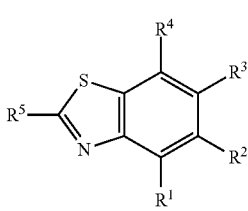

(60) 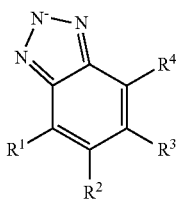

(61) 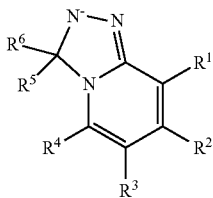

(62) 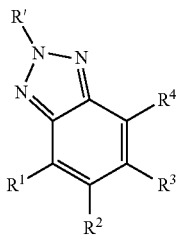

(63) 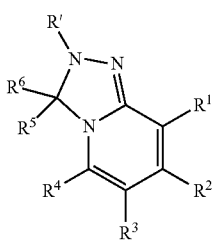

wherein:
any one of $R^1$, $R^2$, $R^3$, $R^4$, $R^5$, $R^6$, $R^7$, $R^8$, if applicable/if present, may be selected, independently, from H and from hydrocarbons comprising 1 to 40 carbons and 0 to 20 heteroatoms; R' and R" are selected, independently from substituents —$CH_2R^1$, —$CHR^1R^2$ and —$CR^1R^2R^3$.

For the purpose of this specification, the expressions "if applicable" and "if present", which are generally preceded by a list or range of substituents (e.g. $R^1$-$R^8$) and followed by a definition of substituents in terms of chemical names (e.g. hydrocarbon, halogen, aryl, alkyl, etc.) are intended to mean that the definition applies only is as a far as and to the extent that a given substituent of the list or range is indeed present on the specific structure formula that is referred to. Substituents of the list that are not present on the formula referred to may be ignored (e.g. compound (1) lacks substituents $R^6$, $R^7$, and $R^8$, which means that the definition given above applies only to the substituents that are present (substituents $R^1$ to $R^5$ in compound (1)).

According to an embodiment, one or more of said substituents $R^1$, $R^2$, $R^3$, $R^4$, $R^5$, $R^6$, $R^7$, $R^8$, if applicable, is selected, independently, from a substituent of formula (A-1) to (G-2) below:

(A-1) 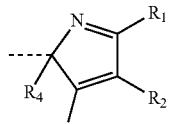

(A-2) 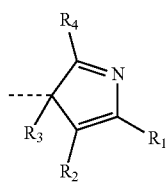

(A-3) 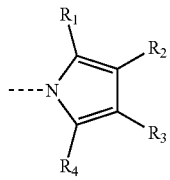

(A-4) 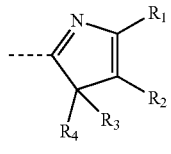

(A-5) 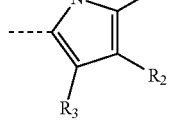

(A-6) 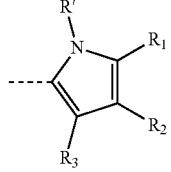

-continued
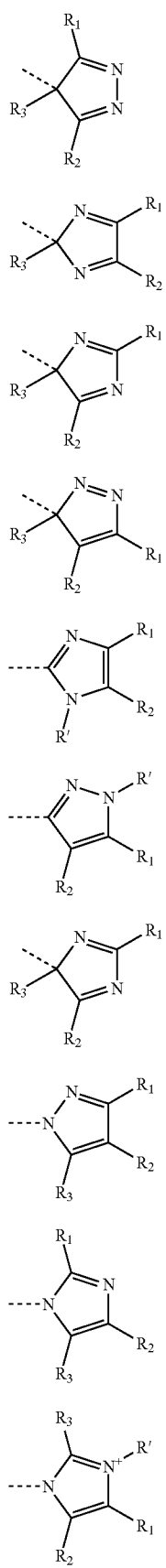
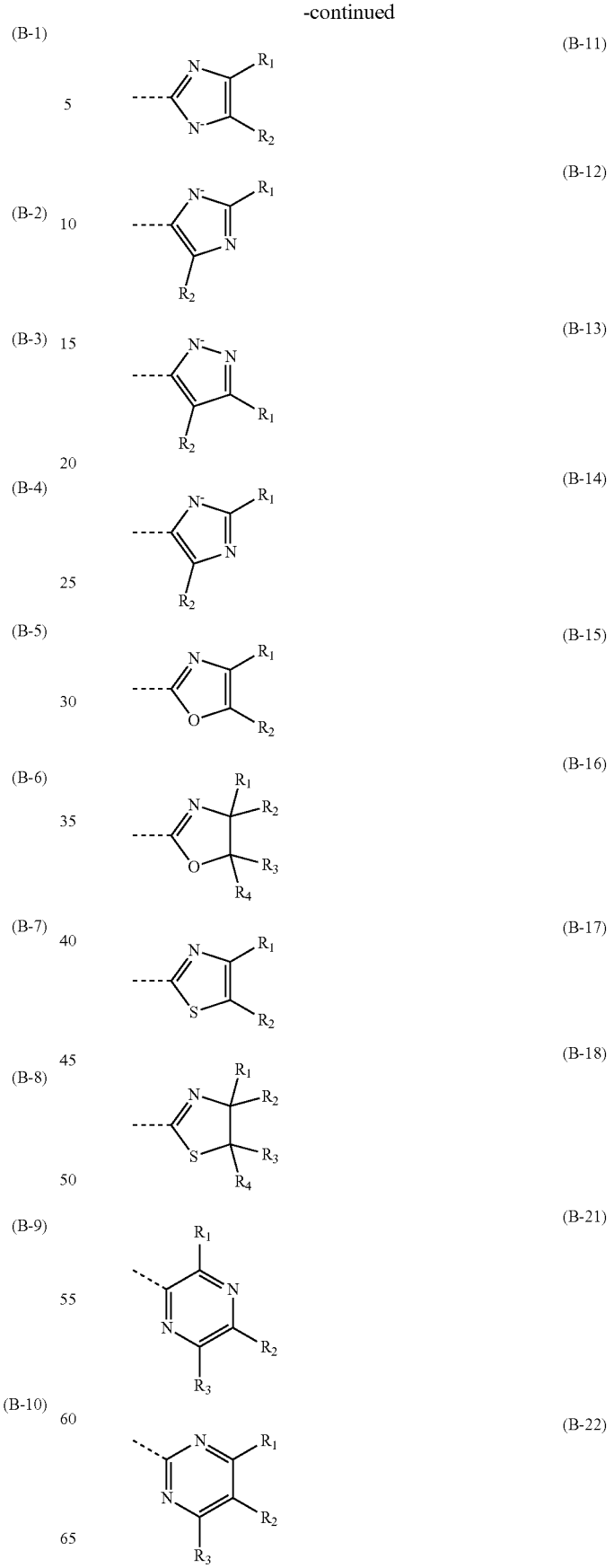

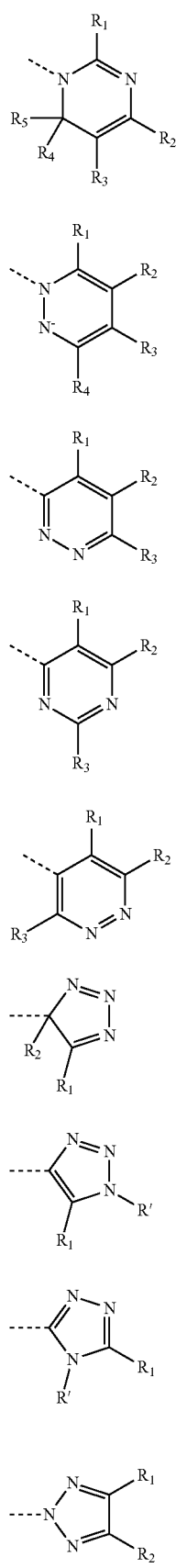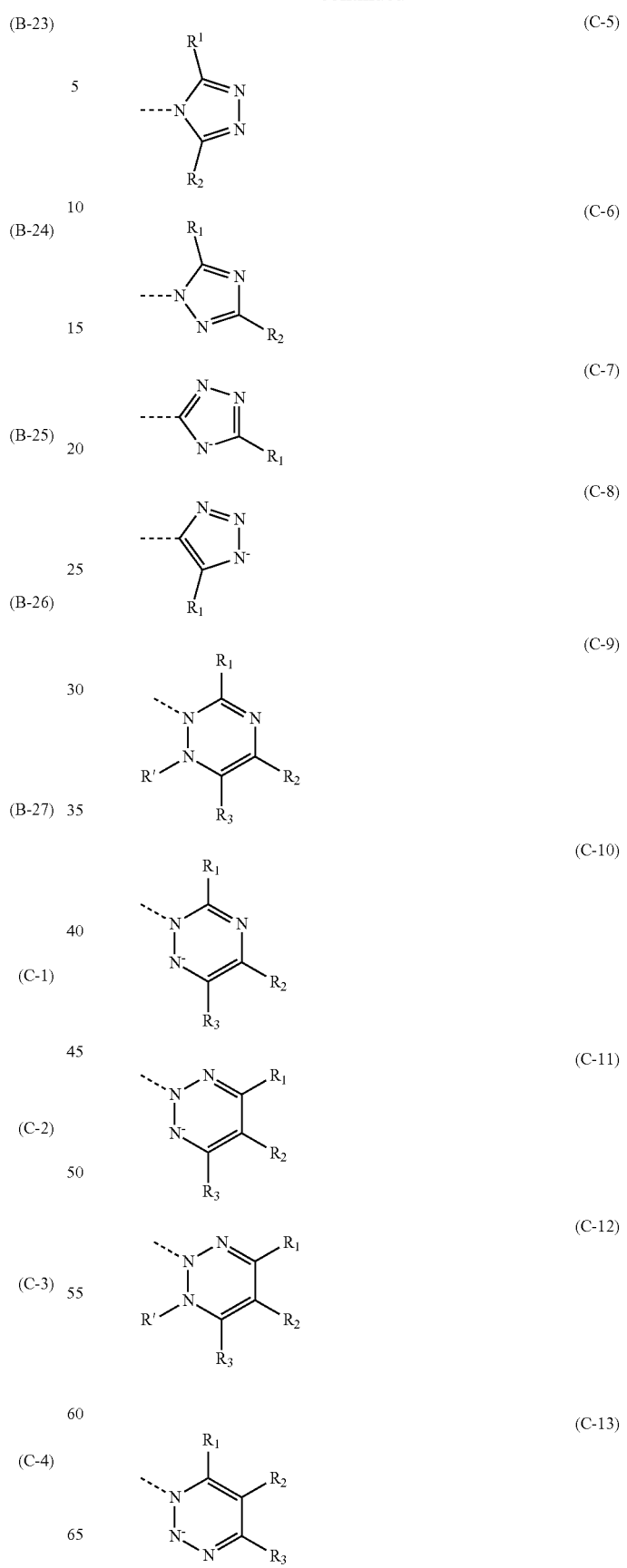

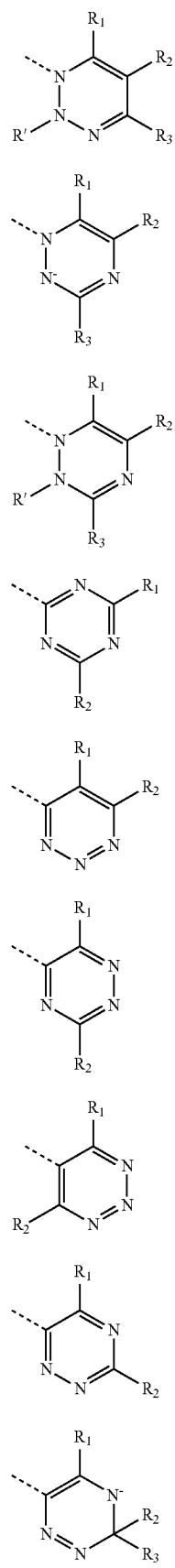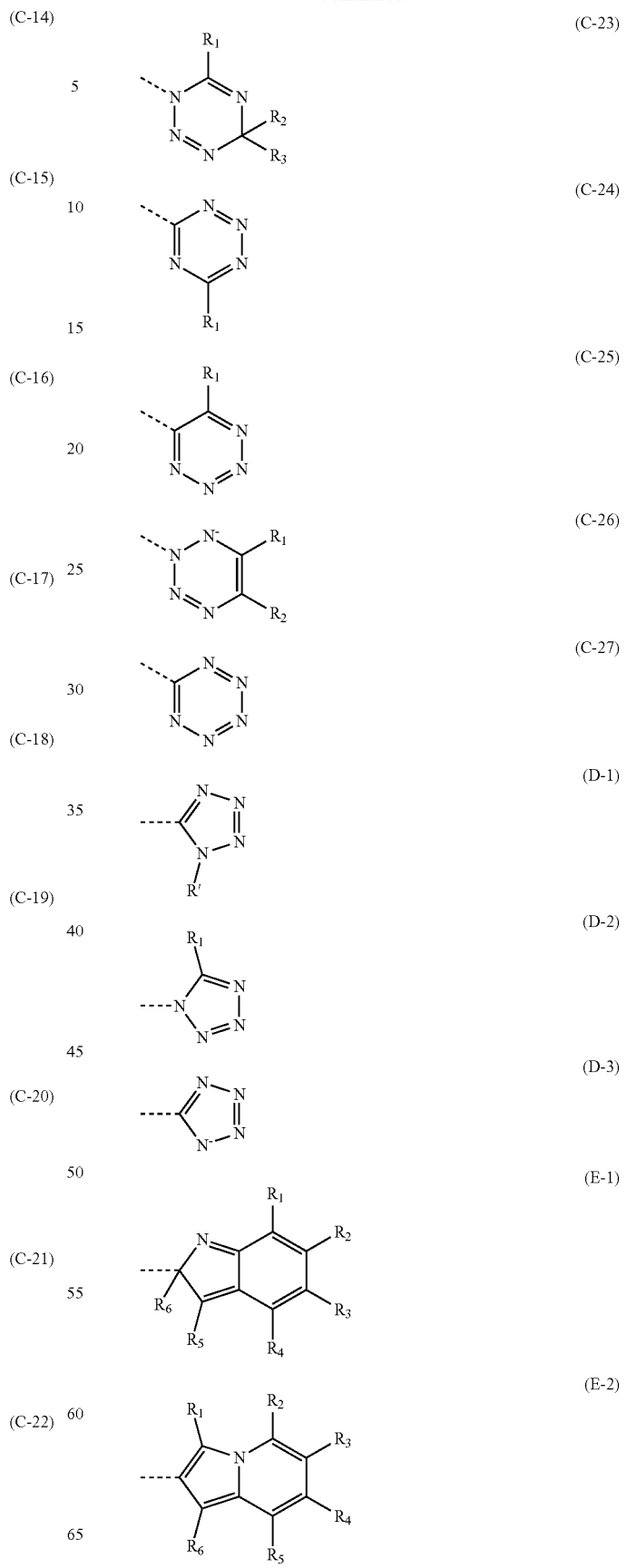

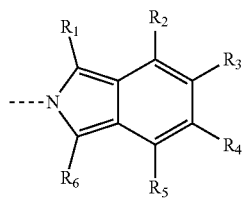
(E-3)

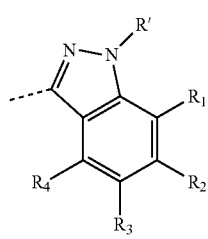
(F-1)

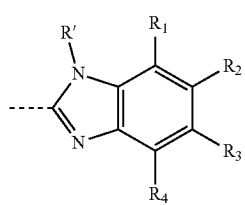
(F-2)

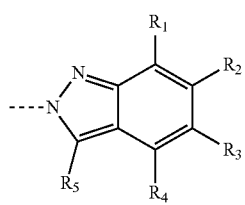
(F-3)

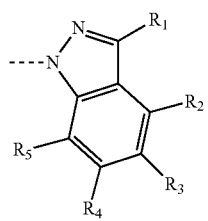
(F-4)

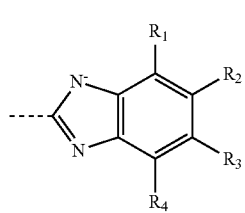
(F-5)

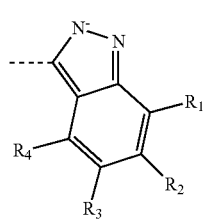
(F-6)

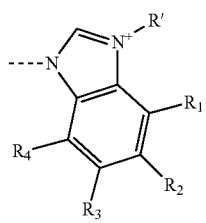
(F-7)

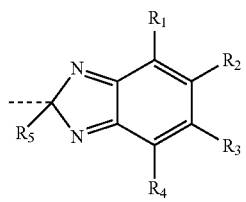
(F-8)

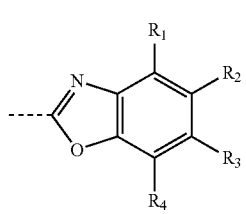
(F-9)

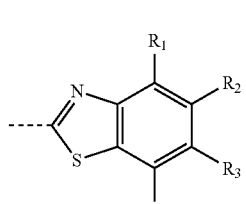
(F-10)

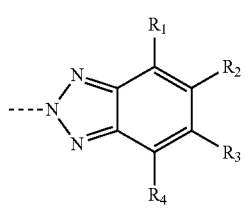
(G-1)

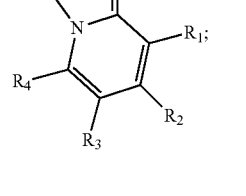
(G-2)

wherein:

the dotted line represents the bond connecting the substituent of (A-1) to (G-2) on the compound of formula (1)-(63); and, substituents $R_1$, $R_2$, $R_3$, $R_4$, $R_5$, $R_6$, and $R_7$, in as far as present, are independently selected from H and from hydrocarbons comprising 1 to 30 carbons and 0 to 15 heteroatoms.

According to an embodiment, at least one of said ligands La (L1, . . . , Ln) is, independently, selected from compounds of formulae (1-2) to (3-2) below:

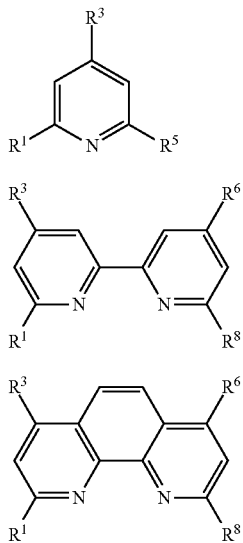

wherein:

at least one substituent of the substituents $R^1$, $R^3$, $R^5$, $R^6$, $R^8$ is selected from the substituents (A-1) to (G-2) as defined elsewhere in this specification. In other words, with respect to ligand (1-2), one, two or three of the group of $R^1$, $R^3$, $R^5$ is selected independently from the substituents (A-1) to (G-2) shown above.

According to an embodiment, at least one of said ligands La (L1, . . . , Ln) is, independently, selected from compounds of formulae (1-3) to (3-3) below:

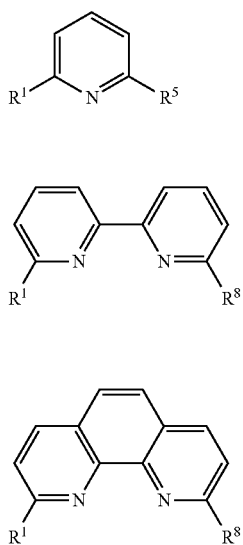

wherein, said ligand comprises at least one substituent $R^1$, $R^5$, and/or $R^8$, as applicable, selected independently from the substituents (A-1) to (G-2) as elsewhere in this specification.

According to an embodiment, any one or at least one of said ligands La is selected independently from the compounds of formula (1-5) to (3-5) below:

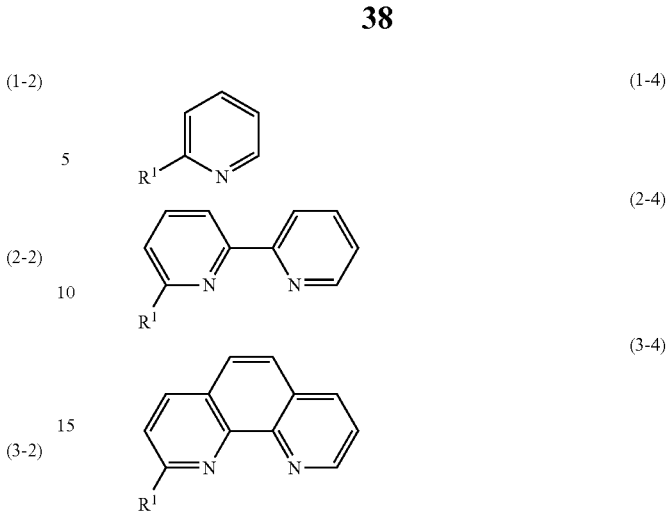

wherein $R^1$ is selected from the substituents (A-1) to (G-2) as disclosed elsewhere in this specification.

In accordance with the present invention, it was surprisingly found that the presence of a second heteroatom in the ring binding to the metal atom of the complex of the invention is suitable to positively affect the properties and suitability of the complex of the invention as a redox couple.

Therefore, ligands (e.g. La) comprising a ring with at least two ring heteroatoms are particularly preferred. According to this embodiment ("embodiment A"), the complex of the present invention comprises one or more ligands selected from: (10)-(42), (50)-(63), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from: (B-1) to (B-27), (C-1) to (C-27), (D-1) to (D-3), (F-1) to (F-10), (G-1) and (G-2).

According to another embodiment ("embodiment A'"), ligands (e.g. La) comprising a ring with exactly two ring heteroatoms are particularly preferred.

According to an embodiment ("embodiment B"), ligands (e.g. La) comprising at least two adjacent ring heteroatoms are particularly preferred. Accordingly, the complex of the present invention comprises one or more ligands selected from: (13), (15), (16), (17), (18), (23) to (34), (40) to (42), (50) to (54), (60) to (63), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from (B-1), (B-4), (B-6), (B-8), (B-13), (B-24), (B-25), (B-27), (C-1) to (C-8), (C9) to (C-16), (C-18) to (C-27), (D-1) to D-3), (F-1), F-3), (F-4), (F-6), (G-1), (G-2).

According to an embodiment ("embodiment C"), ligands (e.g. La) comprising a five-membered heteroring are particularly preferred. Accordingly, the complex of the present invention comprises one or more ligands selected from: (6) to (34), (43) to (63), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from (A-1) to (A-6), (B-1) to (B-18), (C-1) to (C-8), (D-1) to (D-3), (E-1) to (E-3), (F-1) to (F-10), (G-1) and (G-2).

According to an embodiment ("embodiment D"), ligands (e.g. La) comprising a five-membered heteroring that is not fused to any further ring are particularly preferred.

Accordingly, the complex of the present invention comprises one or more ligands selected from: (6) to (34), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from (A-1) to (A-6), (B-1) to (B-18), (C-1) to (C-8), (D-1) and to (D-3).

According to an embodiment ("embodiment E"), ligands (e.g. La) comprising a five- or six-membered heterering having aromatic properties (being aromatic) are particularly preferred. Accordingly, the complex of the present invention comprises one or more ligands selected from: (1) to (5), (6), (7), (10) to (12), (15), (16), (19), (21), (23) to (28), (31) to (34), (35) to (36), (39), (42), (43) to (48), (50) to (53), (55) to (56), (58) to (60) and (62), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from: (A-1) to (G-2).

According to an embodiment ("embodiment F"), the invention provides complexes comprising one or more bi- or tridentate ligands (e.g. La) containing at least one pyridine ring and at least one substituent, wherein said substituent is bound by way of a carbon-nitrogen bond to said pyridine ring. Preferably, the present invention provides complexes comprising one or more ligands of formula (1), (2), (3), (4), (1-2), (2-2), (3-2), (1-3), (2-3), (3-3), (1-4), (2-4), and/or (3-4), wherein said ligands contain one or more substituents selected from: (A-3), (B-8) to (B-10), (B-23), (B-24), (C-4) to (C-6), (C-9) to (C-16), (C-23), (C-26), (D-2), (E-3), (F-3), (F-4), (F-7), (G-1).

According to an embodiment ("embodiment G"), the complex of the invention comprises one or more bi- or tridentate ligands (e.g. La) comprising at least one pyridine ring and at least one substituent selected from substituents (A-1) to (A-6), (B-1) to (B-27), (C-1) to (C-27), (D-1) to (D-3), (E-1) to (E-3), (F-1) to (F-19) and (G-1) to (G-2).

The above embodiments A to G may be combined with each in as far as possible in order to provide more specifically preferred embodiments. For example, according to a preferred embodiment, the complex comprise a ligand selected from compounds that meets the definition of two or more of embodiments A to G (the cut-set, overlap or intersection ∩). For example, the complex of the invention comprises a ligand selected from ligands comprising a five-membered heterering and which ligand has, at the same time, aromatic properties (the overlap of embodiments C and E).

Further particularly preferred embodiments are the overlap of embodiments A and B; A and C; A and D; A and E; A and F. Further preferred embodiments are provided by the overlap of embodiments B and C; B and E; B and F, B and G; B and F. Further preferred embodiments are the overlap of embodiments C and D; C and E; C and F; C and G. Further preferred embodiments are the overlap of embodiments D and E; D and F; D and G. Further preferred embodiments are the overlap of embodiments E and F; E and G. A further preferred embodiment is the overlap of embodiments F and G.

Further preferred embodiments are provided by the overlap of three embodiments selected from embodiments A to G. Such specifically preferred embodiments are provided by the following overlaps of embodiments: A, B and C; A, B and D; A, B, and E; A, B and F; A, B and G; A, C and D; A, C and E; A, C and F; A, C and G; A, D and E; A, D and F; A, D and G; A, E and F; A, E and F; B, C and D; B, C and E; B, C and F; B, C and G; B, D, and E; B, D and F; B, D and G; B, E and F; B, E and G; B, F and G; C, D and E; C, D and F; C, D and G; C, E and F; C, E and G; C, F and G; D, E and F; D, F and G.

For example, the overlap of embodiments A, B and C (underlined above) relates to complexes of the invention comprising a ligand having a five-membered ring (C) containing at least two (A) adjacent (B) heteroatoms. These ligands are those represented by compounds (13), (15) to (18), (23) to (34), (50) to (54), (60) to (63), and preferably the compounds of formulae (1) to (5), (1-2), (2-2), (3-2), (1-3), (2-3), (3-3), (1-4), (2-4), (3-4), in as far as these latter compounds comprise at least one substituent selected from the substituents (B-1), (B-4), (B-6), (B-8), (B-13), (C-1) to (C-8), (D-1) to (D3), (F-1), (F-3), (F-4), (F-6), (G-1), (G-2).

Further preferred embodiments are provided by the overlap of four embodiments selected from embodiments A to G. Such specifically preferred embodiments are provided by the following overlaps of embodiments: A, B, C, and D; A, B, C, and E; A, B, C, and F; A. B. C and G; A, B, D, and E; A, B, D and F; A, B, D and G; A, C, D and E; A, C, D and F; A, C, D and G; A, C, E and F; A, C, E and G; A, D, E and F; A, D, E and G; A, E, F and G; B, C, D and E; B, C, D and F; B, C, D and G; B, C, E and F; B, C, E and G; B, C, F and G; B, D, E and F; B, D, E and G; B, E, F and G; C, D, E and F; C, D, E and G; C, D, F and G; D, E, F and G.

For example, an overlap of embodiments, A, B, C, and G (underlined above), relates to complexes of the invention comprising a bi- or tridentate ligand (La) comprising at least one pyridine ring (G), and a substituent having a five-membered ring (C) containing at least two (A) adjacent (B) heteroatoms. Preferred ligands of this embodiment are those represented by compounds of formulae (1) to (5), (1-2), (2-2), (3-2), (1-3), (2-3), (3-3), (1-4), (2-4), (3-4), in as far as these latter compounds comprise at least one substituent selected from the substituents (B-1), (B-4), (B-6), (B-8), (B-13), (C-1) to (C-8), (D-1) to (D3), (F-1), (F-3), (F-4), (F-6), (G-1), (G-2).

In the embodiments and the preferred, combined or particular embodiments above, embodiment A may be replaced by embodiment A', resulting in the corresponding overlaps in which a ring with exactly two ring heteroatoms is present.

It is further noted that heteroatoms are as defined above, but nitrogen being the preferred ring-heteroatom. According to an embodiment, when there are exactly two or more than two ring-heteroatoms, said heteroatoms are preferably nitrogen atoms.

As can be noted from the preferred embodiments specified above, substituted and unsubstituted ligands comprising a compound of any one of formulae (1) to (5) are preferred. Still more preferred are embodiments wherein La is selected from substituted and unsubstituted ligands of formulae (1), (2) and (3).

According to an embodiment, at least one, at least two, in case of bidentate ligands, three ligands La is/are selected independently from the compounds shown in FIGS. 6, 7, 8, 9, 10, 11, 12 and/or 13. Accordingly, one, two or more ligands La may be independently selected from any one of ligands H-1 to H-31, J-1 to J-26, K-1 to K-33, L-1 to L-4, M-1 to M-15, N-1 to N-20, P-1 to P16, Q-1 to Q-63.

According to an embodiment, in compounds H-1 to H-31, J-1 to J-26, K-1 to K-33, L1 to L4, Q-1 to Q-26, Q-43 to Q-51, any one, more than one or all available hydrogen may independently be replaced by a substituent other than H as defined above for $R^1$ to $R^8$, and/or $R_1$, to $R_7$, as well as the preferred embodiments of $R^1$ to $R^8$, and $R_1$, to $R_7$ that are other than H. It is noted that in the other exemplary ligands (M-1 to M-15, N-1 to N-20, P-1 to P-16, Q-27 to Q-42 and Q-52 to Q-63) shown in the FIG.s, substituents replacing available hydrogens are already present, these latter exemplary ligands thus form specific examples of ligands/compounds comprising such hydrogen replacing substituents.

Furthermore, in several of the ligands shown in FIGS. 5 to 12, methyl substituents on nitrogen atoms corresponding to R' and R" as defined elsewhere in this specification are present (for example, H-2, H-4, H-6, H-8, etc). These N-methyl substituents may, according to an embodiment, be replaced by other substituents as defined for R' and R" elsewhere in this specification. R' and R" may in particular be selected from C1-C5 alkyl substituents.

According to an embodiment, in compounds H-1 to H-31, J-1 to J-26, K-1 to K-33, L1 to L4, Q-1 to Q-26, Q-43 to Q-51, any one, more than one or all available hydrogen may independently be replaced by —F, —Cl, —Br, —I, (halogen), —NO$_2$, —CN, —OH, —CF$_3$, substituted or unsubstituted C1-C30 alkyl, C2-C30 alkenyl, C2-C30 alkynyl, and C5 to C30 aryl as defined elsewhere in this specification for $R^1$ to $R^8$, and/or $R_1$, to $R_7$, as well as the preferred embodiments of $R^1$ to $R^8$, and $R_1$, to $R_7$ that are other than H.

In particular in any ligand La selected from compounds H-1 to H-31, J-1 to J-26, K-1 to K-33, L1 to L4, Q-1 to Q-26, Q-43 to Q-51, any one, more than one or all available hydrogen may independently be replaced by halogen, —CN, C1-C6 alkyls, C2-C6 alkenyls C2-C6 alkynyls, and C6-C10 aryls, wherein in said alkyls, alkenyls, alkynyls and aryls one, several or all available hydrogen may be replaced by halogen, —CN and —CF$_3$.

More preferably, in any ligand La selected from compounds H-1 to H-31, J-1 to J-26, K-1 to K-33, L1 to L4, Q-1 to Q-26, Q-43 to Q-51, any one, more than one or all available hydrogen may independently be replaced by halogen, —CN, C1-C4 alkyl, wherein in said alkyl one, several or all available hydrogen may be replaced by halogen, —CN and —CF$_3$.

According to an embodiment, the complex of the invention comprises at least one ligand (La) selected from the compounds of any one of formula (1), (2), (3), (1-2), (2-2), (3-2), (1-3), (2-3), (3-3), (1-4), (2-4), (3-4), said compound being substituted with one, or, if applicable, two or three substituents, of formulae (B-8), the other substituents being selected as specified above, but preferably from H, halogen, —CN, —CF$_3$, and C1-C4 alkyls, C2-C4 alkenyls and C2-C4 alkynyls, wherein in said alkyls, alkenyls and alkynyls one, several or all available hydrogen may be replaced by halogen.

According to a preferred embodiment, any one of said La is independently selected from any one of compounds of formula (2), (3), (64), (65), (66), and (67), below:

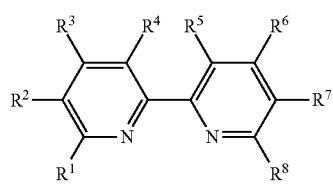
(2)

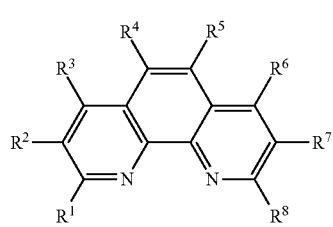
(3)

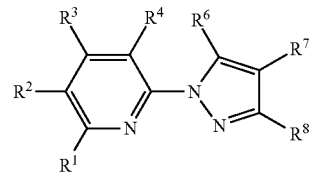
(64)

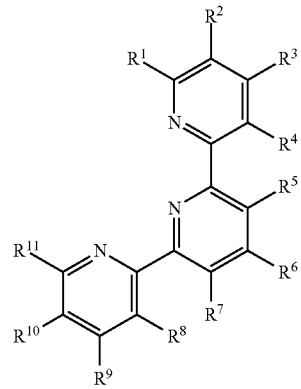
(65)

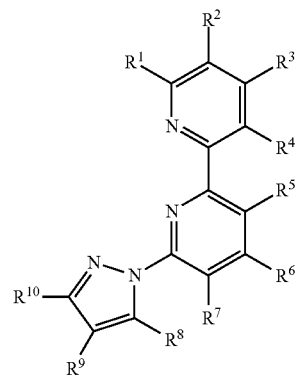
(66)

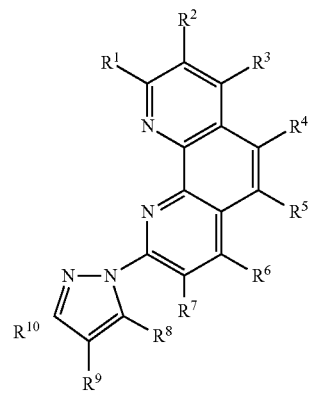
(67)

wherein any one of $R^1$, $R^2$, $R^3$, $R^4$, $R^5$, $R^6$, $R^7$, $R^8$, $R^9$, $R^{10}$, $R^{11}$, if applicable, is independently selected from H and from hydrocarbons comprising 1 to 20 carbons and 0 to 15 heteroatoms, halogen, (—F, —Cl, —Br, —I), —NO$_2$, —NH$_2$, and —OH.

Further exemplary ligands La are disclosed in FIGS. 5 to 12 of the co-pending European patent applications EP11156029.8, filed on Feb. 25, 2011, EP11161739.5, filed on Apr. 8, 2011. The ligands disclosed in these applications (H-1 to H-31, J-1 to J-26, K-1 to K-33, L-1 to L-4, M-1 to M-15, N-1 to N-20, P-1 to P16, Q-1 to Q-63) and their possible substituents, as disclosed on page 28-30 of the co-pending application are totally and entirely incorporated herein by reference.

According to an embodiment, any one of $R^1$, $R^2$, $R^3$, $R^4$, $R^5$, $R^6$, $R^7$, $R^8$, $R^9$, $R^{10}$, $R^{11}$, and of $R_1$, $R_2$, $R_3$, $R_4$, $R_5$, and $R_6$, in as far as the respective substituent is present on the compounds (1) to (67) and their substituents, may thus be independently selected from H, halogen, —$NO_2$, —OH, —$NH_2$ and from hydrocarbons comprising 1 to 30 carbons and 0 to 15 heteroatoms (in the case of $R^1$-$R^{11}$) or from hydrocarbons comprising 1 to 20 carbons and 0 to 15 heteroatoms (in the case of $R_1$-$R_6$).

According to another embodiment, any one of $R^1$, $R^2$, $R^3$, $R^4$, $R^5$, $R^6$, $R^7$, $R^8$, $R^9$, $R^{10}$, $R^{11}$, and of $R_1$, $R_2$, $R_3$, $R_4$, $R_5$, and $R_6$, in as far as the respective substituent is present on the compounds (1) to (67) and their substituents, may thus be independently selected from H, halogen, —$NO_2$, —OH, —$NH_2$ and from hydrocarbons comprising 1 to 20 carbons and 0 to 15 heteroatoms.

Heteroatoms are preferably selected, independently, from Si, N, P, As, O, S, Se halogen (in particular F, Cl, Br and I), B, Be; more preferably from Si, N, P, O, S, and halogen, most preferably from N, O, S and halogen.

According to an embodiment, any one of said substituents $R^1$, $R^2$, $R^3$, $R^4$, $R^5$, $R^6$, $R^7$, $R^8$, $R^9$, $R^{10}$, $R^{11}$, and of $R_1$, $R_2$, $R_3$, $R_4$, $R_5$, $R_6$, $R_7$, $R_8$, and $R_9$ may be independently selected from the substituents of formulae (A-1) to (G-2) (applicable to $R^1$-$R^{11}$), H, halogen (—F, —Cl, —Br, —I), —$NO_2$, —CN, —OH, —$CF_3$, substituted or unsubstituted C1-C20 alkyl, C2-C20 alkenyl, C2-C20 alkynyl, and C4 to C20 aryl; wherein, in said substituted or unsubstituted alkyl, alkenyl, alkynyl or aryl, any hydrocarbon group (preferably and if applicable: non adjacent hydrocarbon group) may be replaced by any one selected from the group of —O—, —S—, —S(=O)—, —S(=O)$_2$—, —Si—, —Ge—, —$NR^A$—, —N=, —$BR^A$—, —$PR^A$—, —P(=O)$R^A$—, —P(=O)O$R^A$—, —C(=O)—, —C(=S)—, —C(=O)O—, —OC(=O)—, —C(=N$R^A$)—, —C=N$R^A$—, —$NR^A$C(=O)—, —C(=O)N$R^A$—, —$NR^A$C(=S)— and —C(=S)N$R^A$—;
wherein, if said alkyl, alkenyl, alkynyl and aryl are substituted, the substituents, may, independently, be selected from halogen, —F, —Cl, —Br, —I, —$NO_2$, —CN, —OH, —$CF_3$, substituted or unsubstituted C1-C15 alkyl, C2-C15 alkenyl, C2-C15 alkynyl C2-C15 alkynyl, C4 to C18 aryl, wherein any hydrocarbon group of said substituent may be replaced by any one selected from the group of —O—, —S—, —S(=O)—, —S(=O)$_2$—, —Si—, —Ge—, —$NR^B$—, —N=, —$BR^B$—, —$PR^B$—, —P(=O)$R^B$—, —P(=O)O$R^B$—, —C(=O)—, —C(=S)—, —C(=O)O—, —OC(=O)—, —C(=N$R^B$)—, —C=N$R^B$—, —$NR^B$C(=)—, —C(=O)N$R^B$—, —$NR^B$C(=S)— and —C(=S)N$R^B$—;
wherein, if said alkyl, alkenyl, alkynyl or aryl substituent is further substituted, the substituents of said substituents, if present, may be selected from halogen, —F, —Cl, —Br, —I, —$NO_2$, —CN, —OH, —$CF_3$, substituted or unsubstituted C1-C8 alkyl, C2-C8 alkenyl, C2-C8 alkynyl, C5 to C8 aryl, wherein any hydrocarbon group of said substituent may be replaced by any one selected from the group of —O—, —S—, —S(=O)—, —S(=O)$_2$—, —Si—, —Ge—, —N=, —C(=O)—, —C(=S)—, —C(=O)O—, —OC(=O)—. Further substituents of said further substituents are preferably selected from halogen, —CN and C1 to C4 alkyl, C2-C4 alkenyl and C2-C4 alkynyl, wherein any available hydrogen of said alkyl, alkenyl or alkynyl may be substituted by halogen.

$R^A$ may be selected from H and from substituted or unsubstituted C1-C15 alkyl, C2-C15 alkenyl, C2-C15 alkynyl C2-C15 alkynyl, C4 to C18 aryl as defined above (including replacement groups). Preferably, $R^A$ is selected from H, C1-C10 alkyl, C2-C10 alkenyl, C2-C10 alkynyl, C4-C10 aryl, —CN, wherein said alkyl, alkenyl, alkynyl and/or aryl may be further substituted with —CN, C1-C4 alkyl (partially or totally halogenated) and halogen. More preferably, $R^A$ is selected from H, —CN, C1-C5 alkyl, C2-C5 alkenyl, C2-C5 alkynyl, C4 to C6 aryl, which may be further substituted by —CN or halogen.

$R^B$ may be selected from H and from substituted or unsubstituted C1-C8 alkyl, C2-C8 alkenyl, C2-C8 alkynyl, C5-C8 aryl as defined above (including replacement groups). Preferably, $R^B$ is selected from H, H, C1-C5 alkyl, C2-C5 alkenyl, C2-C5 alkynyl, C4-C6 aryl, —CN, wherein said alkyl, alkenyl, alkynyl and/or aryl may be further substituted with —CN, C1-C4 alkyl (partially or totally halogenated) and halogen. More preferably, $R^B$ is selected from H, —CN, C1-C4 alkyl, C2-C4 alkenyl, C2-C4 alkynyl, C4 to C6 aryl, which may be further substituted by —CN or halogen.

According to an embodiment, any one of $R_A$, $R_B$ and $R_C$ is independently selected from substituents as defined for $R^A$, preferably $R^B$ as defined elsewhere in this specification, including preferred embodiments of said substituents $R^A$, preferably $R^B$.

For the purpose of the present specification, any alkyl, alkenyl or alkynyl specified herein may be linear, branched and/or cyclic. In this case, the alkyl, alkenyl and alkynyl has three or more (for example up to 30) carbons, as indicated. Any aryl having 4 or 5 carbons has an appropriate number of ring heteroatoms in order to provide an aromatic substituent ring. The expression "aryl" thus encompasses heteroaryls. According to an embodiment, an aryl is selected from heteroaryls and from aryls lacking any heteroatom.

According to a preferred embodiment, any one of $R^1$, $R^2$, $R^3$, $R^4$, $R^5$, $R^6$, $R^7$, $R^8$, $R^9$, $R^{10}$, and $R^{11}$, in as far as present on the compounds (1) to (67), for example, may independently be selected from the substituents of formulae (A-1) to (G-2), H, halogen, —$NO_2$, and from hydrocarbons comprising 1 to 20 carbons and 0 to 10 heteroatoms; preferably from H and C1 to C10 hydrocarbons comprising 0 to 10 heteroatoms; more preferably from H and C1 to C5 hydrocarbons comprising 0 to 5 heteroatoms.

According to a preferred embodiment, any one of $R_1$, $R_2$, $R_3$, $R_4$, $R_5$, $R_6$, $R_7$, $R_8$, and $R_9$ in as far as present on the substituents (A-1) to (G-2) above or on ligands, such as ligands Xb, for example, may be independently selected from H, halogen, —$NO_2$ and from hydrocarbons comprising 1 to 15 carbons and 0 to 10 heteroatoms; preferably from H and C1 to C10 hydrocarbons comprising 0 to 10 heteroatoms; more from preferably H and C1 to C5 hydrocarbons comprising 0 to 5 heteroatoms.

According to an embodiment, any one of $R^1$, $R^2$, $R^3$, $R^4$, $R^5$, $R^6$, $R^7$, $R^8$, $R^9$, $R^{10}$, $R^{11}$, $R_1$, $R_2$, $R_3$, $R_4$, $R_5$, $R_6$, $R_7$, $R_8$, $R_9$, R' and R", if applicable, is selected independently from the substituents of formulae (A-1) to (G-2) (only applicable to $R^1$-$R^{11}$), H, and from C1-C10 alkyls, C2-C10 alkenyls C2-C10 alkynyls, and C5-C12 aryls (preferably C6-C12 aryls), wherein in said alkyls, alkenyls, alkynyls and aryls one, several or all available hydrogen may be replaced by halogen and/or by —CN, wherein any one of said $R^1$ to $R^{12}$ and $R_1$ to $R_6$ may be further selected from halogen, —C≡N (—CN), —$NO_2$. Said aryl may or may not be further substituted by C1-C4 alkyl, halogen and —CN.

According to an embodiment, any one of $R^1$, $R^2$, $R^3$, $R^4$, $R^5$, $R^6$, $R^7$, $R^8$, $R^9$, $R^{10}$, $R^{11}$, $R_1$, $R_2$, $R_3$, $R_4$, $R_5$, $R_6$, $R_7$, $R_8$, $R_9$, R' and R", in as far as present, is selected independently from the substituents of formulae (A-1) to (G-2) (in the case of $R^1$-$R^{11}$), H, and from C1-C6 alkyls, C2-C6 alkenyls C2-C6 alkynyls, and C6-C10 aryls, wherein in said alkyls, alkenyls, alkynyls and aryls one, several or all available hydrogen may be replaced by halogen and/or —CN, wherein any one of said $R^1$ to $R^{11}$ and $R_1$ to $R_6$ may further be selected from halogen and from —C≡N (—CN). Said aryl may or may not be further substituted by C1-C4 alkyl, halogen and —CN.

According to an embodiment, any one of $R^1$, $R^2$, $R^3$, $R^4$, $R^5$, $R^6$, $R^7$, $R^8$, $R^9$, $R^{10}$, $R^{11}$, $R_1$, $R_2$, $R_3$, $R_4$, $R_5$, $R_6$, $R_7$, $R_8$, $R_9$, R' and R", in as far as present, is selected independently, from the substituents of formulae (A-1) to (G-2) (in the case of $R^1$-$R^{11}$), H, and from C1-C6, preferably C1-C4, more preferably C1-C3 alkyl, said alkyl, being optionally partially or totally substituted by halogen, wherein any one of said $R^1$ to $R^{12}$ and $R_1$ to $R_6$ may further be selected from halogen and from —C≡N.

According to an embodiment, any one of $R^1$, $R^2$, $R^3$, $R^4$, $R^5$, $R^6$, $R^7$, $R^8$, $R^9$, $R^{10}$, $R^{11}$, $R_1$, $R_2$, $R_3$, $R_4$, $R_5$, $R_6$, $R_7$, $R_8$, $R_9$, in as far as present, is selected, independently, from the substituents of formulae (A-1) to (G-2) (this only applies to $R^1$-$R^{11}$), H, halogen, —CN and from C1-C6, preferably C1-C4 and most preferably C1-C3 alkyl, said alkyl being possibly substituted by halogen.

According to an embodiment, R' and R" are selected independently from H and from C1-C6 linear branched or cyclic alkyl, said alkyl being possibly and optionally partially or totally substituted by halogen.

According to an embodiment, $R^1$, $R^2$, $R^3$, $R^4$, $R^5$, $R^6$, $R^7$, $R^8$, $R^9$, $R^{10}$, $R^{11}$, in as far as present, are selected independently from the substituents of formulae (A-1) to (G-2), H, halogen, —CN, and from C1-C6 alkyl and alkenyl, wherein any available hydrogen of said alkyl and alkenyl may or may not be replaced by halogen and/or —CN. Preferably, $R^1$, $R^2$, $R^3$, $R^4$, $R^5$, $R^6$, $R^7$, $R^8$, $R^9$, $R^{10}$, $R^{11}$, in as far as present, are selected independently from H, halogen, —CN, and from C1-C4 alkyl, said alkyl being optionally totally or partially halogenated. Preferably, $R^1$, $R^2$, $R^3$, $R^4$, $R^5$, $R^6$, $R^7$, $R^8$, $R^9$, $R^{10}$, $R^{11}$, in as far as present, are selected independently from H, halogen, —CN, —CF3 and C1-C3 alkyl.

According to an embodiment, $R_1$, $R_2$, $R_3$, $R_4$, $R_5$, $R_6$, $R_7$, $R_8$, $R_9$, in as far as present, are selected independently from H, halogen, —CN, and from C1-C6 alkyl and alkenyl, wherein any available hydrogen of said alkyl and alkenyl may or may not be replaced by halogen and/or —CN. Preferably, $R_1$, $R_2$, $R_3$, $R_4$, $R_5$, $R_6$, $R_7$, $R_8$, $R_9$, in as far as present, are selected independently from H, halogen, —CN, and from C1-C4 alkyl, said alkyl being optionally totally or partially halogenated. Preferably, $R_1$, $R_2$, $R_3$, $R_4$, $R_5$, $R_6$, $R_7$, $R_8$, $R_9$, in as far as present, are selected independently from H, halogen, —CN, —CF$_3$ and C1-C4 alkyl. $R_7$-$R_9$ are preferably not selected from halogen and/or CN.

Substituents $R^1$, $R^2$, $R^3$, $R^4$, $R^5$, $R^6$, $R^7$, $R^8$, $R^9$, $R^{10}$, $R^{11}$, $R_1$, $R_2$, $R_3$, $R_4$, $R_5$, $R_6$, $R_7$, $R_8$, $R_9$, other than H are suitable to adjust the oxidation potential of the metal complex. Without wishing to be bound by theory, it is believed that such substituents can help obtaining electrochemical devices, in particular DSCs, with higher $V_{OC}$ values, and to adjust the oxidation potential of the redox couple to the properties of the dye.

The redox-active compound may comprise one or more co- and/or spectator ligands, such as one or more ligands Xb in accordance with the complex of formula (I), for example.

The spectator ligands Xb may be independently selected, for example, from $H_2O$, $Cl^-$, $Br^-$, $I^-$, CN, NCO, NCS, NCSe, $NH_3$, $NR_7R_8R_9$, and $PR_7R_8R_9$, wherein $R_7$, $R_8$, and $R_9$ are selected independently from substituted or unsubstituted alkyl, alkenyl, alkynyl and aryl. According to an embodiment, said alkyl, alkenyl and aryl is independently selected from substituted or unsubstituted C1-C20 alkyl, C2-C20 alkenyl, C2-C20 alkynyl, and C4 to C20 aryl as defined elsewhere in this specification, and preferred embodiments of alkyl, alkenyl, alkynyl and aryl as defined for $R^1$-$R^{11}$ and/or $R_1$-$R_6$ elsewhere in this specification. Furthermore, two or all three of $R_7$, $R_8$, and $R_9$ may connected with each other so as to provide a cyclic or polycyclic ligand.

According to an embodiment, any one of $R^1$, $R^2$, $R^3$, $R^4$, $R^5$, $R^6$, $R^7$, $R^8$, $R^9$, $R^{10}$, $R^{11}$, $R_1$, $R_2$, $R_3$, $R_4$, $R_5$, $R_6$, $R_7$, $R_8$, $R_9$, R' and R", if applicable, is selected independently from the substituents of formulae (A-1) to (G-2) (only applicable to $R^1$-$R^{11}$), H, and from C1-C10 alkyls, C2-C10 alkenyls C2-C10 alkynyls, and C5-C12 aryls (preferably C6-C12 aryls), wherein in said alkyls, alkenyls, alkynyls and aryls one, several or all available hydrogen may be replaced by halogen and/or by —CN, wherein any one of said $R^1$ to $R^{12}$ and $R_1$ to $R_6$ may further be selected from halogen, —C≡N (—CN), —NO$_2$. Said aryl may or may not be further substituted by C1-C4 alkyl, halogen and —CN.

According to an embodiment, any one of $R^1$, $R^2$, $R^3$, $R^4$, $R^5$, $R^6$, $R^7$, $R^8$, $R^9$, $R^{10}$, $R^{11}$, $R_1$, $R_2$, $R_3$, $R_4$, $R_5$, $R_6$, R' and R", if applicable, is selected independently from H, and from C1-C10 alkyls, C2-C10 alkenyls C2-C10 alkynyls, and C5-C12 aryls (preferably C6-C12 aryls), wherein in said alkyls, alkenyls, alkynyls and aryls one, several or all available hydrogen may be replaced by halogen and/or by —CN, wherein any one of said $R^1$ to $R^8$ and $R_1$ to $R_6$ may further be selected from halogen and from —C≡N (—CN).

According to a preferred embodiment, any one of $R_1$, $R_2$, $R_3$, $R_4$, $R_5$, $R_6$, $R_7$, $R_8$, and $R_9$ in as far as present on the substituents (A-1) to (G-2) above or on ligands, such as ligands Xb, for example, may be independently selected from H, halogen, —NO$_2$ and from hydrocarbons comprising 1 to 15 carbons and 0 to 10 heteroatoms; preferably from H and C1 to C10 hydrocarbons comprising 0 to 10 heteroatoms; more from preferably H and C1 to C5 hydrocarbons comprising 0 to 5 heteroatoms.

According to an embodiment, any one of $R_1$, $R_2$, $R_3$, $R_4$, $R_5$, $R_6$ is selected independently from H, halogen, C1-C6 linear alkyl, C3-C6 branched or cyclic alkyl, and —C≡N, wherein any one of said linear, branched or cyclic alkyl may be totally or partially halogenated, and may in particular also be —CF$_3$.

Other ligands of the complex of the invention, in particular ligands Xb (X1, ... , Xm) of the complex of formula (I), may, for example, be selected from: $H_2O$, $Cl^-$, $Br^-$, $I^-$, $CN^-$, $NCO^-$, $NCS^-$, $NCSe^-$, $NH_3$, CO, PR3 (R is independently selected from substituted and unsubstituted C6-C18, preferably C6-C12 aryl and/or aroxyl (for example phenyl or phenoxyl); substituted and unsubstituted C1-C18, preferably C1-10, more preferably C1-C4 alkyl and/or alkoxyl; imidazole, substituted imidazoles; pyridines, substituted pyridines; pyrazoles, substituted pyrazoles; triazoles; pyrazine; for example. Preferably, the ligands Xb (X1, ... , Xm) are selected from $H_2O$, $Cl^-$, $Br^-$, $I^-$, $CN^-$, $NCO^-$, $NCS^-$, $NCSe^-$, $NH_3$, CO, and PR3 (R is as above, preferably independently selected from phenyl, phenoxyl, alkyl and alkoxyl).

The complex of the invention may be charged or uncharged, in dependence of the charge of the ligand. Preferably, the complex is cationic. In this case, the complex is preferably provided together with a suitable anionic species. The anion may be chosen in dependence of the specific device or material, to which the complex is to be added. The anion may be chosen, for example in OLED applications, so as to limit migration of the complex, for example to another layer. Accordingly, the invention provides a salt comprising the complex of the invention and an anionic species.

The anionic species may be an organic or an inorganic anion.

According to an embodiment, the anion is selected from the group consisting of halogen (in particular Cl$^-$, Br$^-$, I$^-$), CN$^-$, NCO$^-$, NCS$^-$, NCSe$^-$, ClO$_4^-$ (perchlorate), PF$_6$ (hexafluorophosphate), BF$_4$ (tetrafluoroborate), B(CN)$_4$ (tetracyanoborate), CF$_3$SO$_3$ (trifluoromethanesulfonate, triflate), (CF$_3$SO$_2$)$_2$N (Bis(trifluoromethane)sulfonamide, TFSI), B(C$_6$H$_3$(m-CF$_3$)$_2$)$_4$ (tetrakis[3,5-bis(trifluoromethyl)phenyl]borate, BARF), B(C$_6$F$_5$)$_4$ (tetrakis(pentafluorophenyl)borate), B(Ph)$_4$ (tetraphenylborate), Al(OC(CF$_3$)$_3$)$_4$, and CB$_{11}$H$_{12}$ (carborane anion).

The invention provides an organic charge transport material comprising the complex of the invention and/or a salt comprising the complex.

In the context of the present invention, the reference to a material comprising the complex of the invention generally encompasses, as a preferred embodiment, a material comprising a salt comprising the complex.

The "organic charge transport material" may also be referred to as organic electron and/or hole transport material. The term "organic" may be omitted, but generally, the charge transport material comprises an organic compound. The "organic charge transport material" is an organic semiconductor and/or conductor based on single molecules, oligomers, polymeric compounds and mixtures of the aforementioned. In the organic charge transport material, charges are substantially transported by electronic motion and/or charge hopping and not or only to an insignificant extent by diffusion of charged molecules. Accordingly, this material may be an electron and/or hole conducting material. U. Bach et al. "Solid-state dye-sensitized mesoporous TiO$_2$ solar cells with high photon-to-electron conversion efficiencies", Nature, Vol. 395, Oct. 8, 1998, 583-585, disclose the amorphous organic hole transport material 2,2',7,7'-tetrakis(N,N-di-p-methoxyphenyl-amine)9,9'-spirofluorene (OMeTAD) in dye-sensitised solar cells. In WO2007/107961, charge transporting materials, which are liquid at room temperature and their application in dye-sensitized solar cells are disclosed (for example, tris(p-methoxyethoxyphenyl)amine (TMEPA)). These and other materials may be used, for example, for the purpose of the present invention. Also EP 1160888 A1 discloses an "organic electrically conducting agent". The "organic charge transport material" thus has characteristics such as a conductivity, which is generally influenced by the presence or absence of a dopant. Typical current carriers in organic semiconductors are holes and electrons in π-bonds. When organic molecules have π-conjugate systems, electrons can move via π-electron cloud overlaps, especially by hopping, tunneling and related mechanisms. Polycyclic aromatic hydrocarbons and phtalocyanine salt crystals are examples of this type of organic semiconductor. In the context of the present invention, an ionic liquid and a liquid electrolyte, in which charges are transported by diffusion of molecules, are not considered as organic charge transport material.

In the context of the invention, the complex (or a salt comprising the complex) of the invention is used to adjust, in particular increase the conductivity of an organic charge transporting material, and/to dope the organic charge transport material. The complex (or salt) may also be used as a dopant in other types of conductors or semiconductors.

The complex or salt comprising the complex may also be used to adjust the ionization potential and/or Fermi level of the organic charge transport material.

The invention thus provides an organic charge transporting material comprising the complex of the invention. The complex may be added at a weight percentage of 0.001 to 10%, preferably 0.01 to 8%, more preferably 0.1% to 5% and most preferably 0.5 to 4%, for example 1 to 3% or 1 to 2.5%, with respect to the weight of the organic charge transporting material. Preferably, the weight percentages do not include any solvent but refer directly and to the organic charge transporting material.

The organic charge material comprising the complex of the invention forms a doped organic charge transport material of the invention.

The complexes of the invention may be used as p-dopants and as n-dopants. For obtaining an n-dopant, the same complexes having the same overall structure as those used for p-dopants can be used. The only difference is that instead of using D+ complex in the D+/D redox couple, the D− in the D/D− redox couple has to be used. Such complexes can be prepared by shaking complex D with alkali metals (potassium or lithium for example). For example, complex 2 (FIG. 1) will generally be used as n-dopant. Complex 2 can be considered as D+[Co(L)3)$^{3+}$]. A complex with same structure but charged as D−, for example [Co(L)3)+] can be used as n-dopant if E(D/D−)<E (reduction of the material to be doped). In addition, while Co3+, a d6 electron system, was used for p-doping, Co+, a d8 electron system could be used for n-doping. The complexes prepared can be multiple electron donor. E.g. [Fe(bpy)3Na] or [Fe(bpy)3] are expected to give 4 and 3 electrons respectively. A complex bis-terdentate would give 2 or 3 electrons. Methods of preparation are disclosed in (1) Mahon, Carol; Reynolds, Warren Lind. Preparation of sodium tris(2,2'-bipyridine)ferrate(-I). Inorganic Chemistry (1967), 6(10), 1927-8. (2) Herzog, Siegfried; Weber, Albert. Alkali metal adducts of some neutral complexes of iron with bipyridine and bipyridine-like ligands. Zeitschrift fuer Chemie (1968), 8(2), 66. WO2005/036667 discloses an electrochemical method.

Reference is made to US 2005/0061232 and US 2010/0140566, which illustrate the use of dopants in organic semiconductors.

The present invention preferably relates to metal complexes comprising a metal atom selected from Cu, Pd, Au, Ag, and V, preferably in the oxidation (II), mono-, bi- or tridentate ligands and optionally a co-ligand. Said preferred metal complex comprises one or more ligands being selected from mono-, bi- or tridentates ligand comprising an aromatic ring system comprising at least one N-containing heteroring, which may be further substituted, and optionally one or more co-ligands. Preferably the co-ligand is absent in the complex.

In particular, the invention concerns a dopant comprising a complex of formula (XX)

$$M(La)_n(Xb)_m \qquad (XX)$$

wherein

M is selected from Cu$^{2+}$, Pd$^{2+}$, Au$^{2+}$, Ag$^{2+}$, and V$^{2+}$;

n is an integer selected from 1, 2, 3 or 4;

m is an integer selected from 0, 1, 2, or 3;

La is a ligand independently selected from mono-, bi-, or tridentate ligands comprising a moiety independently selected from a moiety according to any one of formulae (XX-1) to (XX-69)

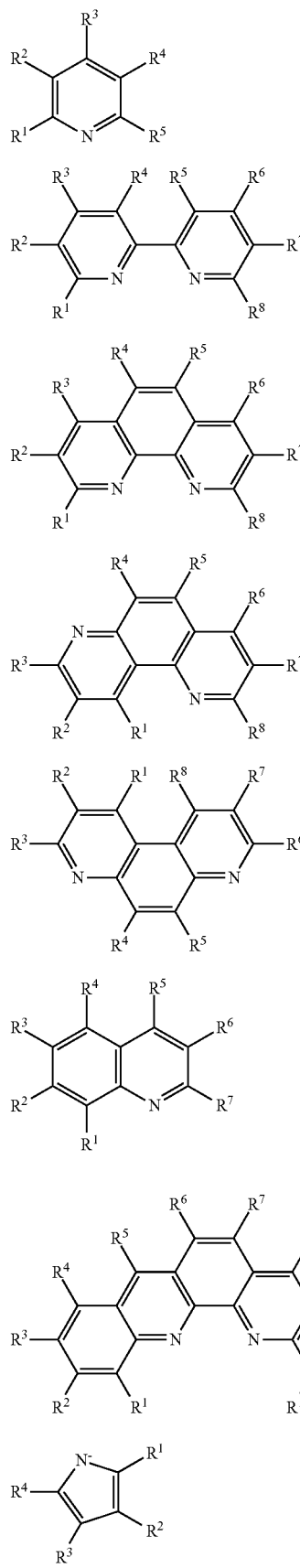

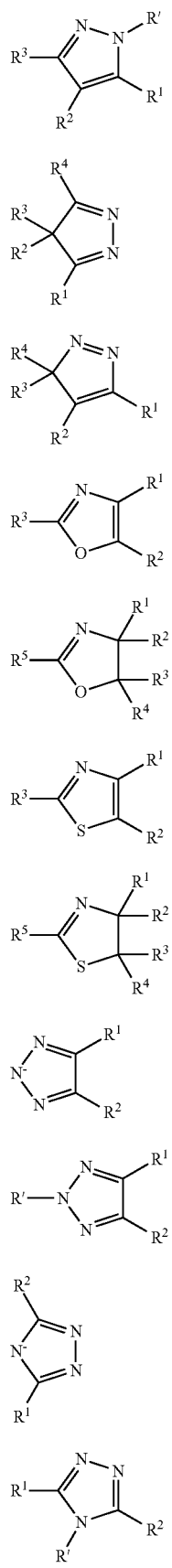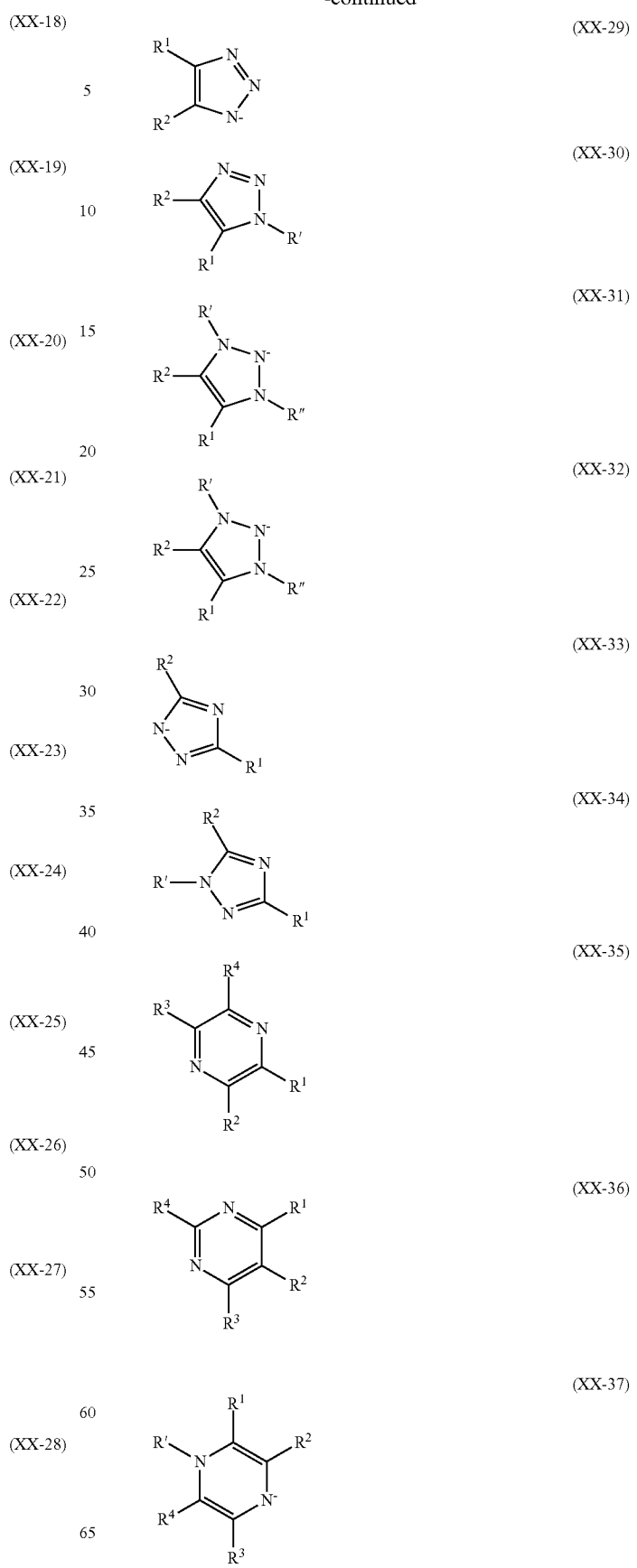

-continued (XX-38)

(XX-39)

(XX-40)

(XX-41)

(XX-42)

(XX-43)

(XX-44)

(XX-45)

-continued (XX-46)

(XX-47)

(XX-48)

(XX-49)

(XX-50)

(XX-51)

(XX-52)

-continued
(XX-53)
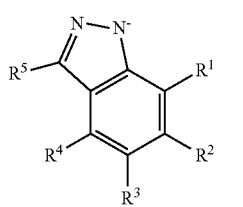
(XX-54)
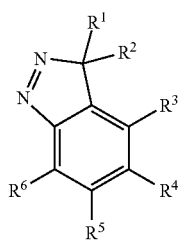
(XX-55)
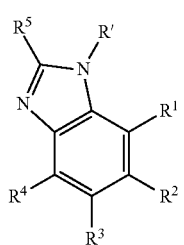
(XX-56)
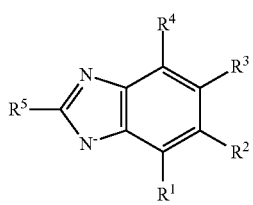
(XX-57)
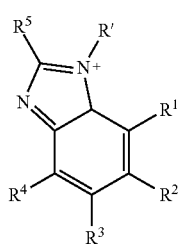
(XX-58)
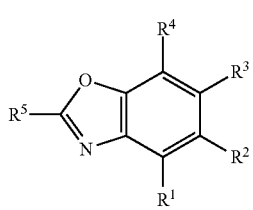
(XX-59)
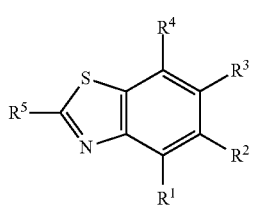
-continued
(XX-60)
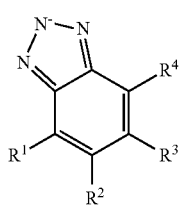
(XX-61)
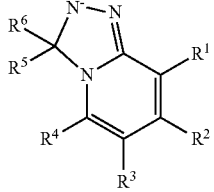
(XX-62)
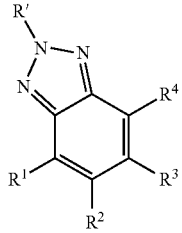
(XX-63)
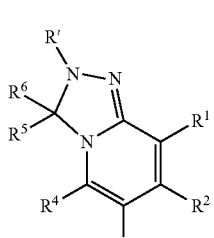
(XX-64)
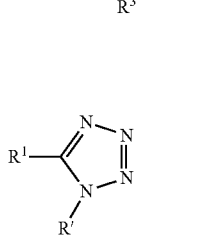
(XX-65)
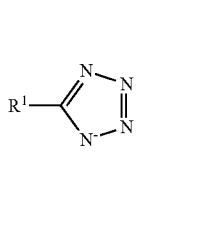
(XX-66)
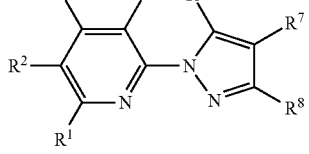

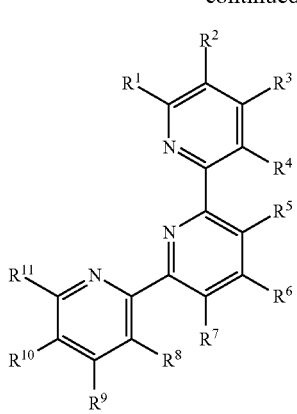

(XX-67)

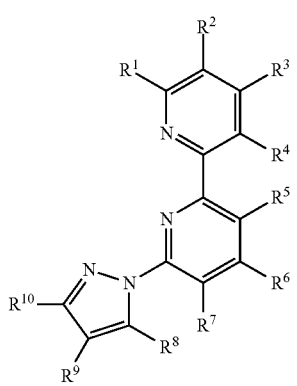

(XX-68)

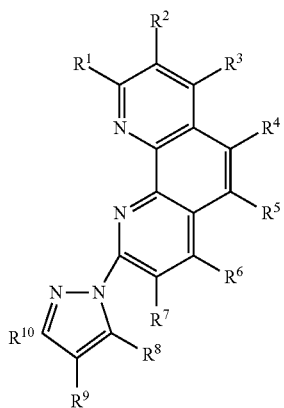

(XX-69)

wherein:

$R^1, R^2, R^3, R^4, R^5, R^6, R^7, R^8, R^9, R^{10}, R^{11}$ and $R^{12}$ of moieties (XX-1) to (XX-69) are independently selected from H, halogen, Cl⁻, Br⁻, I⁻, —NO$_2$, —OH, —NH$_2$, —COOH, —CN, —OCN⁻, isocyanate group, sulfonyl group and substituents comprising 1 to 40 carbons and 0 to 20 heteroatoms and/or groups selected from —O—, —C(O)—, —C(O)O—, —S—, —S(O)—, SO$_2$—, —S(O)$_2$O—, —N=, —P=, —NR$^{13}$—, —PR$^{13}$—, —P(O)(OR$^{13}$)—, —P(O)(OR$^{13}$)O—, —P(O)(NR$^{13}$R$^{13}$)—, —P(O)(NR$^{13}$R$^{13}$)O—, —P(O)(NR$^{13}$R$^{13}$)NR$^{13}$—, —S(O)NR$^{13}$—, and —S(O)$_2$NR$^{13}$—, with R$^{13}$ being independently selected from H, C1-C6 alkyl, C4-C20 aryl group, C4-C20 arylalkyl group and C4-C20 heteroaryl group, wherein the heteroatom is selected from N, S, or O, and said alkyl, arylalkyl and heteroaryl groups being optionally perfluorinated;

R' and R" are independently selected from —CH$_2$R$^1$, —CHR$^1$R$^2$ and —CR$^1$R$^2$R$^3$, R$^1$R$^2$ and R$^3$ being defined as above; and Xb is a monodentate co-ligand independently selected from H$_2$O, Cl⁻, Br⁻, I⁻, CN⁻, NCO⁻, NCS⁻, NCSe, NH$_3$, NR$_7$R$_8$R$_9$, or PR$_7$R$_8$R$_9$, wherein R$_7$, R$_8$, and R$_9$ are selected independently from substituted or unsubstituted C1-C20 alkyl, C2-C20 alkenyl, C2-C20 alkynyl, and C4 to C20 aryl.

The dopant of the invention may comprise one or more complexes of formula (XX), preferably one complex of formula (XX).

In an embodiment, the dopant is a complex of formula (XX).

The complex of formula (XX) may be charged or uncharged, depending on the charge of the ligand and the oxidation state of the metal. Preferably, the complex is cationic and is provided together with a suitable anionic species. The anion may be chosen according to the specific device or material, to which the complex is to be added. The anion may be chosen, for example in OLED applications, so as to limit migration of the complex, for example to another layer. Accordingly, the invention provides a salt comprising the complex of the invention and an anionic species. The anionic species may be an organic or an inorganic anion.

According to an embodiment, the complex of formula (XX) is under cationic form and provided with an anionic species independently selected from ClO$_4$⁻, PF$_6$⁻, BF$_4$⁻, [B(CN)$_4$]⁻, CF3SO$_3$⁻, [(CF$_3$SO$_2$)$_2$N]⁻ known as (TFSI), [B(C$_6$H$_3$(m-CF$_3$)$_2$)$_4$]⁻, [B(C$_6$F$_5$)$_4$]⁻, [B(C$_6$H$_5$)$_4$]⁻, [Al(OC(CF$_3$)$_3$)$_4$], or [CB$_{11}$H$_{12}$]⁻.

In an embodiment, the metal M of the complex of formula (XX) is Cu, preferably Cu(II) or Cu$^{2+}$.

n of the complex of formula (XX) represents the number of ligand La and is an integer from 1 to 4. The complex of formula (XX) may possibly contain up to 4 La ligands, provided that said ligands are monodentate ligands and that m representing the number of co-ligand Xb is 0. In the complex of formula (XX), the metal M is in a +2 oxidation state, the electronic configuration of metal has the coordination of 4 and can bind 4 donor atoms provided by La ligands or by a combination of La ligands and Xb co-ligands. The number of donor atoms provided by the La ligands in the complex of formula (XX) depends on the type of ligand, i.e. if the La ligands are selected from mono-, bi- or tridentate ligands or a combination of thereof, provided that the coordination number of the metal M is 4. The number of co-ligand Xb in the complex of formula (XX) being m depends on the number of "places" on the metal M unbound by donor atoms of La ligands.

According to an embodiment, n in the complex of formula (XX) is 2, 3 or 4. The number of co-ligand Xb, being m, depends on the number of "places" of the coordination number of the metal M unbound by donor atoms of La ligands.

Thus, according to an embodiment, the complex of formula (XX), provided that m is 0, is selected from a complex according to any one of formulae (XXIII) to (XXV)

M L1 L2 L3 L4       (XXIII), wherein L1, L2, L3 and L4 are selected from monodentate ligands,

M L1 L2 L3       (XXIV), wherein L1 and L2 are selected from monodentate ligands and L3 is selected from bidentate ligands,

M L1 L2       (XXV), wherein L1 and L2 are selected from bidentate ligands, or L1 is selected from monodentate ligands and L2 is selected from tridentate ligands;
wherein said mono-, bi-, or tridentate ligands are independently selected from La ligand.

Said La ligands are defined as above or in particular embodiment relative to the complex of formula (XX).

Provided that m is 1, the complex of formula (XX) is selected is selected from a complex according to any one of formulae (XXVI) to (XVIII)

M L1 L2 L3 X1    (XXVI), wherein L1, L2 and L3 are selected from monodentate ligands,

M L1 L2 X1    (XXVII), wherein L1 is selected from monodentate ligands and L2 is selected from bidentate ligands,

M L1 X1    (XVIII), wherein L1 is selected from tridentate ligands;
wherein said mono-, bi-, or tridentate ligands are independently selected from La ligand and X1 is selected from Xb monodentate co-ligands as defined for the complex of formula (XX).

Said La ligands and Xb are defined as above or in particular embodiment herein relative to the complex of formula (XX).

Provided that m is 2, the complex of formula (XX) is selected is selected from a complex according to any one of formulae (XXIX) to (XXX)

M L1 L2 X1 X2    (XXIX), wherein L1 and L2 are selected from monodentate ligands,

M L1 X1 X2    (XXX), wherein L1 is selected from bidentate ligands,
wherein said mono-, or bidentate ligands are independently selected from La ligand and X1 and X2 are selected from Xb monodentate co-ligands.

Said La ligands and Xb are defined as above or in particular embodiment herein relative to the complex of formula (XX).

Provided that m is 3, the complex of formula (XX) is selected is selected from a complex of formula (XXXI)

M L1 X1 X2 X3    (XXXI), wherein L1 is selected from monodentate ligands;
wherein said monodentate ligands is independently selected from La ligand and X1, X2, X3 are selected from Xb monodentate co-ligands.

Said La ligands and Xb are defined as above or in particular embodiment herein relative to the complex of formula (XX).

In a further embodiment, provided that n is ≥2, said La ligands of the complex of formula (XX) are identical or different from each other. Thus, when at least 2 La ligands are selected from monodentate ligands or bidentate ligands, each monodentate ligand or each bidentate ligand may be identical or different. Preferably said La ligands are identical.

According to a further embodiment, m is 0. The complex of the invention has only La ligands. Thus, wherein m is 0, the complex of formula (XX) may be selected from a complex of formula (XXa):

M(La)$_n$ wherein

M is selected from Cu$^{2+}$, Pd$^{2+}$, Au$^{2+}$, Ag$^{2+}$, and V$^{2+}$; preferably Cu$^{2+}$;

n is an integer selected from 1, 2, 3 or 4;

La is a ligand independently selected from mono-, bi-, or tridentate ligands comprising a moiety independently selected from a moiety according to any one of formulae (1) to (65), as defined above.

In the complex of formula (XX), La is a ligand independently selected from mono-, bi-, or tridentate ligands comprising a moiety independently selected from a moiety according to any one of formulae (XX-1) to (XX-69).

In a preferred embodiment of the complex of formula (XX), La is a ligand is selected from a moiety according to any one of formulae (XX-1)-(XX-7) and (XX-66) to (XX_69), preferably (XX-1)-(XX-7).

In particular, La ligand of the complex of formula (XX) may be selected from a moiety according to any one of formulae (XX-81) to (XX-92)

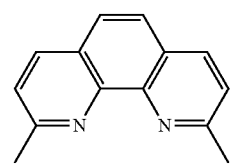
(XX-81)

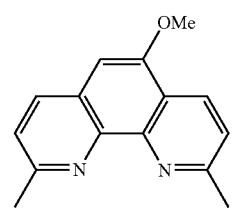
(XX-82)

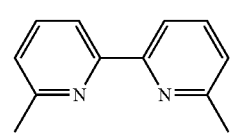
(XX-83)

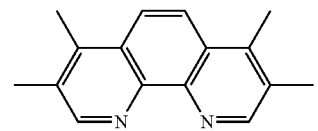
(XX-84)

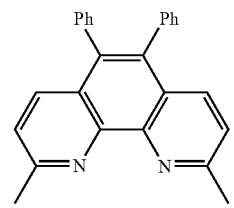
(XX-85)

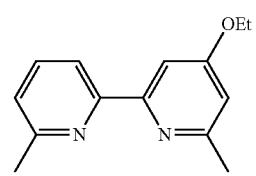
(XX-86)

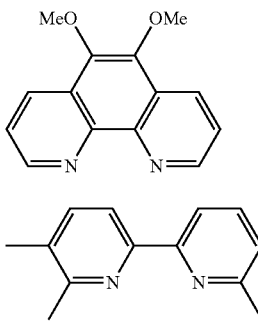
(XX-87)

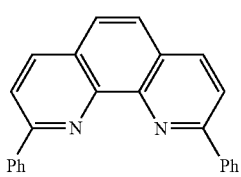
(XX-88)

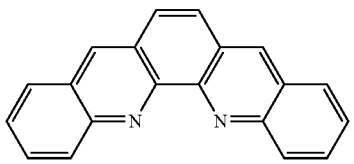
(XX-89)

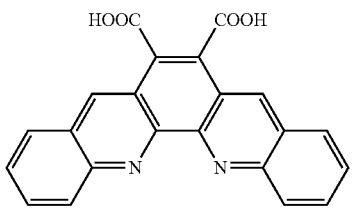
(XX-90)

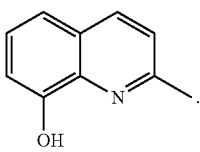
(XX-91)

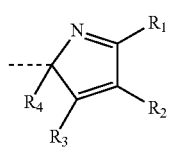
(XX-92)

In a preferred embodiment, La of the complex of formula (XX) is a ligand selected from bi-dentate ligands independently selected from a moiety according to any one of formulae (XX-1) to (XX-69) as defined above. In particular, La ligands of the complex of formula (XX) are selected from bidentate ligands independently selected from a moiety according to any one of formulae (XX-2) to (XX-7). Since n is 2, said La ligands may be identical or different and may be identically substituted or differently substituted.

Accordingly, the complex of formula (XX) is selected from a complex according to any one of formulae (XXI) and (XXII)

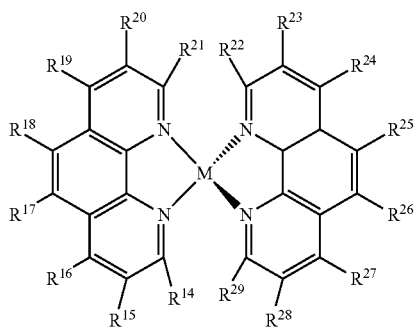
(XXI)

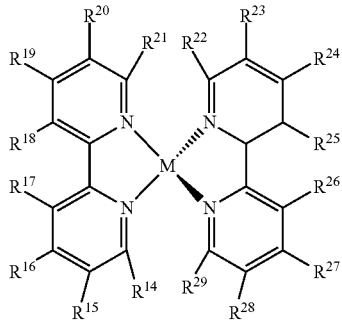
(XXII)

wherein, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$ of the complexes of formulae (XXI) and (XXII) are independently selected from H, halogen, Cl⁻, Br⁻, I⁻, —NO₂, —OH, —NH₂, —COOH, —CN, —OCN⁻, isocyanate group, sulfonyl group and substituents comprising 1 to 40 carbons and 0 to 20 heteroatoms and/or groups selected from —O—, —C(O)—, —C(O)O—, —S—, —S(O)—, SO₂—, —S(O)₂O—, —N═, —P═, —NR¹³—, —PR¹³—, —P(O)(OR¹³)—, —P(O)(OR¹³)O—, —P(O)(NR¹³R¹³)—, —P(O)(NR¹³R¹³)O—, —P(O)(NR¹³R¹³)NR¹³—, —S(O)NR¹³—, and —S(O)₂NR¹³, with R¹³ being independently selected from H, C1-C6 alkyl, C4-C20 aryl group, C4-C20 arylalkyl group and C4-C20 heteroaryl group, wherein the heteroatom is selected from N, S, O, said alkyl, arylalkyl and heteroaryl groups being optionally perfluorinated.

According to an embodiment, said substituents R¹, R², R³, R⁴, R⁵, R⁶, R⁷, R⁸, R⁹, R¹⁰, R¹¹ and R¹² of La ligand according to any one of moieties (XX-1) to (XX-69) and/or R¹⁴, R¹⁵, R¹⁶, R¹⁷, R¹⁸, R¹⁹, R²⁰, R²¹, R²², R²³, R²⁴, R²⁵, R²⁶, R²⁷, R²⁸ and R²⁹ of the complexes according to an one of formulae (XXI) and (XXII) are independently selected from H, halogen, Cl⁻, Br⁻, I⁻, —NO₂, —OH, —NH₂, —COOH, —CN, —OCN⁻, isocyanate group, sulfonyl group or a moiety according to any one of formulae (XXA-1) to (XXG-2):

(XXA-1)

-continued
(XXA-2)
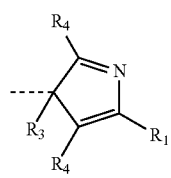
(XXA-3)
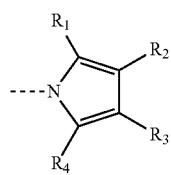
(XXA-4)
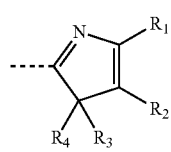
(XXA-5)
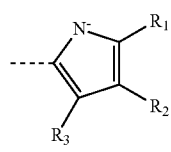
(XXA-6)
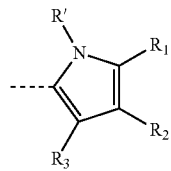
(XXB-1)
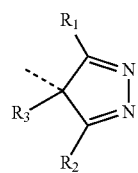
(XXB-2)
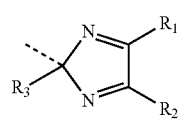
(XXB-3)
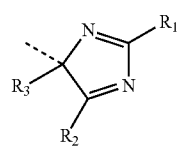
(XXB-4)
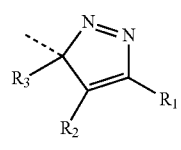
(XXB-5)
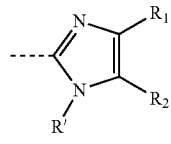
-continued
(XXB-6)
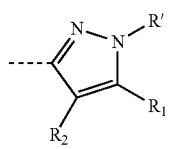
(XXB-7)
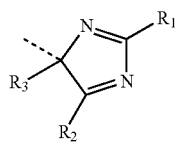
(XXB-8)
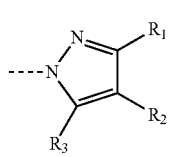
(XXB-9)
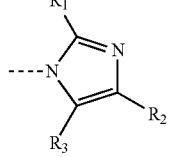
(XXB-10)
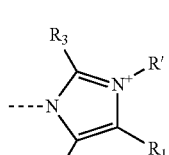
(XXB-11)
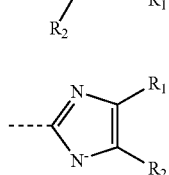
(XXB-12)
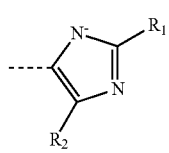
(XXB-13)
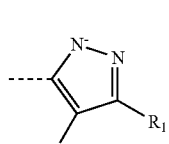
(XXB-14)
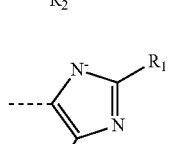
(XXB-15)
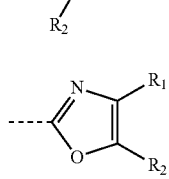

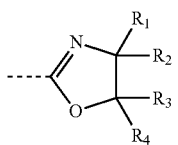 (XXB-16)
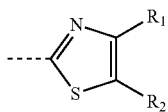 (XXB-17)
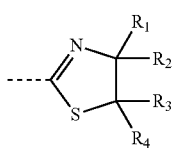 (XXB-18)
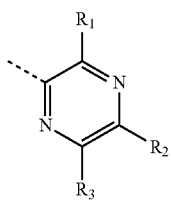 (XXB-21)
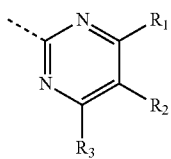 (XXB-22)
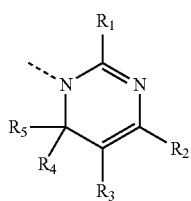 (XXB-23)
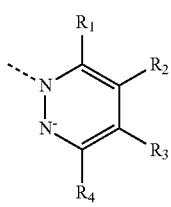 (XXB-24)
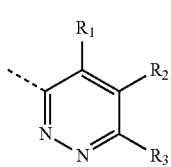 (XXB-25)
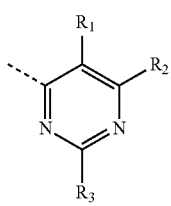 (XXB-26)
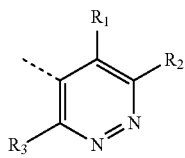 (XXB-27)
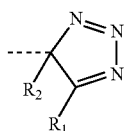 (XXC-1)
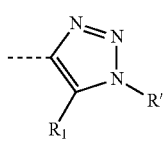 (XXC-2)
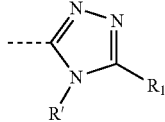 (XXC-3)
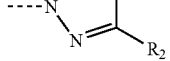 (XXC-4)
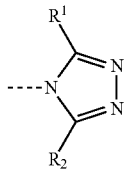 (XXC-5)
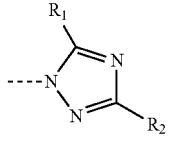 (XXC-6)
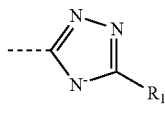 (XXC-7)
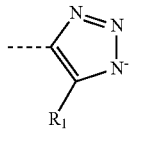 (XXC-8)
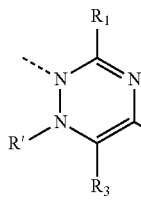 (XXC-9)

(XXC-10) 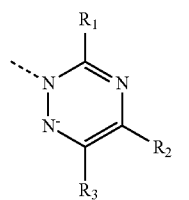
(XXC-11) 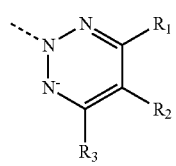
(XXC-12) 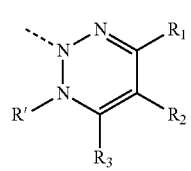
(XXC-13) 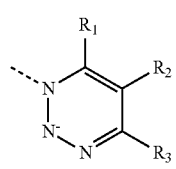
(XXC-14) 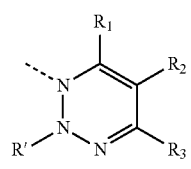
(XXC-15) 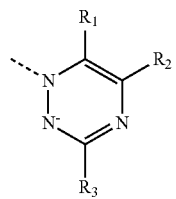
(XXC-16) 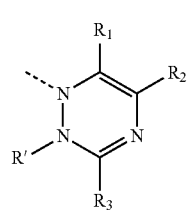
(XXC-17) 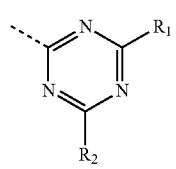
(XXC-18) 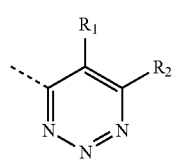
(XXC-19) 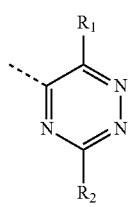
(XXC-20) 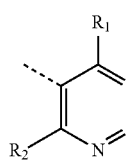
(XXC-21) 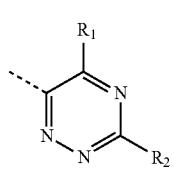
(XXC-22) 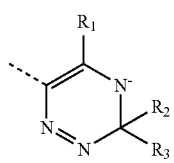
(XXC-23) 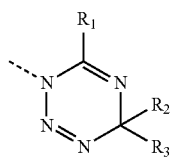
(XXC-24) 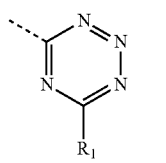
(XXC-25) 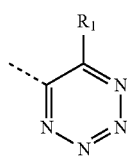
(XXC-26) 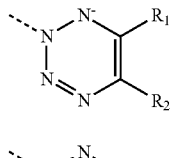
(XXC-27)
(XXD-1) 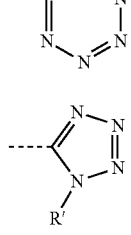

-continued
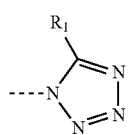
(XXD-2)
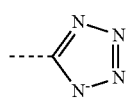
(XXD-3)
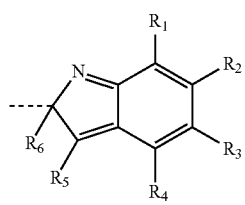
(XXE-1)
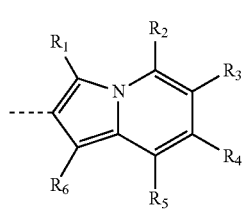
(XXE-2)
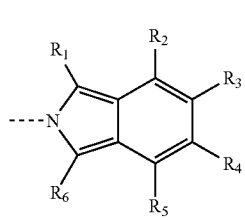
(XXE-3)
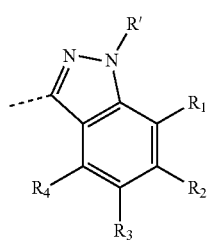
(XXF-1)
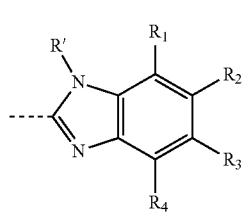
(XXF-2)
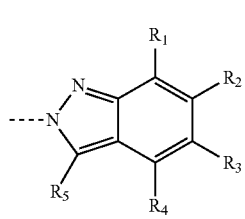
(XXF-3)
-continued
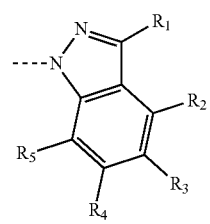
(XXF-4)
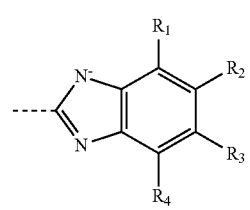
(XXF-5)
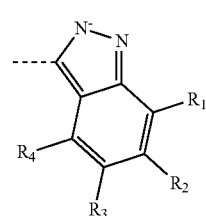
(XXF-6)
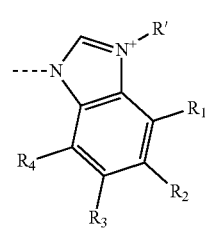
(XXF-7)
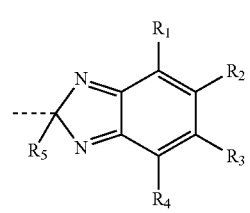
(XXF-8)
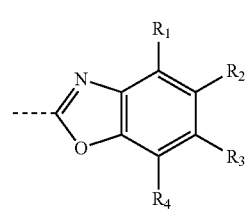
(XXF-9)
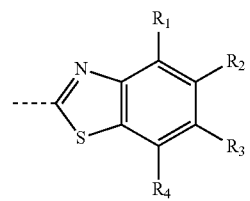
(XXF-10)

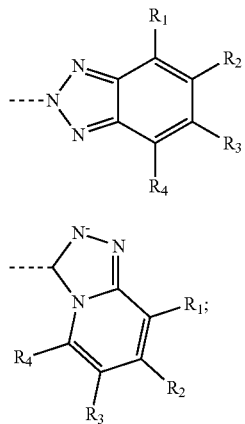

wherein:
the dotted line represents the bond connecting the substituent of (XXA-1) to (XXG-2) on the ligand La according to any one of formulae (XX-1)-(XX-69) or on to the complex according to any one of formulae (XXI) and (XXII); and, $R_1$, $R_2$, $R_3$, $R_4$, $R_5$, and $R_6$ of moieties (XXA-1) to (XXG-2) are independently selected from H, halogen, Cl⁻, Br⁻, I⁻, —NO$_2$, —OH, —NH$_2$, —COOH, —CN, —OCN⁻, isocyanate group, sulfonyl group and substituents comprising 1 to 40 carbons and 0 to 20 heteroatoms and/or groups selected from —O—, —C(O)—, —C(O)O—, —S—, —S(O)—, SO$_2$—, —S(O)$_2$O—, —N═, —P═, —NR$^{13}$—, —PR$^{13}$—, —P(O)(OR$^{13}$)—, —P(O)(OR$^{13}$)O—, —P(O)(NR$^{13}$R$^{13}$)—, —P(O)(NR$^{13}$R$^{13}$)O—, —P(O)(NR$^{13}$R$^{13}$)NR$^{13}$—, —S(O)NR$^{13}$—, and —S(O)$_2$NR$^{13}$, with R$^{13}$ being independently selected from H, C1-C6 alkyl, C4-C20 aryl group, C4-C20 arylalkyl group and C4-C20 heteroaryl group, said alkyl, arylalkyl and heteroaryl groups being optionally perfluorinated.

Accordingly, e.g., a La ligand may be a bidentate ligand comprising a moiety selected from formula (XX-1) being substituted by a moiety of formula (XXA-1), the combination of the moieties providing a bidentate ligand. Several combinations between La ligand comprising a moiety according to any one of formula (XX-1) to (XX-69) and at least one of the La ligand being substituted by at least one moiety selected in the moiety according to any one of formulae (XXA-1) to (XXG-2) may provide tridentate ligands or bidentate ligands, which may be used in a complex of the invention according to an embodiment of the invention and provided that the coordination number of the metal M is 4.

In an embodiment, R$^{14}$, R$^{21}$, R$^{22}$ and R$^{29}$ of the complexes according to any one of formulae (XXI) and (XXII) are not H and are independently selected from halogen, Cl⁻, Br⁻, I⁻, —NO$_2$, —OH, —NH$_2$, —COOH, —CN, —OCN⁻, isocyanate group, sulfonyl group and substituents comprising 1 to 40 carbons and 0 to 20 heteroatoms and/or groups selected from —O—, —C(O)—, —C(O)O—, —S—, —S(O)—, SO$_2$—, —S(O)$_2$O—, —N═, —P═, —NR$^{13}$—, —PR$^{13}$—, —P(O)(OR$^{13}$)—, —P(O)(OR$^{13}$)O—, —P(O)(NR$^{13}$R$^{13}$)—, —P(O)(NR$^{13}$R$^{13}$)O—, —P(O)(NR$^{13}$R$^{13}$)NR$^{13}$—, —S(O)NR$^{13}$—, and —S(O)$_2$NR$^{13}$, with R$^{13}$ being independently selected from H, C1-C6 alkyl, C4-C20 aryl group, C4-C20 arylalkyl group and C4-C20 heteroaryl group, wherein the heteroatom is selected from N, S, O, said alkyl, arylalkyl and heteroaryl groups being optionally perfluorinated. Preferably R$^{14}$, R$^{21}$, R$^{22}$ and R$^{29}$ of the complexes according to any one of formulae (XXI) and (XXII) are not H and are independently selected from C1-C6 alkyl, C1-C6 heteroalkyl, C4-C20 aryl group, C4-C20 arylalkyl group and C4-C20 heteroaryl group, wherein the heteroatom is selected from N, S, O, said alkyl, heteroalkyl, arylalkyl and heteroaryl groups being optionally perfluorinated. Preferably, R$^{15}$ to R$^{20}$ and R$^{23}$ to R$^{28}$ of the complexes according to any one of formulae (XXI) and (XXII) are independently selected from H, halogen, Cl⁻, Br⁻, I⁻, —NO$_2$, —OH, —NH$_2$, —COOH, —CN, —OCN⁻, isocyanate group, sulfonyl group, from C1-C6 alkyl, C1-C6 heteroalkyl, C4-C20 aryl group, C4-C20 arylalkyl group and C4-C20 heteroaryl group, wherein the heteroatom is selected from N, S, O, said alkyl, heteroalkyl, arylalkyl and heteroaryl groups being optionally perfluorinated, and from a moiety according to any one of formulae (XXA-1) to (XXG-2) as defined above.

R$^{15}$ to R$^{20}$ and R$^{23}$ to R$^{28}$ of the complexes according to any one of formulae (XXI) and (XXII) are independently selected from H, halogen, Cl⁻, Br⁻, I⁻, —NO$_2$, —OH, —NH$_2$, —COOH, —CN, —OCN⁻, isocyanate group, sulfonyl group, from C1-C6 alkyl, C1-C6 heteroalkyl, C4-C20 aryl group.

Substituents comprising 1 to 40 carbons and 0 to 20 heteroatoms, alkyl, heteroalkyl, aryl group, arylalkyl group and heteroaryl group, heteroaryl groups of R$^1$ to R$^{12}$ of La Ligand according to any one of moieties (XX-1) to (XX-69), of R$^{14}$ to R$^{29}$ of the complexes according to any one of formulae (XXI) and (XXII), of R$_1$ to R$_6$, of moieties according to any one of formulae (XXA-1) to (XXG-2) and of R$_7$ to R$_9$ of Xb of the complex of formula (XX) are selected from hydrocarbon, hydrocarbyl, heterocarbon or heterocarbyl groups containing from 1 to 40 carbons, 1 to 20 carbons, 1 to 12 carbons, 1 to 9 carbons, 1 to 6 carbons, 4 to 20 carbons, 4 to 12 carbons, or 4 to 9 carbons, and may contain 0-20 heteroatom being selected from N, S, O, or P, and 0-1 halogen being selected from Cl, F, Br or I, said hydrocarbon, hydrocarbyl, heterocarbon or heterocarbyl groups being optionally perfluorinated and, if they comprise 3 or more carbons, they may be linear, branched or cyclic, preferably linear or branched.

In particular R$^1$ to R$^{12}$ of La Ligand according to any one of moieties (XX-1) to (XX-69) are independently selected from H, halogen, Cl⁻, Br⁻, I⁻, —NO$_2$, —OH, —NH$_2$, —COOH, —CN, —OCN⁻, isocyanate group, sulfonyl group, from C1-C6 alkyl, C1-C6 heteroalkyl, C4-C20 aryl group, C4-C20 arylalkyl group and C4-C20 heteroaryl group, wherein heteroatom is selected from N, S, or O, said alkyl, heteroalkyl, arylalkyl and heteroaryl groups being optionally perfluorinated, and from a moiety according to any one of formulae (XXA-1) to (XXG-2) as defined above.

R$^1$ to R$^{12}$ of La Ligand according to any one of moieties (XX-1) to (XX-69) may be independently selected from H, halogen, Cl⁻, Br⁻, I⁻, —NO$_2$, —OH, —NH$_2$, —COOH, —CN, —OCN⁻, isocyanate group, sulfonyl group, from C1-C6 alkyl, C1-C6 heteroalkyl, C4-C20 aryl group.

In particular R$_1$ to R$_6$ of moieties according to any one of formulae (XXA-1) to (XXG-2) are independently selected from H, halogen, Cl⁻, Br⁻, I⁻, —NO$_2$, —OH, —NH$_2$, —COOH, —CN, —OCN⁻, isocyanate group, sulfonyl group, from C1-C6 alkyl, C1-C6 heteroalkyl, C4-C20 aryl group, C4-C20 arylalkyl group and C4-C20 heteroaryl group, wherein heteroatom is selected from N, S, or O, said alkyl, heteroalkyl, arylalkyl and heteroaryl groups being optionally perfluorinated. Preferably R$_1$ to R$_6$ according to any one of formulae (XXA-1) to (XXG-2) are independently selected from H, halogen, Cl−, Br−, I−, —NO$_2$, —OH, —NH$_2$, —COOH, —CN, —OCN−, isocyanate group, sulfonyl group, from C1-C6 alkyl, C1-C6 heteroalkyl, C4-C20 aryl group.

According to an embodiment, $R_1$ to $R_6$ according to any one of formulae (XXA-1) to (XXG-2) are selected independently from H, halogen, C1-C6 linear alkyl, C3-C6 branched or cyclic alkyl, and —C≡N, wherein any one of said linear, branched or cyclic alkyl may be totally or partially halogenated, and may in particular also be —CF$_3$.

Other ligands of the complex of the invention, in particular ligands Xb (X1, . . . , Xm) of the complex of formula (XX), may, for example, be selected from: H$_2$O, Cl−, Br−, I−, CN−, NCO−, NCS−, NCSe−, NH$_3$, CO, PR$_3$, R being independently selected from substituted and unsubstituted C6-C18, preferably C6-C12, aryl or aryloxy group substituted and unsubstituted C1-C18, preferably C1-10, more preferably C1-C4 alkyl and/or alkoxyl; imidazole, substituted imidazoles; pyridines, substituted pyridines; pyrazoles, substituted pyrazoles; triazoles; pyrazine; for example. Preferably, the ligands Xb (X1, . . . , Xm) are selected from H$_2$O, Cl−, Br−, I−, CN−, NCO−, NCS−, NCSe−, NH$_3$, CO, and PR$_3$, R being preferably independently selected from phenyl, phenoxyl, alkyl and alkoxyl.

Figure 17A:
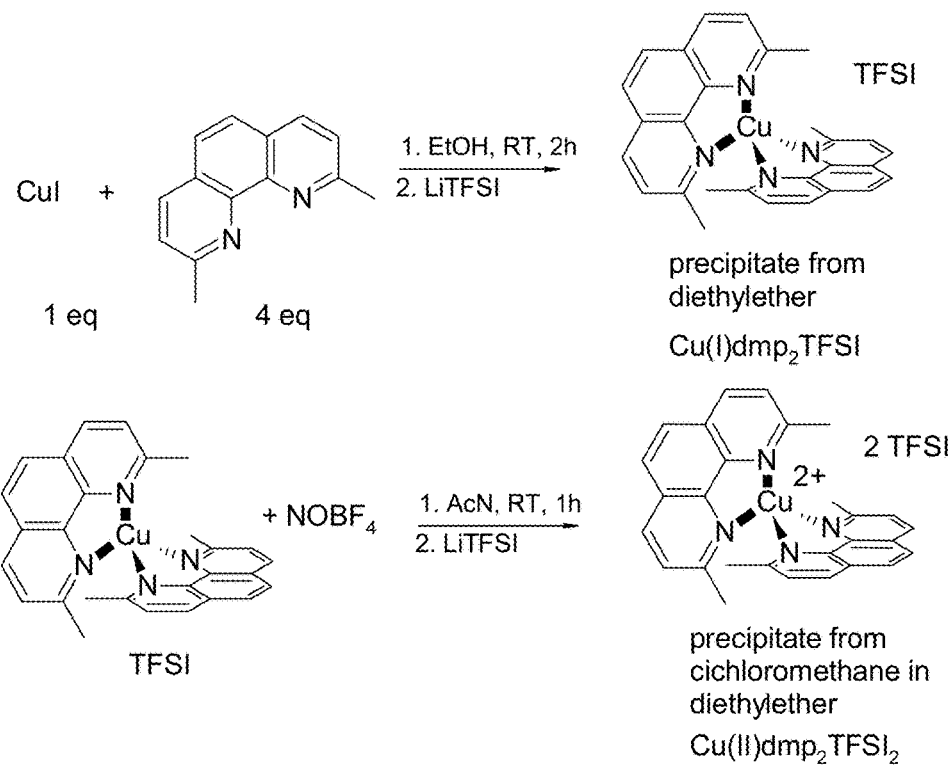
FIG. 17A shows the synthesis of copper (I/II) 2,2'-dimethyl 1,10-phenanthroline trifluoromethanesulfonimide (Cu(I/II)(dmp)$_2$TFSI$_{1/2}$).
Figure 17B:
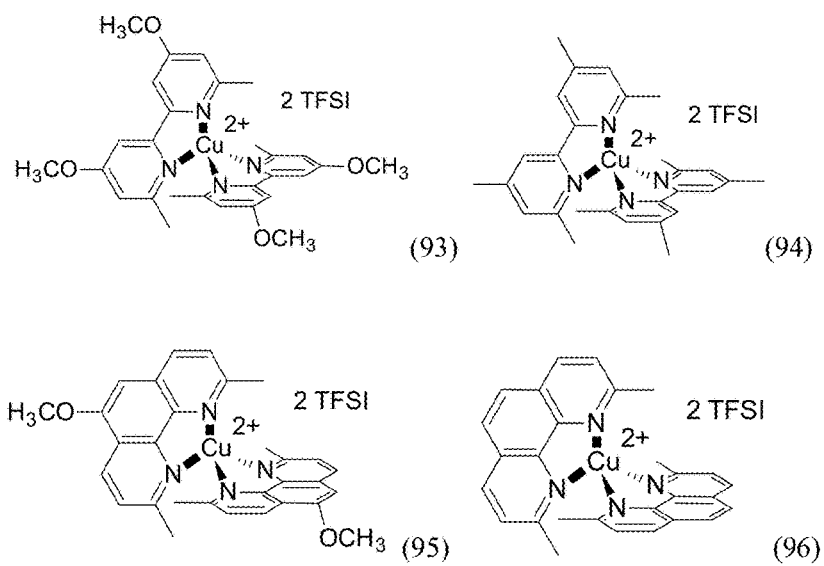
FIG. 17B shows (Cu(II)(tmbpy)$_2$(TFSI)$_2$) complexes of formulae (93) to (96), respectively.
Figure 18A:
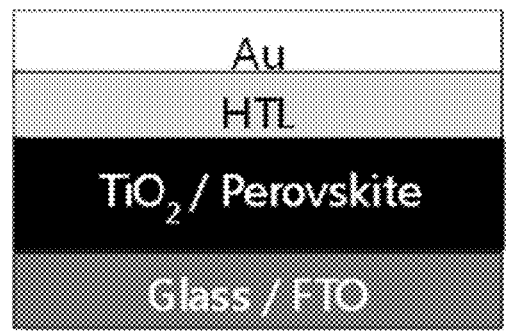
FIG. 18A shows the architecture of a perovskite solar cell as exemplified.
Figure 18B:
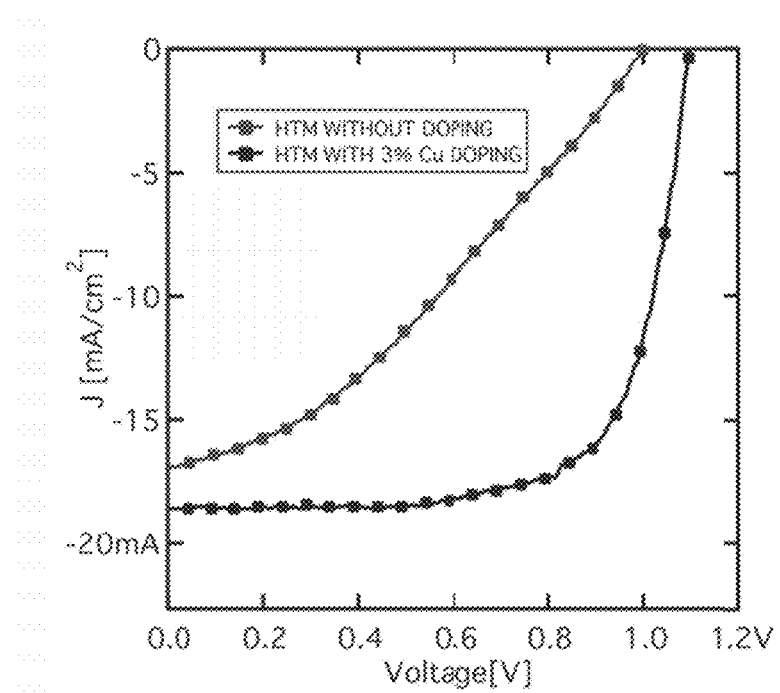
FIG. 18B shows J-V curves of perovskite solar cells without and with copper (II) 2,2'-dimethyl 1,10-phenanthroline trifluoromethanesulfonimide complex as dopant in the HTL (hole transport layer). The top curve (grey) shows J-V characteristic of a perovskite solar cell without copper (II) 2,2'-dimethyl 1,10-phenanthroline trifluoromethanesulfonimide (Cu(II)(dmp)$_2$(TFSI)$_2$ complex as dopant, the bottom curve showing J-V characteristic of a perovskite solar cell having spiro-OMeTAD with 3% (Cu(II)(dmp)$_2$(TFSI)$_2$ complex as dopant.

The complex of the invention may be synthesized from commercially available starting material at room temperature conditions (see FIG. 17).

In an embodiment, the dopant of the invention is a dopant for organic charge transporting material comprising at least one complex of the invention, in particular of formula (XX) and in more particular of the complexes (XXI) or (XXII) of the invention. The dopant of the invention may be a p-dopant or a n-dopant, preferably a p-dopant or a dopant for doping organic charge transporting material, preferably a dopant for doping HTM.

The properties of the dopant of the invention may be dependent upon its distorted tetragonal geometry. This may for example imply that the structural change between the different redox states of the metal complexes, e.g. between M (I) and M (II), is minimized.

The dopant of the present invention may be applied in doping the organic charge transporting material, in particular the hole transport materials (HTMs) to enhance their hole mobility, conductivity, as well as high thermal and electrochemical stability, resulting in enhancing the device performance and durability. These characteristics provide advantages in the development of efficient and (e.g. organic) electronic devices with high efficiency and at low cost.

The complex according to any one of formulae (XX), (XXI) and (XXII) may be used as a dopant for doping an organic semiconductor, a charge injection layer, a hole blocker layer, an electrode material, a transport material, a hole transport layer, a memory material, or combinations comprising two or more of the aforementioned. The complex of the invention may be also use for increasing one or more selected from conductivity, charge density and/or charge mobility of an organic charge transporting material. Said complex increases the conductivity of an organic semiconductor. The complex of according to any one of formulae (XX), (XXI) and (XXII) may be an additive of the organic semiconductor.

In particular, the complexes according to any one of formulae (XX), (XXI) and (XXII) may also be used to increase charge mobility and/or charge density in organic charge transporting materials, for example in organic semiconductors. While using negatively charged ligands (e.g. La and/or Xb) in the complex of the invention, neutral complexes may be obtained, which may be applied by an evaporation process as disclosed in WO 2005/036667. Doped layers may be produced by mixed evaporation of a matrix (for example a charge transporting material) and the dopant.

In an embodiment, the dopant comprising a complex according to any one of formulae (XX), (XXI) and (XXII) is deposited by solution processing, vapor deposition, screen-printing, spin coating or by evaporation.

In an aspect, the invention provides a complex according to any one of formulae (XX), (XXI) and (XXII) as an overvoltage protection agent.

The complex according to any one of formulae (XX), (XXI) and (XXII) is useful to improve charge collection and or charge transfer at interfaces. Accordingly, the invention also provides a method for increasing the conductivity of an organic semiconductor, the method comprising the step of adding, to said semiconductor, the complex of the invention.

The invention provides an electrochemical device comprising the complex of the invention. In particular, the complex is used as a redox-couple and/or as a dopant in such devices, or in accordance with the other uses specified elsewhere in this specification. Preferably, the invention provides an electrochemical device comprising an organic charge transport material comprising the complex of the invention.

According to an embodiment, the invention provides an electrochemical device, preferably a photoelectrochemical device comprising the complex of the invention.

According to an embodiment, the electrochemical device of the invention is selected from a photovoltaic cell, a battery, a rechargeable battery (for example a lithium ion battery), a light emitting device, an electrochromic device, a photo-electrochromic device, an electrochemical sensor, a biosensor, an electrochemical display and an electrochemical capacitor, (for example a double layer capacitor and/or a super capacitor).

According to an embodiment, the device is a battery, for example a lithium ion battery. Complexes of the invention may, for example, be used as redox couples in such devices. The complexes of the invention may also or specifically as redox couples be used to prevent over-charging and/or over-discharging in rechargeable batteries. Wang et al., "A new strategy of molecular overcharge protection shuttles for lithium ion batteries", Electrochem. Commun., 10 (2008) 651-654 discloses the use of redox-shuttle additives in the electrolyte or embedded in a separator between the electrolyte and an electrode, and their use for preventing overcharging and/or over-discharging of the devices. The complexes of the invention may be used in the same way, as additives to the electrolyte or in the separator, for example. As Wang et al. (2008) disclose, the oxidation potential of the redox couples is either preferably higher than the redox potential of the cathode material ("p-type shuttle"), or lower than the material of the anode material ("n-type shuttle"). In these devices, the redox couple provide an internal shunt, which prevents deterioration of the cell by imposing a limit on cell potential. The complexes of the invention may be used as both, n- or p-type shuttles (see above: D+/D, D/D−)) in rechargeable batteries, in particular lithium ion batteries. Further background with respect to over-charge and over-discharge protection in lithium-ion batteries is disclosed by S.-I. Nishimura et al. Nat. Mater., 7 (2008) 707-711. C. Buhrmester, J. Electrochem. Soc. 153 (2) A288-A294 (2006).

According to an embodiment, the device of the invention is a photoelectrochemical device. The photoelectrochemical device may, for example, may be selected from a dye sensitized solar cell (DSC), in particular a solid state DSC (ssDSC), an electrochromic device, a photo-electrochromic device and an organic light emitting diode (OLED) comprising the complex of the invention.

According to an embodiment, the device of the invention is an OLED. WO 2005/036667 discloses OLEDs that comprise ruthenium complexes for doping organic semiconductors. The complexes of the invention may used in the same manner. In particular, the complexes of the invention may also be used to increase charge mobility and/or charge density in organic charge transporting materials, for example in organic semiconductors. While using negatively charged ligands (e.g. La and Xb) in the complex of the invention, neutral complexes may be obtained, which may be applied by an evaporation process as disclosed in WO 2005/036667. Doped layers may be produces by mixed evaporation of a matrix (for example a charge transporting material) and the dopant.

US 2006/0250076 discloses OLEDs comprising doped charge carrier transport layers. The complexes of the invention may thus be used in OLEDs, in particular as dopants in charge carrier transport layers and/or in layers comprising organic charge transport material.

More preferably, the invention provides a dye-sensitized solar cell (DSC), most preferably a solid state dye-sensitized solar cell (ssDSC). According to an embodiment, the invention provides a solar cell comprising a layer comprising a doped organic charge transport material in accordance with the invention.

The electrochemical device of the invention, in particular the DSC is preferably a regenerative device.

Electrochemical devices generally comprise two electrodes and one or more layer between the electrodes. The electrochemical device of the invention preferably comprises a layer comprising an organic charge transport material and the complex of the invention.

Figure 14:
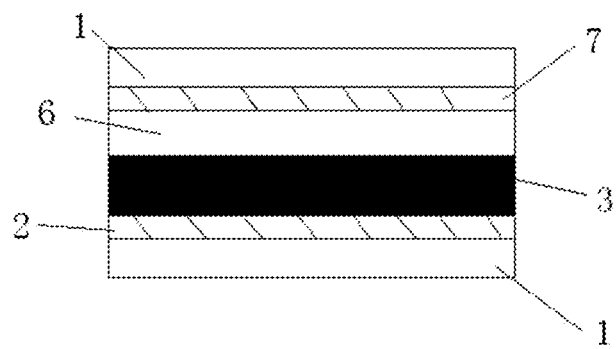
FIG. 14 is a schematic representation of a DSC according to the invention.
Figure 15:
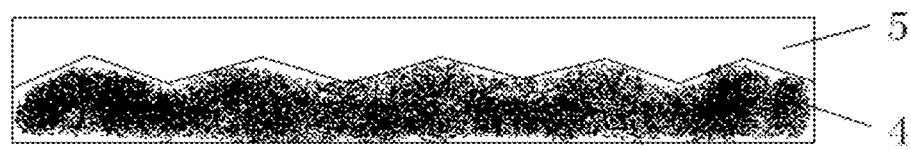
FIG. 15 is a schematic representation of the said light adsorption layer 3 of the dive shown in FIG. 14.

In the figures, FIG. 14 schematically shows a dye-sensitized solar cell.

The device of the present invention comprises at least one substrate 1. Contrary to the device shown in FIG. 14, the present invention also encompasses devices having only one substrate 1, for example only a top or only a bottom substrate 1, as is shown more specifically in FIG. 16. Preferably, there is a substrate facing the side of the device intended to be exposed to electromagnetic radiation for production of electrical current. The substrate facing radiation is preferably transparent. Transparency, for the purpose of the present invention, generally means that the respective structure (for example substrate, counter electrode, conductive layer, porous semiconductor) is transparent to at least some visible light, infrared light or UV light, in order to convert this light to electrical energy in the device of the invention. Preferably, transparent means transparent to all visible light, more preferably also to some of the near infra-red and/or also to at least part of the ultraviolet light spectrum.

The substrate 1 may be made from plastic or from glass. In flexible devices, the substrate 1 is preferably made from plastic. In an embodiment, the substrate comprises a plastic selected from the groups of polyethylene terephthalate, polyethylene naphthalate, polycarbonate, polypropylene, polyimide, 3-acetyl cellulose, and polyethersulfone, for example.

Figure 16:
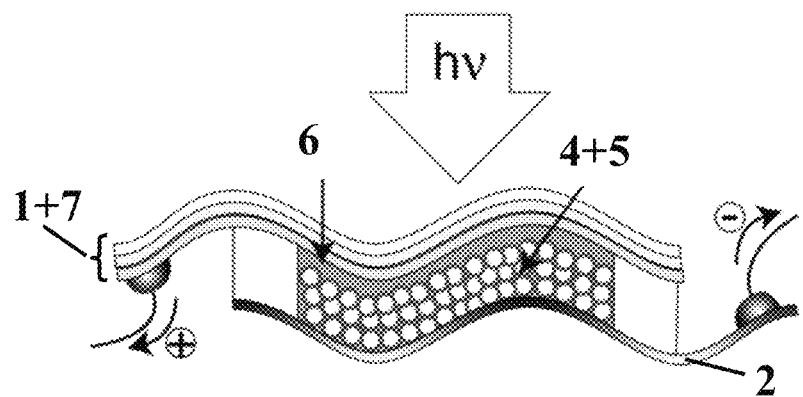
FIG. 16 is a schematic representation of an embodiment of a flexible conversion device of the present invention.

The conversion devices of the present invention generally have two conductive layers 2 and 7, wherein a first conductive layer 2 is required for removing the electrons generated from the device, and a second conductive layer 7 for supplying new electrons, or, in other words, removing holes. This is illustrated in FIG. 16 by the signs + and −. The conductive layers 2 and 7 may be provided in many different forms and may be made from various materials, depending on the purpose or nature of the device.

The second conductive layer 7 may be part of the substrate 1, as is the case, for example with ITO (indium tin oxide)-coated plastic or glass, where the transparent ITO is coated on the plastic or glass and makes the later electrically conductive.

Accordingly, one or both conductive layers 2 and 7 may comprise a transparent metal oxide, such as indium doped tin oxide (ITO), fluorine doped tinoxide (FTO), ZnO—$Ga_2O_3$, ZnO—$Al_2O_3$, tin-oxide, antimony doped tin oxide (ATO) and zinc oxide.

According to embodiments of the invention, only the first conductive layer 2 or only the second conductive layer 7 comprises a transparent metal oxide layer as defined above. It is also possible to provide one or both of the two opposed conductive layers 2 and 7 in the form of a conductive foil, for example a metal foil, in particular a titanium foil or zinc foil. This is preferred, for example, in some flexible devices, as detailed below. Preferably, the first conductive layer 2, is made from a conductive metal foil, for example, as is shown in FIG. 16. Such a foil may not be transparent.

The device of the present invention generally comprises a counter electrode 7, which faces an intermediate layer 6 towards the inside of the cell, and the substrate 1 on the outside of the cell, if such substrate is present. The counter electrode generally comprises a catalytically active material, suitable to provide electrons and/or fill holes towards the inside of the device. The counter electrode may thus comprises materials selected from material selected from Pt, Au, Ni, Cu, Ag, In, Ru, Pd, Rh, Ir, Os, C, conductive polymer and a combination of two or more of the aforementioned, for example. Conductive polymers may be selected from polymers comprising polyaniline, polypyrrole, polythiophene, polybenzene and acetylene, for example.

In FIG. 14, the second conductive layer can be considered as part of the counter electrode 7 or as part of the substrate 1 on the top of the device, and is thus not separately shown. If the second conductive layer is considered to be part of the substrate 1, such substrate could be plastic or glass coated with ITO or other materials, as mentioned above, for example.

In FIG. 14, layer 3 is a light absorption layer, which comprises actually at least two separate layers, namely a porous semiconductor layer 4 and, absorbed thereon, a sensitizer layer 5. The sensitizer layer may comprise one or more of the group consisting of: organo-metallic sensitizing compounds, metal free organic sensitizing compounds, inorganic sensitizing compounds such as quantum dots, Sb2S3 (Antimonysulfide, for example in the form of thin films), and combinations of the aforementioned.

The sensitizer may, for example, comprise sensitising dyes 5. If the sensitizer layer 5 comprises a dye, it generally comprises, besides optional co-adsorbed compounds, such as those disclosed in WO2004/097871A1, for example, at least one dye or sensitizer, or a combination of two or more different sensitizers. Examples for organometallic compounds encompass ruthenium dyes, as they are currently used in such devices. Suitable ruthenium dyes are disclosed, for example, in WO2006/010290.

The dye layer may comprise organic sensitizers. For example, the device may be free of any sensitizer using ruthenium or another noble metal.

The porous semiconductor layer may be produced by processes described in the art (B. O'Reagan and M. Grätzel, Nature, 1991, 353, 373) from semiconductor nanoparticles, in particular nanocrystalline particles. Such particles generally have a mean diameter of about 0-50 nm, for example 5-50 nm. Such nanoparticles may be made from a material selected from the group of Si, $TiO_2$, $SnO_2$, ZnO, $WO_3$, $Nb_2O_5$ and $TiSrO_3$, for example. The constitution of the porous layers from nanocrystalline particles is clearly visible in the schematic FIG. 16, showing an embodiment of a flexible cell according to the invention.

The device of the present invention has a layer 6 having the general purpose of mediating the regeneration of electrons in the dye, which were removed due to radiation. These electrons are provided by the counter electrode 7, and layer 6 thus mediates the transport of electrons from the counter electrode to the dye, or of holes from the dye to the counter electrode. The transport of electrons and/or holes is preferably mediated by electrically conductive materials. Accordingly, the layer 6 is preferably an organic charge transport layer.

According to a preferred embodiment of the invention, this intermediate (or organic charge transport) layer 6 is substantially free of a solvent. This embodiment is particularly relevant with respect to flexible devices. Substantially free means, for the purpose of the present invention, that the layer comprises less than 10% by weight, more preferably less than 5 wt. %, even more preferably less than 1% and most none added solvent at all. In contrary to many prior art devices and in particular to flexible devices made from polymers, the fact that the intermediate layer is solvent free provides the important advantage that there is no degradation due to solvent evaporation through the one or two substrate layer(s) 1.

According to an embodiment, the organic charge transport layer 6 comprises an organic charge transport material and the complex of the invention.

According to an embodiment, the device of the present invention comprises at least one substrate layer 1, a conductive layer 2, a light absorption layer 3, a doped organic charge transport material layer 6, and a counter electrode 7, wherein said conductive layer 2, said light absorption layer 3, said organic charge transport layer 6 and said counter electrode 7 are connected in series. According to a preferred embodiment, the device comprises two transparent substrates 1, on the top and the bottom of the device, respectively. The top of the device corresponds to the top of the drawing in FIG. 14. The top corresponds to the side where the major part of light enters the device. The intermediate layer 6 comprises an organic charge transporting material comprising the complex of the invention and is provided between the dye layer 5 and the counter electrode 7.

According to another embodiment, the device of the present invention is a flexible device. Preferably, according to this embodiment, the device comprises a flexible substrate 1, a counter electrode 7, a charge transport layer 6, a dye layer 5, which may comprise organometallic dyes, organic dyes, or both, a porous semiconductor layer 4, and a conductive layer 2. Preferably, said layers are connected in series, for example in that order from the top to bottom.

Figure 5:
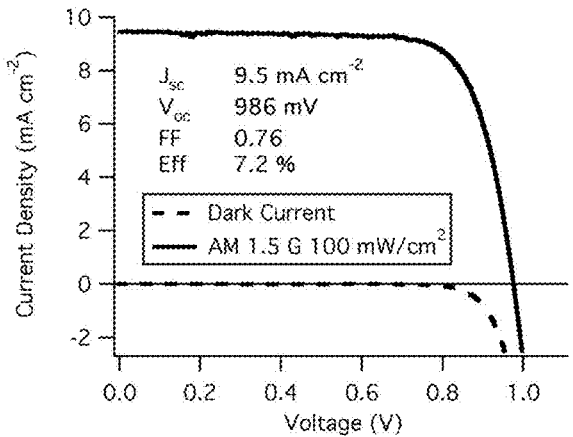
FIG. 5 shows J-V characteristics of a ssDSC according to a preferred embodiment of the invention, comprising 1.6% of complex 2 dopant.
Figures 1, 6:
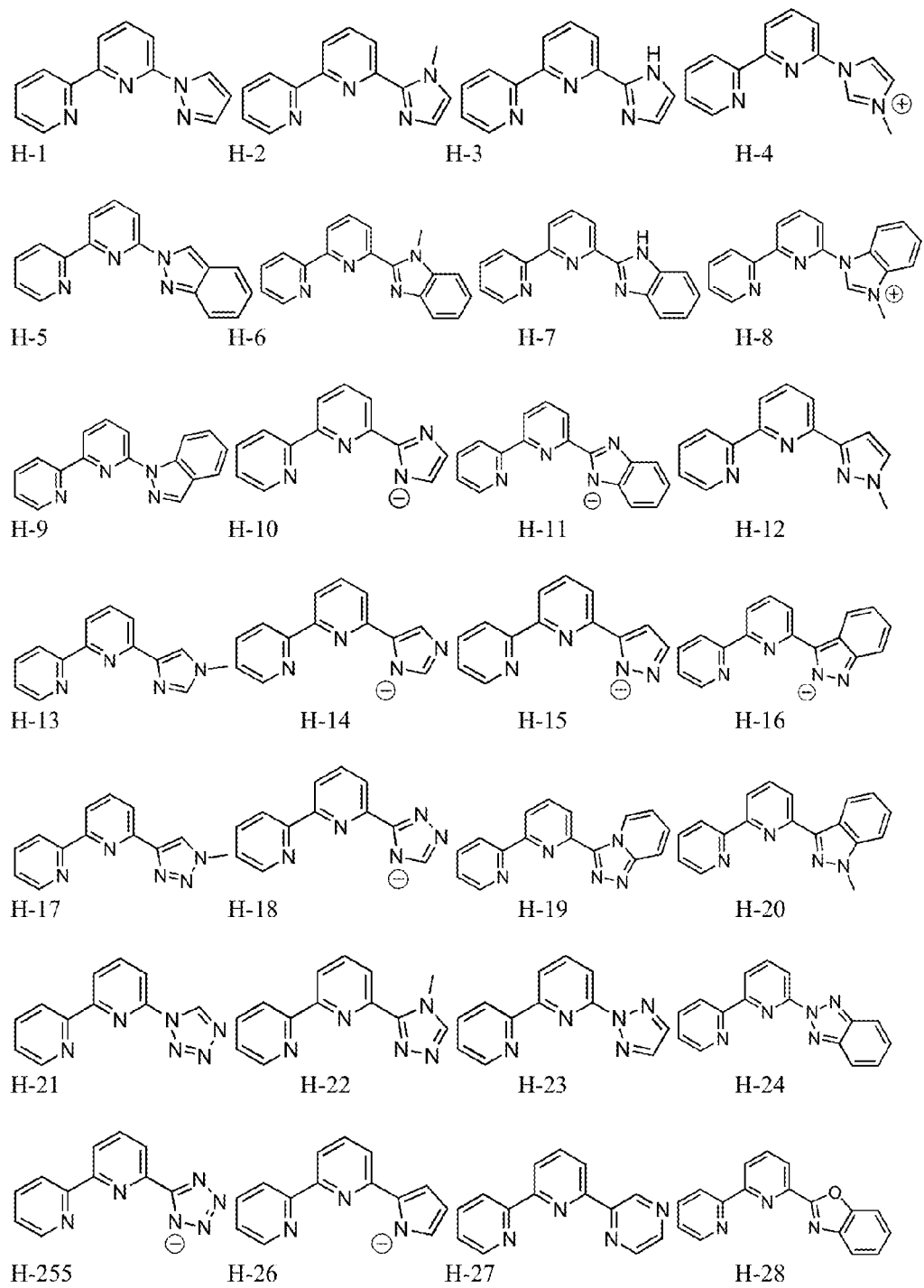
FIG. 6 (FIGS. 6-1 and 6-2) shows exemplary tridentate ligands La (H-1 to H-31) based on a substituted bipyridine, which ligands may be used in a complex in accordance with an embodiment of the invention.
Figures 2, 6:
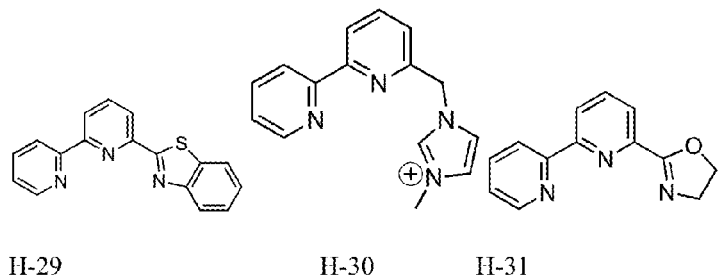
Figures 1, 7:
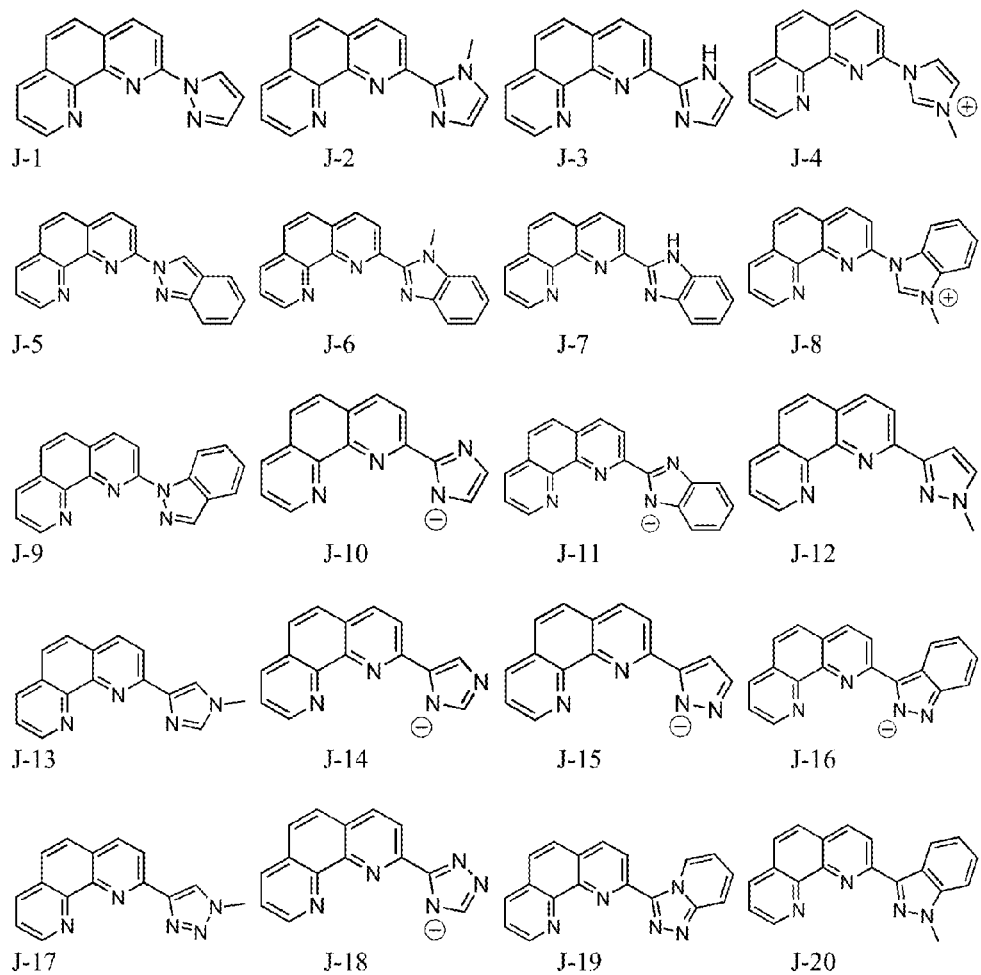
FIG. 7 (7-1 and 7-2) shows exemplary tridentate ligands La (J-1 to J-26) based on a substituted phenantroline, which ligands may be used in a complex in accordance with an embodiment of the invention.
Figures 2, 7:
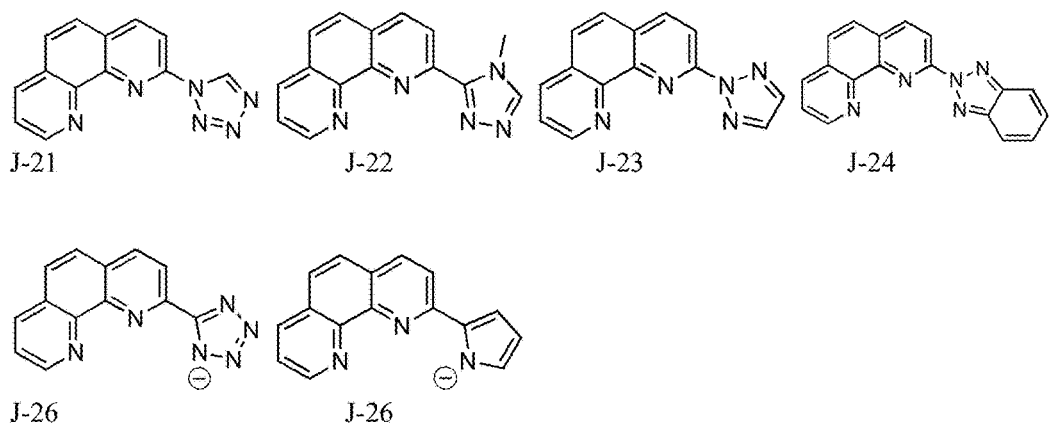
Figures 1, 8:
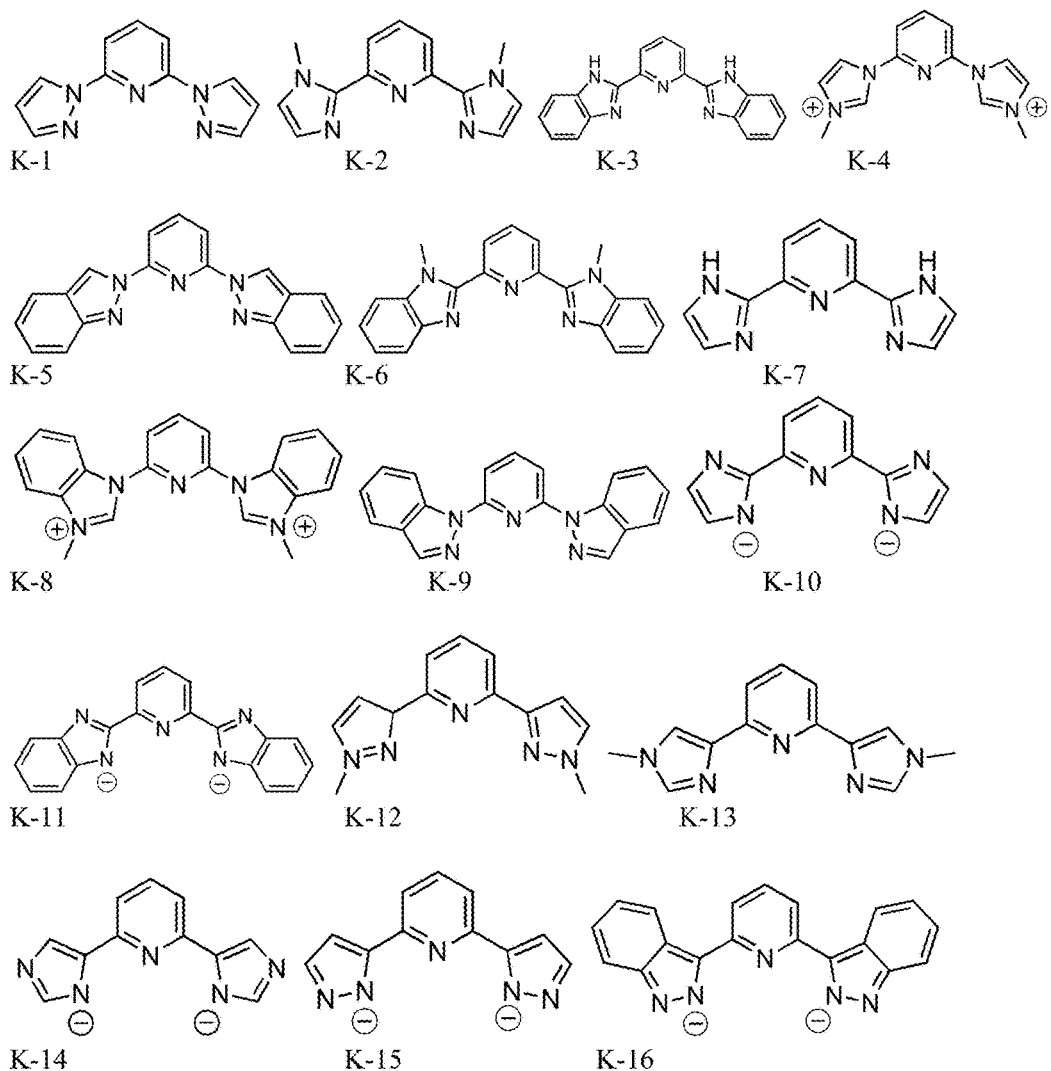
FIG. 8 (8-1 and 8-2) shows exemplary tridentate ligands La (K-1 to K-33) based on a di-substituted pyridine, which ligands may be used in a complex in accordance with an embodiment of the invention.
Figures 2, 8:
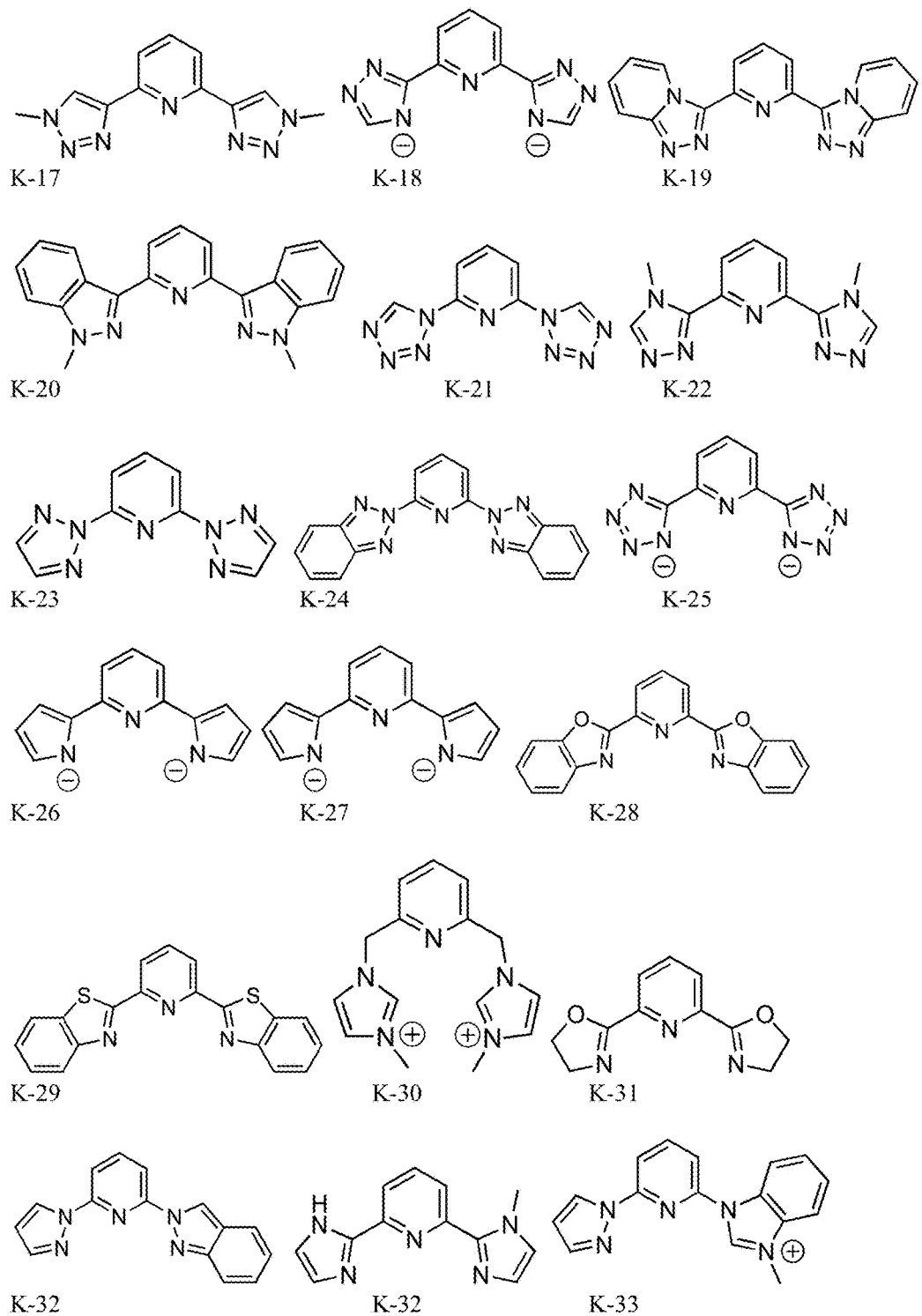
Figure 9:
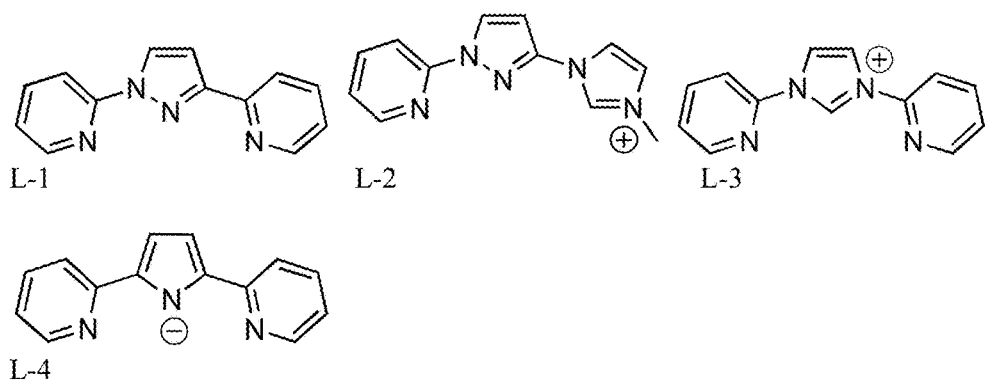
FIG. 9 shows exemplary tridentate ligands La (L-1 to L-4) based on a di-substituted pyrazole, imidazole or pyrrole, which ligands may be used in a complex in accordance with an embodiment of the invention.
Figures 1, 10:
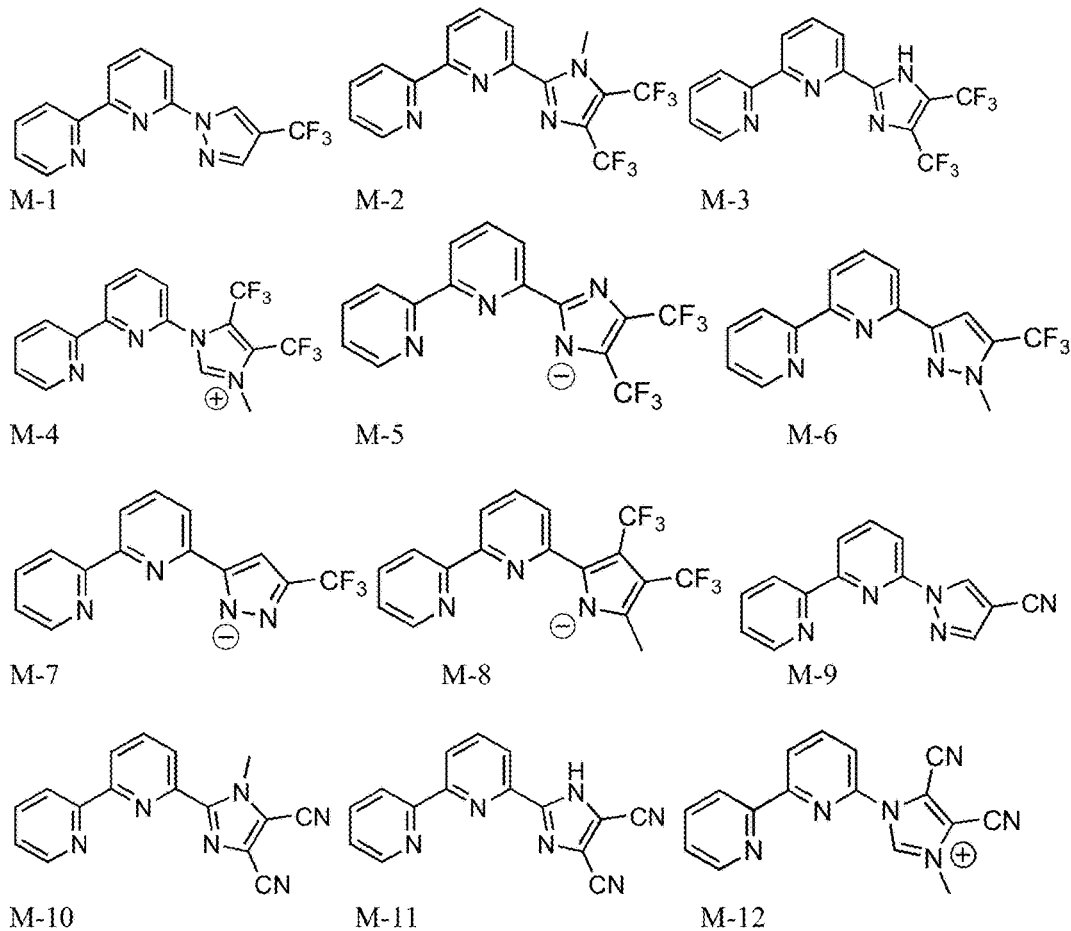
FIG. 10 (10-1 and 10-2) shows exemplary ligands (M-1 to M-15) of a similar type as those shown in FIG. 6, with additional substituents being present.
Figures 2, 10:
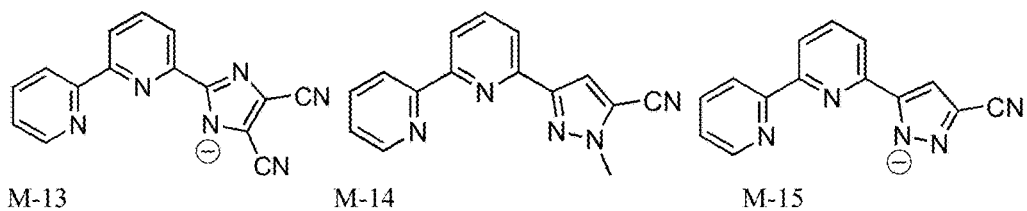
Figures 1, 11:
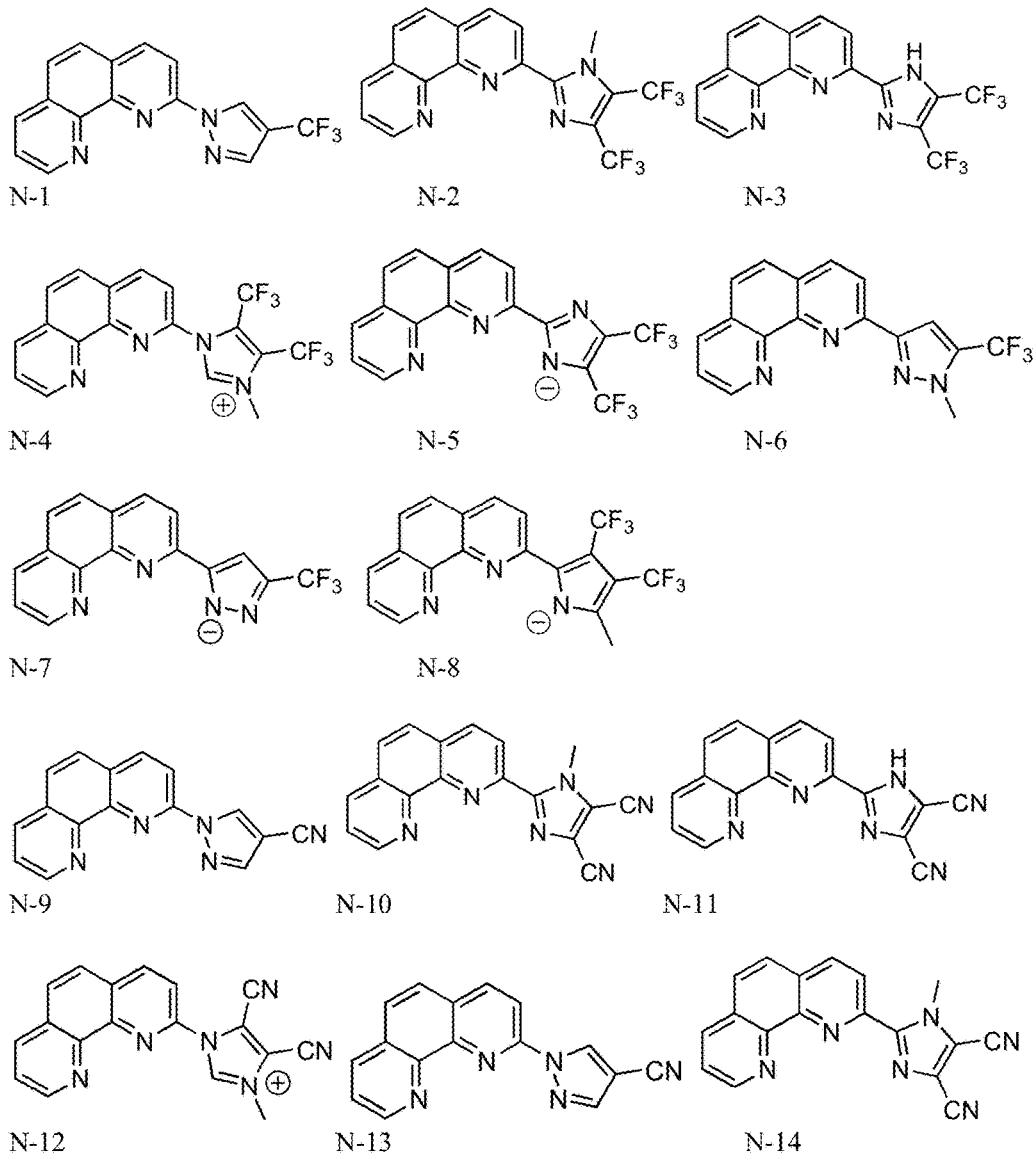
FIG. 11 (11-1 and 11-2) shows exemplary ligands (N-1 to N-20) of a similar type as those shown in FIG. 7, with additional substituents being present.
Figures 2, 11:
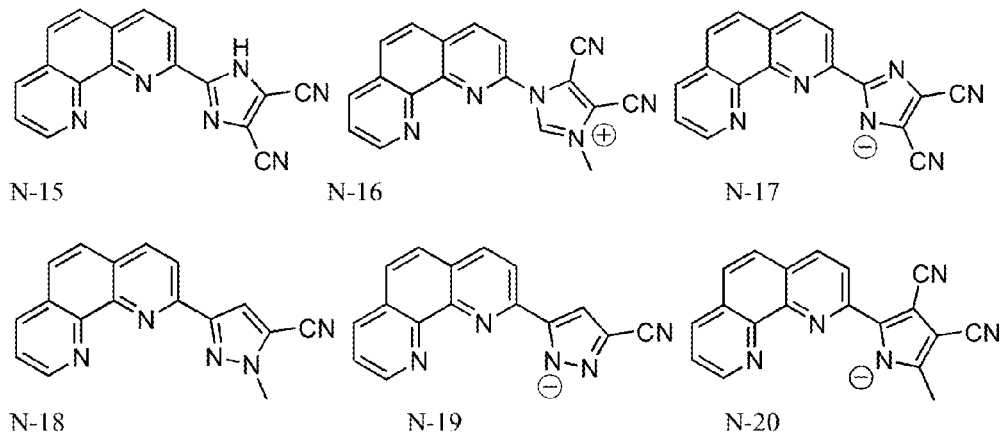
Figures 1, 12:
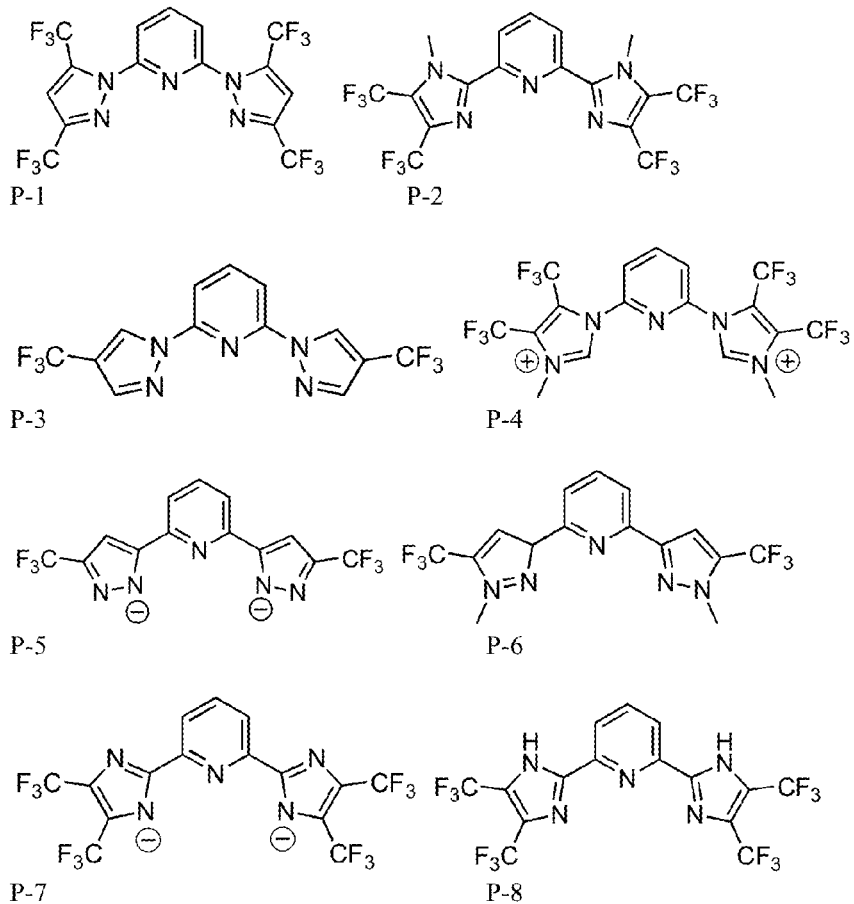
FIG. 12 (12-1 and 12-2) shows exemplary ligands (P-1 to P-16) of a similar type as those shown in FIG. 7, with additional substituents being present.
Figures 2, 12:
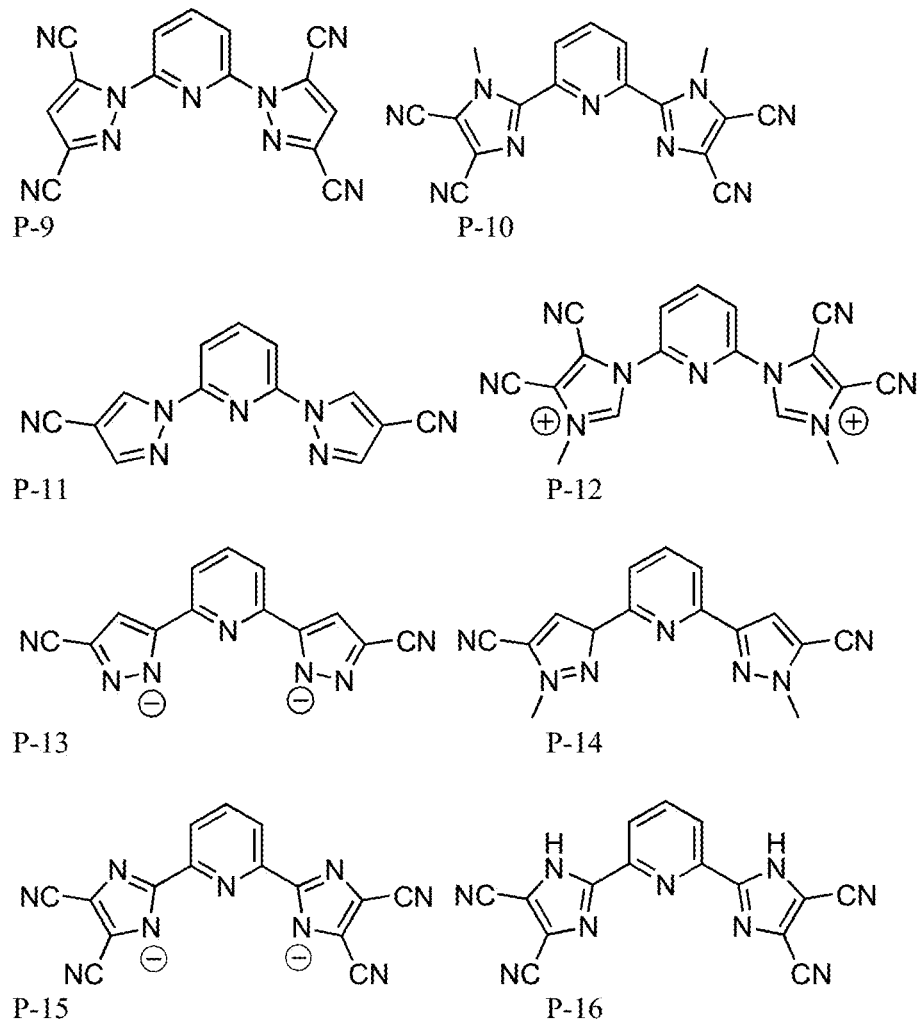
Figures 1, 13:
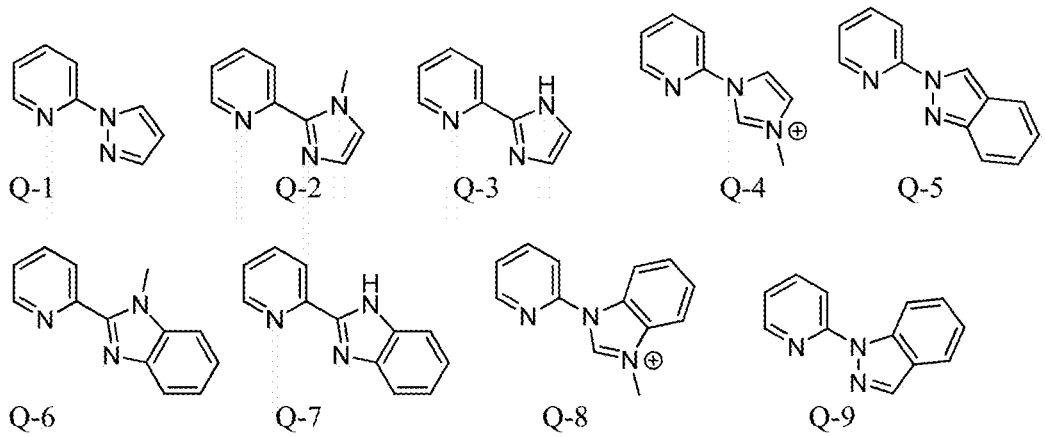
FIG. 13 (13-1, 13-2, 13-3, 13-4) shows exemplary bidentate ligands (Q-1 to Q-63) based on substituted pyridine, pyrazole, imidazole or pyrrole, which ligands may be used in a complex in accordance with an embodiment of the invention.
Figures 2, 13:
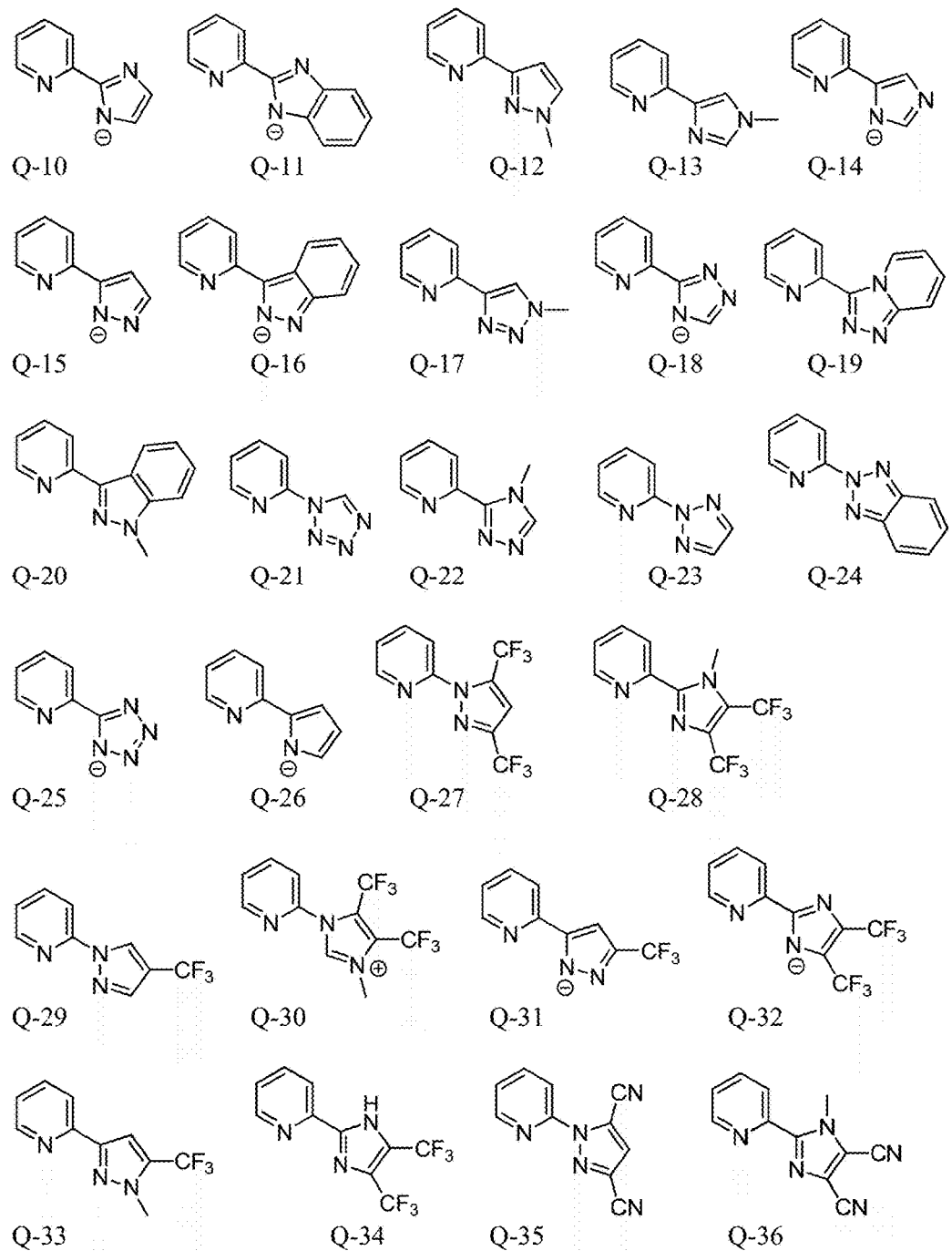
Figures 3, 13:
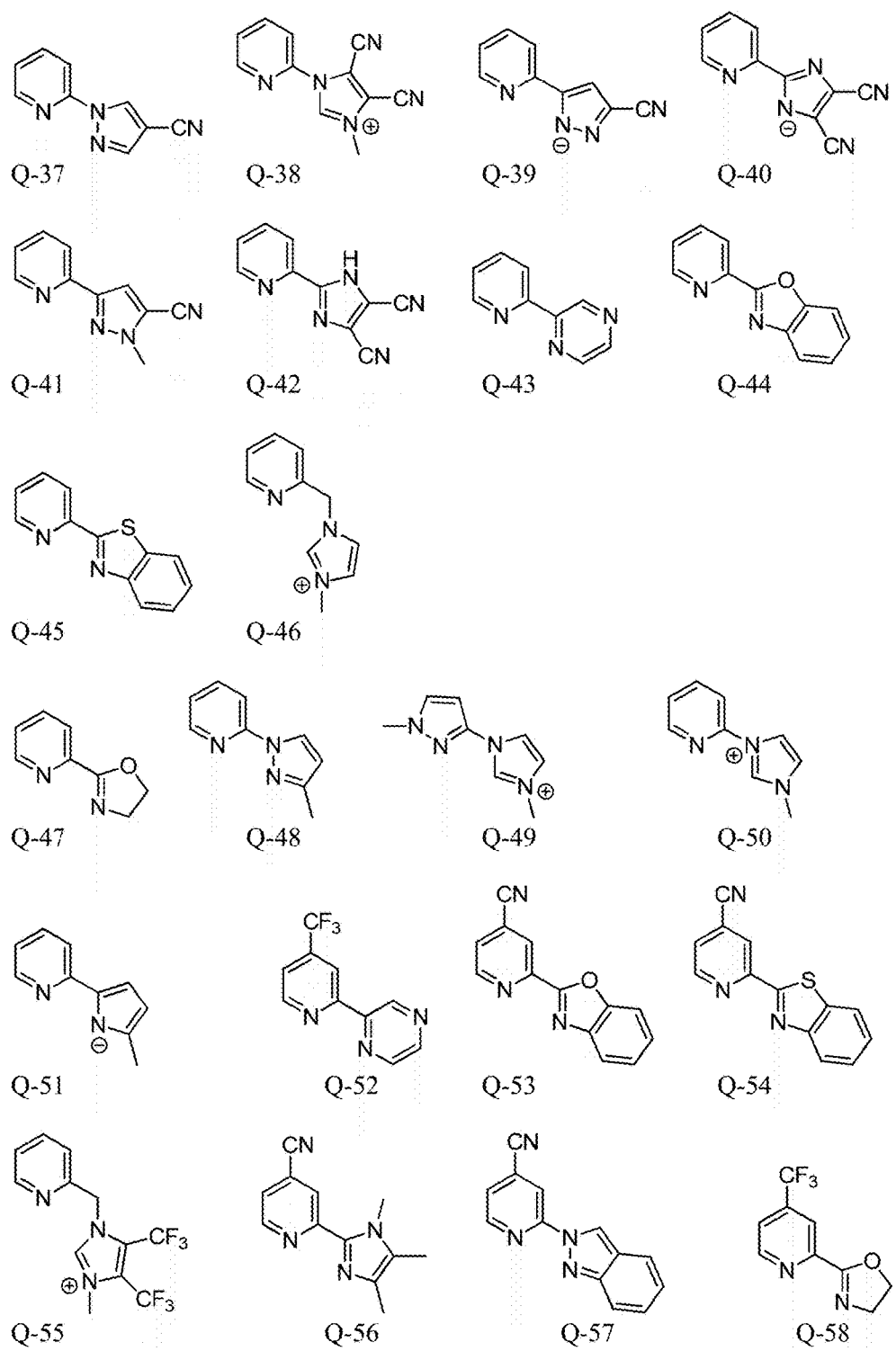
Figures 4, 13:
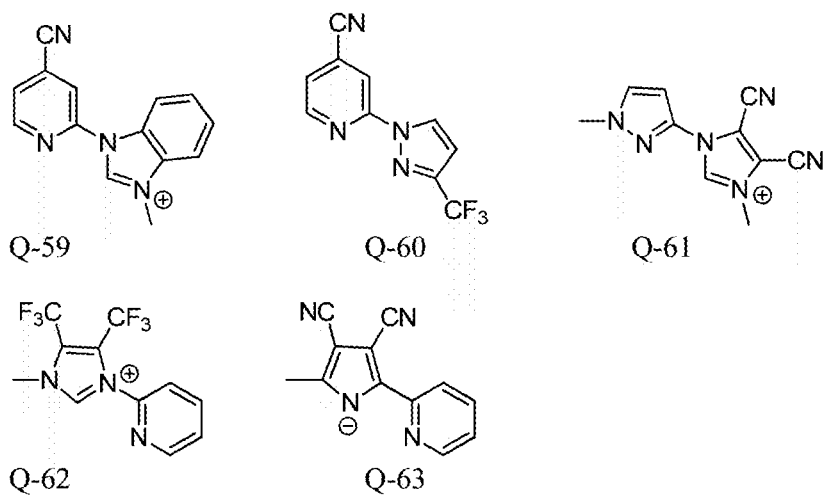

Preferably, in the flexible device, the said conductive layer 2 is provided by a conductive metal foil, such as a titanium or zinc foil, as shown by reference numeral 2 in FIG. 5, for example, and said flexible substrate 1 is a polymer or plastic foil. A second conductive layer, which is transparent, is part of the counter electrode 7 and is in contact with the plastic foil as described above (for example in the form of ITO-PET or ITO-PEN). Conductive titanium foils and conductive plastic substrates are disclosed by Seigo Ito et al. Chem. Comm. 2006, 4004-4006, and in EP1095387, for example.

According to an embodiment, the flexible device of the present invention is an inversed solar cell, with electromagnetic radiation entering the cell mainly from the side of the counter electrode (back illumination), as shown in FIG. 16, where the arrow hv refers to the side of illumination.

According to an embodiment, the flexible cell of the present invention is an inversed solar cell, in which, a transparent plastic substrate 1 comprises a counter electrode assembly 7, which, in this order from top to the bottom, comprises a transparent conductive oxide, for example ITO (tin-doped indium oxide) deposited on the flexible plastic foil 1, and a catalyst, such as carbon or Pt (platinum), for example.

On the bottom end, a conductive foil 2, preferably a metal foil, such as a Ti or zinc foil, for example, is provided, which may but need not be provided on a flexible support, such as a plastic material.

In another aspect, the invention provides a photoelectrochemical and/or optoelectronic device comprising at least one complex according to any one of complexes of formulae (XX), (XXI) and (XXII).

According to a further embodiment, the photoelectrochemical and/or optoelectronic device comprising at least one complex according to any one of complexes of formulae (XX), (XXI) and (XXII) is selected from an organic photovoltaic device, a photovoltaic solid state device, a p-n heterojunction, an organic solar cell, a dye sensitized solar cell, a solid state solar cell, a phototransistor and OLED (organic light-emitting diode).

According to a further embodiment, the photoelectrochemical and/or optoelectronic device comprising at least one complex according to any one of complexes of formulae (XX), (XXI) and (XXII) further comprises an organic charge transporting layer, said organic charge transporting layer comprising an organic charge transport material and at least one complex according to any one of complexes of formulae (XX), (XXI) and (XXII). Said complex is used as dopant in the organic charge transport material and forms with the organic charge transport material, which may be selected from organic electron and/or hole transport material, a doped organic charge transport material.

The photoelectrochemical and/or optoelectronic device comprising at least one complex according to any one of complexes of formulae (XX), (XXI) and (XXII) may comprise a conducting support layer, n-type semiconductor, a light-harvester layer or a sensitizer layer, a hole transporting layer and a counter electrode and/or metal layer. The photoelectrochemical and/or optoelectronic device may comprise an optional surface-increasing scaffold structure. Said metal layer may be doped as well as the n-type and/or the p-type semiconductor. A conductive layer comprising a conductive material may be present between the hole transporting layer and the counter electrode and/or metal layer. The hole transporting layer may be provided on the sensitizer layer and is between the sensitizer layer and the conducting current providing layer, if present, or the counter electrode and/or metal layer. Further layer may be present.

According to a further embodiment, the photoelectrochemical and/or optoelectronic device comprising at least one complex according to any one of complexes of formulae (XX), (XXI) and (XXII) may comprise a combination of two or more compounds of the invention as dopant. The hole transporting layer may comprise the combination of two or more complexes of the invention.

The photoelectrochemical and/or optoelectronic device comprising at least one complex according to any one of complexes of formulae (XX), (XXI) and (XXII) may comprise a hole collector layer, a conductive layer, an electron blocking layer, a sensitizer layer and a current collector layer, wherein the hole collector layer is coated by the conductive layer; wherein the electron blocking layer is between the conductive layer and the sensitizer layer, which is in contact with the current collector layer being a metal or a conductor. The hole collector layer may comprise a hole transporting material comprising at least one complex of the invention, providing together a doped p-type organic charge material.

The conductive material is selected from one or more conductive polymers or one or more hole transporting materials, which may be selected from poly(3,4-ethylenedioxythiophene):poly(styrenesulfonate) (PEDOT:PSS), poly(3,4-ethylenedioxythiophene):poly(styrenesulfonate):grapheme nanocomposite (PEDOT:PSS:graphene), poly(N-vinylcarbazole) (PVK) and sulfonated poly(diphenylamine) (SPDPA), preferably from PEDOT:PSS, PEDOT:PSS:graphene and PVK, more preferably from PEDOT:PSS. Conductive polymers may also be selected from polymers comprising polyaniline, polypyrrole, polythiophene, polybenzene, polyethylenedioxythiophene, polypropylenedioxythiophene, polyacetylene, and combinations of two or more of the aforementioned, for example.

The conducting support layer is preferably substantially transparent. "Transparent" means transparent to at least a part, preferably a major part of the visible light. Preferably, the conducting support layer is substantially transparent to all wavelengths or types of visible light. Furthermore, the conducting support layer may be transparent to non-visible light, such as UV and IR radiation, for example.

According to an embodiment, the conducting support layer provides the support layer of the photoelectrochemical and/or optoelectronic device comprising at least one complex according to any one of complexes of formulae (XX), (XXI) and (XXII). Preferably, the optoelectronic and/or electrochemical device is built on said support layer. The support of the device may be also provided on the side of the counter electrode. In this case, the conductive support layer does not necessarily provide the support of the device, but may simply be or comprise a current collector, for example a metal foil.

The conducting support layer preferably functions and/or comprises a current collector, collecting the current obtained from the device. The conducting support layer may comprise a material selected from indium doped tin oxide (ITO), fluorine doped tinoxide (FTO), ZnO—$Ga_2O_3$, ZnO—$Al_2O_3$, tin-oxide, antimony doped tin oxide (ATO), $SrGeO_3$ and zinc oxide, preferably coated on a transparent substrate, such as plastic or glass. In this case, the plastic or glass provides the support structure of the layer and the cited conducting material provides the conductivity. Such support layers are generally known as conductive glass and conductive plastic, respectively, which are thus preferred conducting support layers in accordance with the invention. The conducting support layer comprises a conducting transparent layer, which may be selected from conducting glass and from conducting plastic.

The surface-increasing scaffold structure is provided on said conducting support structure or on a protective layer that may be provided on said scaffold structure. The surface-increasing scaffold structure is nanostructured and/or mesoporous.

The scaffold structure is made from and/or comprises a metal oxide. For example, the material of the scaffold structure is selected from semiconducting materials, such as Si, $TiO_2$, $SnO_2$, $ZrO_2$, $Al_2O_3$, $Fe_2O_3$, ZnO, $WO_3$, $Nb_2O_5$, CdS, ZnS, PbS, $Bi_2S_3$, CdSe, CdTe, $SrTiO_3$, GaP, InP, GaAs, $CuInS_2$, $CuInSe_2$, and combinations thereof, for example. Preferred semiconductor materials are Si, $TiO_2$, $SnO_2$, ZnO, $WO_3$, $Nb_2O_5$ and $SrTiO_3$, for example. According to an embodiment, the surface-increasing scaffold structure is nanostructured and/or nanoporous.

The invention does not intend to exclude the possibility that there are one or more intermediate layers between the scaffold structure and the conductive support. Such intermediate layers, if present, would preferably be conducting and/or semiconducting.

According to an embodiment, the sensitizer layer of the photoelectrochemical and/or optoelectronic device comprising at least one complex according to any one of complexes of formulae (XX), (XXI) and (XXII) comprises at least one pigment being selecting from organic, inorganic, organometallic and organic-inorganic pigments or a combination thereof. The sensitizer is preferably a light absorbing compound or material. Preferably, the sensitizer is a pigment, and most preferably the sensitizer is an organic-inorganic pigment.

The sensitizer may, for example, comprise at least one dye disclosed in WO2004/097871A1 or suitable ruthenium dyes are disclosed, for example, in WO2006/010290. The sensitizer may either be a light absorber comprising at least one perovskite material as disclosed in WO 2014/020499A1 and/or WO 2016/055025A1.

The sensitizer layer or light-harvester layer may comprise one or more pigments of the group consisting of organometallic sensitizing compounds (phthalocyanine derived compounds, porphyrine derived compounds), metal free organic sensitizing compounds (diketopyrrolopyrrole (DPP) based sensitizer), inorganic sensitizing compounds such as quantum dots, $Sb_2S_3$(Antimonysulfide, for example in the form of thin films), aggregates of organic pigments, nanocomposites, in particular organic-inorganic perovskites, and combinations of the aforementioned.

In another embodiment, the photoelectrochemical and/or optoelectronic device comprising at least one complex according to any one of complexes of formulae (XX), (XXI) and (XXII) is selected from a photovoltaic solid state device or a solar cell comprising an organic-inorganic perovskite as light absorber under the form of a layer.

The photoelectrochemical and/or optoelectronic device comprising at least one complex according to formula (I) may also be selected from a photovoltaic solid state device or a solar cell comprising an organic-inorganic perovskite as light absorber under the form of a layer. Preferably the photoelectrochemical and/or optoelectronic device comprises at least one complex according to formula (I) as a dopant.

The light absorbing layer may comprise a further pigment in addition to the organic-inorganic perovskite pigment, said further pigment selected from organic pigment, organometallic pigment or inorganic pigment.

The term "perovskite", for the purpose of this specification, refers to the "perovskite structure" and not specifically to the perovskite material, $CaTiO_3$. For the purpose of this specification, "perovskite" encompasses and preferably relates to any material that has the same type of crystal structure as calcium titanium oxide and of materials in which the bivalent cation is replaced by two separate monovalent cations. The perovskite structure has the general stoichiometry $WYX_3$, where "W" and "Y" are cations and "X" is an anion. The "W" and "Y" cations can have a variety of charges and in the original perovskite mineral ($CaTiO_3$), the W cation is divalent and the Y cation is tetravalent. For the purpose of this invention, the perovskite formulae includes structures having three (3) or four (4) anions, which may be the same or different, and/or one or two (2) organic cations, and/or metal atoms carrying two or three positive charges, in accordance with the formulae presented elsewhere in this specification.

The photoelectrochemical and/or optoelectronic device comprising at least one complex according to any one of complexes of formulae (XX), (XXI) and (XXII) may comprise one or more layers of an organic-inorganic perovskite. In said device, the last upper layer of organic-inorganic perovskite is coated by the hole transporting layer comprising a hole transporting material and at least one complex of the invention.

The photoelectrochemical and/or optoelectronic device comprising at least one complex according to formula (I) may comprise one or more layers of an organic-inorganic perovskite. In said device, the last upper layer of organic-inorganic perovskite is coated by the hole transporting layer comprising a hole transporting material and at least one complex of the invention.

WO 2014/020499A1 describes organic-inorganic perovskite compounds, which may be used as sensitizers in a photoelectrochemical and/or optoelectronic device of the invention.

In particular, the organic-inorganic perovskite layer material the optoelectronic and/or photoelectrochemical device of the invention comprises a perovskite-structure according any one of formulae (XXXII), (XXXIIa), (XXXIIb), (XXXIIc), (XXXIId), (XXXIIe), (XXXIIf) and (XXXIIg) below:

$WW'YX_4$ (XXXII)

$WYX_3$ (XXXIIa)

$WW'N_{2/3}X_4$ (XXXIIb)

$WN_{2/3}X_3$ (XXXIIc)

$BN_{2/3}X_4$ (XXXIId)

$BYX_4$ (XXXIIe), $WW'W_1MX_3$ (XXXIIf)

$WW_1MX_3$ (XXXIIg)

wherein

W and W' are organic, monovalent cations that are independently selected from primary, secondary, tertiary or quaternary organic ammonium compounds, including N-containing hetero-rings and ring systems, W and W' having independently from 1 to 60 carbons and 1 to 20 heteroatoms;

$W_1$ is an inorganic cation selected from $Cs^+$, $Rb^+$, $K^+$;

B is an organic, bivalent cation selected from primary, secondary, tertiary or quaternary organic ammonium compounds having from 1 to 60 carbons and 2-20 heteroatoms and having two positively charged nitrogen atoms;

Y is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^2$, $Pb^{2+}$, $Eu^{2+}$, or $Yb^{2+}$;

N is selected from the group of $Bi^{3+}$ and $Sb^{3+}$; and,

X is independently selected from $Cl^-$, $Br^-$, $I^-$, $NCS^-$, $CN^-$, $BF_4^-$, $PF_6^-$, $CNO^-$, $SeCN^-$, and $NCO^-$.

According to a further embodiment, said organic-inorganic perovskite layer comprises a perovskite-structure according to any one of the formulae (XXXIIh) to (XXXIInl):

$WPbX_3$ (XXXIIh)

$WSnX_3$ (XXXIIi)

$WBiX_4$ (XXXIIj)

$WW'PbX_4$ (XXXIIk)

$WW'SnX_4$ (XXXIIl)

$BPbX_4$ (XXXIIm)

$BSnX_4$ (XXXIIn)

wherein W, W', B and X are as defined above in this specification. Preferably, X is preferably selected from $Cl^-$, $Br^-$ and $I^-$, most preferably X is $I^-$ or a mixture of $Br^-$ and $I^-$.

According to a preferred embodiment, said organic-inorganic perovskite layer comprises a perovskite-structure of the formulae (XXXIIh) to (XXXIIn), more preferably (XXXIIh) and/or (XXXIIi) above.

According to an embodiment, W and W' are monovalent cations selected independently from any one of the moieties of formulae (XXXII-70) to (XXXII-78) below:

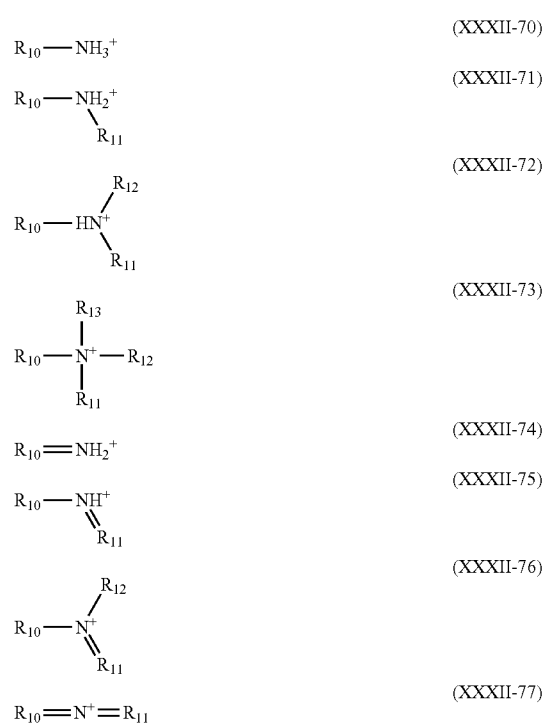

-continued

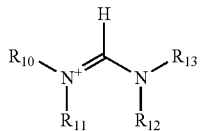

(XXXII-78)

wherein, $R_{10}$ to $R_{13}$ of formulae (XXXII-70) to (XXXII-78) are independently selected from C1-C15 organic substituents comprising from 0 to 15 heteroatoms.

According to an embodiment, any one, several or all hydrogens of said C1-C15 organic substituent may be replaced by halogen and said organic substituent may comprise 0-15 heteroatoms being selected from N, S or O, and wherein, in any one of the moieties (XXXII-70) to (XXXII-78), $R_{10}$ to $R_{13}$ may be covalently connected to each other to form a substituted or unsubstituted ring or ring system. Preferably, in a chain of atoms of said C1-C15 organic substituent, any heteroatom is connected to at least one carbon atom. Preferably, neighboring heteroatoms are absent and/or heteroatom-heteroatom bonds are absent in said C1-C15 organic substituent comprising from 0 to 15 heteroatoms. The heteroatoms may be selected from N, S, and/or O.

According to an embodiment, $R_{10}$ to $R_{13}$ of the moieties of formulae (XXXII-70) to (XXXII-78) are independently selected from C1 to C15 or C4 to C15 hydrocarbyl groups, wherein one or more than one hydrogens in said substituent may be replaced by halogen and wherein, in any one of the moieties (XXXII-70) to (XXXII-78), the two or more of the substituents present may be covalently connected to each other to form a substituted or unsubstituted ring or ring system.

According to a preferred embodiment, the organic-inorganic perovskite in the device of the invention is selected from a compound of formula (XXXII) or (XXXIIa).

According to an embodiment, B is a bivalent cation selected from any one of the compounds of formulae (XXXII-79) and (XXXII-80) below:

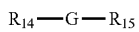

(XXXII-79)

(XXXII-80)

wherein, in the compound of formula (XXXII-79), G is an organic linker structure having 1 to 10 carbons and 0 to 5 heteroatoms selected from N, S, and/or O, wherein one or more hydrogen atoms in said G may be replaced by halogen; wherein $R_{14}$ and $R_{15}$ are independently selected from a compounds of any one of formulae (70) to (78); and wherein, in the compound of formula (XXXII-80), the circle containing said two positively charged nitrogen atoms represents a substituted or unsubstituted aromatic ring or ring system comprising 4 to 15 carbon atoms and 2 to 7 heteroatoms or 4 to 10 carbon atoms and 2 to 5 heteroatoms, wherein said nitrogen atoms are ring heteroatoms of said ring or ring system, and wherein the remaining of said heteroatoms may be selected independently from N, O and S and wherein $R_{16}$ and $R_{17}$ are independently selected from H and from a compounds of any one of formulae (XXXII-70) to (XXXII-78). Halogen atom substituting hydrogen atom totally or partially may also be present in addition to and/or independently of said 2 to 7 heteroatoms.

According to a preferred embodiment, the metal Y is selected from $Sn^{2+}$ and $Pb^{2+}$, preferably $Pb^{2+}$. According to a preferred embodiment, N is $Sb^{3+}$.

According to a preferred embodiment, the three or four X are independently selected from $Cl^-$, $Br^-$, and $I^-$.

In a further aspect, the invention provides use of the complex according to any one of formulae (I), (XX), (XXI) and (XXII) of the invention as a tuner of HOMO level.

EXAMPLES

Example 1: Synthesis of Different Pyridine-Pyrazole Ligands 2-(1H-pyrazol-1-yl)pyridine (also 1-(pyridine-2-yl)-1H-pyrazol, Py-Pz)) (see ligands of complex 1 in FIG. 1) was obtained as disclosed in Elguero J. et al., Chemische Berichte, 1996, 129, pages 589-594.

4-Methyl-2-(1H-pyrazol-1-yl)pyridine (MePy-Pz). 0.95 g (14.0 mmol, 2 eq) of Pyrazole was dissolved in 20 mL of DMSO at room temperature and 1.57 g (14.0 mmol, 2 eq) of KO$^t$Bu was added. The mixture was heated to 40° C. for 20 min. and then 0.78 g (7.0 mmol, 1 eq) of 2-Fluoro-4-picoline (2-Fluoro-4-methyl-pyridine) was added and the mixture was heated to 110° C. overnight. After cooling to room temperature the mixture was diluted with water and extracted with $Et_2O$ (3×). The combined colourless organic layers were washed with water, dried over $MgSO_4$ and concentrated. The yellow oil was purified by column chromatography using $CH_2Cl_2$/EtOAc=6/1 as solvent mixture. The pure product was obtained as colourless liquid in 99% yield (1.11 g, 6.9 mmol).

2-(3,5-Dimethyl-1H-pyrazol-1-yl)pyridine (Py-PzMe$_2$) and 2-(3,5-Dimethyl-1H-pyrazol-1-yl)-4-methylpyridine (MePy-PzMe$_2$) were synthesized accordingly.

4,4'-Dichloro-2,2'-bipyridine (CAS-No. 1762-41-0, also referred to as $Cl_2$Bipy herein) is commercially available.

Example 2: Synthesis of [Co(Py-Pz)$_3$](Pf$_6$)$_2$ (CoIII Complex 1)

225 mg (1.55 mmol, 3.1 eq) of pyridine-pyrazole (Py-Pz) ligand (Example 1) were dissolved in 20 mL of MeOH and then 119 mg (0.5 mmol, 1 eq) of $CoCl_2$*6H$_2$O were added as a solid. The mixture was heated to reflux for 2 h. After cooling to r.t. excess of KPF$_6$ dissolved in MeOH was added to the mixture. The mixture was stored at 3° C. for precipitation. After 3 h the product was collected on a sintered glass frit and dried in vacuo. The pure product (FIG. 1, compound 1) was obtained as orange crystals. Yield: 246 mg (0.33 mmol, 66%). HRMS (ESI-TOF) m/z (%): calcd. for $C_{24}H_{21}CoN_9$. 247.0626. found 247.0635 (100) [(M−2PF$_6$)$^{2+}$].

Example 3: Synthesis of [Co(Py-Pz)$_3$](Pf$_6$)$_3$ (CoIII Complex 2)

218 mg (1.5 mmol, 3.0 eq) of pyridine-pyrazole ligand were dissolved in 10 mL of water and heated to 75° C. until complete solution occurred. Then 119 mg (0.5 mmol, 1 eq) of $CoCl_2$*6H$_2$O were added to the colourless solution. To the pink solution $H_2O_2$ (1 mL, 30%) and HCl (1 mL, 25%) were added to oxidize the cobalt. After 10 min. 460 mg (2.5 mmol, 5 eq) of KPF$_6$ dissolved in 10 mL of hot water were added drop wise to the mixture. Precipitation occurred and the mixture was allowed to cool to room temperature. The product was collected on a sintered glass frit and dried in vacuo. The pure fac-Isomer (FIG. 1, complex 2) was obtained as orange solid. Yield: 259 mg (0.28 mmol, 56%). $^1$H NMR (400 MHz, acetone-D6): δ 9.56-9.53 (m, 3H, ArH), 8.73-8.64 (m, 6H, ArH), 8.01-7.81 (m, 9H, ArH), 7.27-7.23 (m, 3H, ArH) ppm.

Examples 4 and 5

Synthesis of [Co(MePy-Pz)$_3$](PF$_6$)$_2$, and [Co(p-MePy-Pz)$_3$](PF$_6$)$_3$ (CoII and CoIII Complexes 3 and 4)

478 mg (3.0 mmol, 3.0 eq) of MePy-Pz ligand (Example 1) were dissolved in a 2:1 mixture of water and MeOH (20 mL/10 mL) and then heated to 70° C. 238 mg (1.0 mmol, 1 eq) of CoCl$_2$*6H$_2$O were added as a solid. The mixture was stirred at 70° C. for 10 min and then 0.92 g KPF$_6$ dissolved in 20 mL of hot water were added. After cooling to r.t. the precipitate was collected on a sintered glass frit, washed with water and Et$_2$O and dried in vacuo. The pure fac-Isomer (FIG. 1, complex 3) was obtained as pale orange solid. Yield: 668 mg (0.81 mmol, 81%). HRMS (ESI-TOF) m/z (%): calcd. for C$_{27}$H$_{27}$CoN$_9$. 268.0861. found 268.0860 (100) [(M−2PF$_6$)$^{2+}$]. Anal. Calcd. for C$_{27}$H$_{27}$CoF$_{12}$N$_9$P$_2$ (826.43): C, 39.24; H, 3.23; N, 15.25. found: C, 39.23; H, 3.35; N, 14.84%.

380 mg (2.4 mmol, 3.0 eq) of MePy-Pz ligand were dissolved in a 2:1 mixture of water and MeOH (20 mL/10 mL) and then heated to 70° C. 190 mg (0.8 mmol, 1 eq) of CoCl$_2$*6H$_2$O were added as a solid. The mixture was stirred at 70° C. for 10 min and then 2 mL of H$_2$O$_2$ (30%) and 2 mL of HCl (25%) were added and the mixture was stirred at 70° C. for further 30 min. 0.92 g KPF$_6$ dissolved in 20 mL of hot water were added. After cooling to r.t. the precipitate was collected on a sintered glass frit, washed with water and Et$_2$O and dried in vacuo. The pure fac-Isomer (FIG. 1, complex 4) was obtained as orange solid. Yield: 287 mg (0.3 mmol, 38%). $^1$H NMR (400 MHz, acetone-D6): δ 9.49-9.46 (m, 3H, ArH), 8.56 (s, 3H, ArH), 7.94 (d, J=30.2 Hz, 3H, ArH), 7.73-7.71 (m, 3H, ArH), 7.68-7.60 (m, 3H, ArH), 7.25-7.21 (m, 3H, ArH), 2.73 (s, 9H, CH$_3$) ppm. HRMS (ESI-TOF) m/z (%): calcd. for C$_{27}$H$_{27}$CoN$_9$P2F$_{12}$ 826.1005. found 826.1021 (35) [(M−PF$_6$)$^+$]. calcd. for C$_{27}$H$_{27}$CoN$_9$PF$_6$ 340.5682. found 340.5704 (63) [(M−2PF$_6$)$^{2+}$].

Examples 6 and 7

Synthesis of [Co(Py-PzMe$_2$)$_3$](PF$_6$)$_2$, and [Co(Py-PzMe$_2$)$_3$](PF$_6$)$_3$ (CoII and CoIII Complexes 5 and 6)

520 mg (3.0 mmol, 3.0 eq) of Py-PzMe$_2$ ligand (Example 1) were dissolved in a 2:1 mixture of water and MeOH (20 mL/10 mL) and then heated to 70° C. 238 mg (1.0 mmol, 1 eq) of CoCl$_2$*6H$_2$O were added as a solid. The mixture was stirred at 70° C. for 10 min and then 0.92 g KPF$_6$ dissolved in 20 mL of hot water were added. After cooling to r.t. the precipitate was collected on a sintered glass frit, washed with water and Et$_2$O and dried in vacuo. The pure product (pink solid) (FIG. 1, complex 5) was obtained as mixture of mer- and fac-Isomer. Yield: 737 mg (0.85 mmol, 85%). HRMS (ESI-TOF) m/z (%): calcd for C$_{30}$H$_{31}$CoN$_9$. 289.1096. found 289.1091 (100) [(M+2H−2PF$_6$)$^{2+}$]. Anal. Calcd. for C$_{30}$H$_{33}$CoF$_{12}$N$_9$P$_2$ (868.51): C, 41.49; H, 3.83; N, 14.51. found: C, 40.69; H, 3.86; N, 13.56%.

1.04 g (6.0 mmol, 3.0 eq) of Py-PzMe$_2$ ligand were dissolved in a 2:1 mixture of water and MeOH (40 mL/20 mL) and then heated to 70° C. 476 mg (2.0 mmol, 1 eq) of CoCl$_2$*6H$_2$O were added as a solid. The mixture was stirred at 70° C. for 10 min and then 5 mL of H$_2$O$_2$ (30%) and 5 mL of HCl (37%) were added and the mixture was stirred at 70° C. for further 3 h. Excess of aq. KPF$_6$ solution was added. After cooling to r.t. the precipitate was collected on a sintered glass frit, washed with water and Et$_2$O and dried in vacuo. The pure product (FIG. 1, complex 6) was obtained as orange solid. Yield: 100 mg (0.1 mmol, 5%). $^{19}$F NMR (188 MHz, acetone–D6): δ −72.6 (d, $^1$J$_{PF}$=706 Hz, PF$_6$) ppm. HRMS (ESI-TOF) m/z (%): calcd. for C$_{30}$H$_{33}$CoN$_9$P$_2$F$_{12}$ 868.1475. found 868.1669 (100) [(M−PF$_6$)$^+$].

Examples 8 and 9

Synthesis of [Co(Cl$_2$Bipy)$_3$](PF$_6$)$_2$, and [Co(Cl$_2$Bipy)$_3$](PF$_6$)$_3$ (CoII and CoIII Complexes 7 and 8)

238 mg (1.0 mmol, 1 eq) of CoCl$_2$*6H$_2$O were dissolved in 15 mL of water and 675 mg (3.0 mmol, 3 eq) of 4,4'-Dichloro-2,2'-bipyridine (Cl$_2$Bipy, Example 1), dissolved in 50 mL of acetone, were added. The solution instantly turned orange and was heated to 50° C. for 10 min. The mixture was concentrated until precipitation occurred. Then the mixture was heated to 50° C. again and just enough acetone was added to re-dissolve the precipitate. Excess of saturated aq. KPF6 solution was added to precipitate the complex as its PF$_6$ salt. The solid was collected on a glass-frit, washed with water and Et$_2$O and dried on air at 90° C. and then in vacuo. The product (FIG. 1, complex 7) was obtained as beige solid. Yield: 950 mg (0.93 mmol, 93%). $^1$H NMR (400 MHz, acetone-D6): δ 90.11 (s, 6H, ArH), 80.97 (s, 6H, ArH), 42.25 (s, 6H, ArH) ppm. $^{19}$F NMR (188 MHz, acetone-D6): δ −73.8 (d, $^1$J$_{PF}$=706 Hz, PF$_6$) ppm. Anal. Calcd. for C$_{30}$H$_{18}$Cl$_6$CoF$_{12}$N$_6$P$_2$ (1224.08): C, 35.18; H, 1.77; N, 8.21. found: C, 36.58; H, 1.76; N, 8.25%.

238 mg (1.0 mmol, 1 eq) of CoCl$_2$*6H$_2$O were dissolved in 15 mL of water and 675 mg (3.0 mmol, 3 eq) of Cl$_2$Bipy, dissolved in 60 mL of acetonitrile, were added. The solution instantly turned orange and was heated to 50° C. for 10 min. About 15 mL of acetonitrile were removed in vacuo. Then 4 mL of H$_2$O$_2$ (30%) and 4 mL of HCl (25%) were added. The mixture was heated to 50° C. for 90 min. Excess of saturated aq. KPF$_6$ solution was added to precipitate the complex as its PF$_6$ salt. The solid was collected on a glass-frit, washed with water and Et$_2$O and dried in vacuo. The product (FIG. 1, complex 8) was obtained as pale green solid. Yield: 1.125 g (0.96 mmol, 96%). $^1$H NMR (400 MHz, acetone-D6): δ 9.30 (t, $^4$J$_{HH}$=1.3 Hz, 6H, ArH), 7.97 (d, $^4$J$_{HH}$=1.3 Hz, 12H, ArH) ppm. $^{19}$F NMR (188 MHz, acetone-D): δ −72.3 (d, $^1$J$_{PF}$=708 Hz, PF$_6$) ppm. HRMS (ESI-TOF) m/z (%): calcd. for C$_{30}$H$_{18}$C$_{16}$CoF$_6$N$_6$P 438.9336. found 438.9354 (45) [(M−2PF$_6$)$^{2+}$]. calcd. for C$_{30}$H$_{18}$C$_{16}$CoN$_6$ 244.3010. found 244.3019 (100) [(M−3PF$_6$)$^{3+}$]. Anal. Calcd. for C$_{30}$H$_{18}$Cl$_6$CoF$_{18}$N$_6$P$_3$ (1169.05): C, 30.82; H, 1.55; N, 7.19. found: C, 31.04; H, 1.35; N, 7.35%.

Example 10: Redox Potential, Choice of Dopant and Conductivity Measurements

For conductivity measurements, substrates used for two-probe electrical conductivity measurements consisted of highly doped Si with a 300 nm thermally grown $SiO_2$ layer on which 5 nm Cr/30 nm Au electrodes were deposited and lithographically patterned to yield a channel length and width of 20 m and 1 mm, respectively. As a cleaning step, the substrates were sonicated in acetone and subsequently rinsed with 2-propanol, followed by the removal of residual organic traces via oxygen plasma treatment. The hole conductor was subsequently deposited by spin-coating a solution of Spiro-MeOTAD, TBP, LiTFSI and complex 2 in $CHCl_3$, whereas the concentrations were the same as in case of photovoltaic devices. I-V characteristics were recorded on a Keithley 4200 Semiconductor Characterization System.

The oxidation potential of spiro-MeOTAD in solution has been found to be 0.81 V versus normal hydrogen electrode (NHE) (Moon, S. et al. *J. Phys. Chem. C* 2009, 113, 16816-16820.) The basic requirement for the $Co^{(III)}$ complex thus is a redox potential lying above this value. For this reason we selected cobalt(III)tris(1-(pyridin-2-yl)-1H-pyrazol) denoted complex 2 and depicted in FIG. 1, as suitable candidate for p-type doping of Spiro-MeOTAD.

Complex 2 has a redox potential of 0.95 V vs. NHE as determined by electrochemical measurements, which leaves a sufficient driving force of roughly 150 mV for the charge transfer reaction. Complex 2 and its $Co^{(II)}$ analog have almost no absorption in the visible region, which is an advantage in DSCs, because competition with the sensitizer for light harvesting in avoided.

Figure 2:
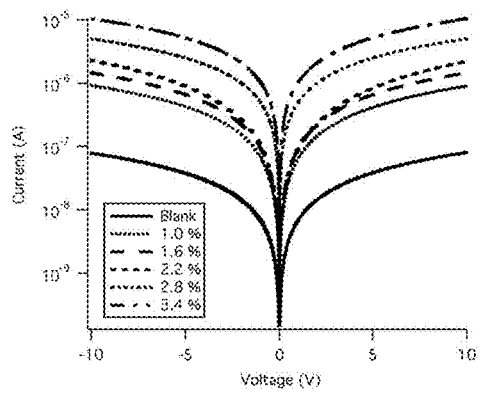
FIG. 2 shows the I-V characteristics of a spin-cast organic hole transporting material (Spiro-MeOTAD) to which a complex of the invention (complex 2) was added at different concentrations in the range of 1% to 3.4% as shown in the figure and in accordance with an embodiment of the invention. Doping ratios correspond to the molar percentage of complex 2 that has been added to a solution of Spiro-MeOTAD.
Figure 3:
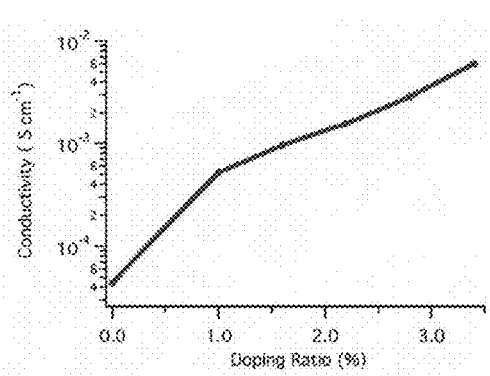
FIG. 3 shows the conductivity extracted from IV measurements of Spiro-MeOTAD films (FIG. 2) as function of level of doping with complex 2.

The basic mechanism of p-type doping is the creation of additional charge carriers (holes), leading to an increased charge carrier density in and therefore higher conductivity of the semiconductor film. This corresponds to results obtained from two-probe conductivity measurements showing an increase in conductivity from $4.4 \times 10^{-5}$ to $5.3 \times 10^{-4}$ S cm$^{-1}$ upon the addition of 1.0% complex 2. Snaith et al. (*Appl. Phys. Lett.* 2006, 89, 262114) previously reported a conductivity of $2.0 \times 10^{+5}$ S cm$^{-1}$ for the undoped Spiro-MeOTAD, a value that is in agreement with our findings, taking into account that a slightly different concentration of LiTFSI has been used. For higher doping concentrations, the conductivity increases exponentially with the doping ratio as shown in FIGS. 2 and 3. It has to be noted that given doping ratios correspond to the molar percentage of complex 2 that has been added to the Spiro-MeOTAD solution prior to spin-coating, but not necessarily to the resulting doping concentration within the amorphous film. This experiments show that complex 2 effectively dopes Spiro-MeOTAD.

Example 11: Preparation of a Solid State Dye-Sensitized Solar Cell

First, fluorine-doped tin-oxide (FTO) coated glass substrates (Tec15, Pilkington) were patterned by etching with zinc powder and 2 M hydrochloric acid. After cleaning, a $TiO_2$ compact layer was deposited on the substrates by aerosol spray pyrolysis at 450° C. using titanium diisopropoxide bis(acetylacetonate) dissolved in ethanol (1:10, volume ratio) as precursor and oxygen as carrier gas. After cooling to room temperature the substrates were treated in an 0.02 M aqueous solution of $TiCl_4$ for 30 min at 70° C., rinsed with deionized water and dried at 450° C. during 15 min. A 2.5 μm thick mesoporous $TiO_2$ layer composed of 20 nm sized particles was then deposited on the substrates by a screen-printing technique, dried at 125° C., gradually heated to 500° C. and then baked at this temperature for 15 min. The aforementioned treatment in aqueous $TiCl_4$ solution was repeated and the substrates again dried at 450° C. during 15 min. Prior to sensitization the $TiO_2$ substrates were heated to 500° C. during 30 min. After cooling to approximately 70° C. the substrates were immersed into a $10^{-4}$ M solution of the Y123 sensitizer (Tsao et al., ChemSusChem 2011, 4, 591-594) in a mixture of acetonitrile and tert-butyl alcohol (1:1, volume ratio) for 1 h. The hole-transporting material was deposited by spin-coating at 2000 rpm for 30 s. The formulation of the spin-coating solution was 0.15 M (2,2', 7,7'-tetrakis(N,N-di-p-methoxyphenylamine)-9,9-spirobifluorene) (Spiro-MeOTAD), 0.02 M Lithium bis(trifluoromethylsulfonyl)imide (LiTFSI) and 0.12 M 4-tert-butylpyridine (TBP) in chlorobenzene. When a chemical dopant was used, it was pre-dissolved in acetonitrile and added to the Spiro-MeOTAD solution prior to spin-coating.

In particular, three different doping ratios of 1.0%, 1.6% and 2.2% were investigated comparing them to an undoped reference (Blank).

Finally 200 nm of silver were thermally evaporated on top of the device to form the back contact. The devices were sealed using a 25 m thick polymer spacer (Surlyn, DuPont) and a microscopic cover slide.

Example 12: Device Characterization

Current-Voltage-Characteristics were recorded by applying an external potential bias to the cell while recording the generated photocurrent with a Keithley model 2400 digital source meter. The light source was a 450 W xenon lamp (Oriel) equipped with a Schott K113 Tempax sunlight filter (Praezisions Glas & Optik GmbH) in order to match the emission spectrum of the lamp to the AM 1.5 G standard (100 mW cm$^{-2}$). Incident photon-to-electron conversion efficiency (IPCE) spectra were recorded with a Keithley 2400 Source meter (Keithley) as function of wavelength under a constant white light bias of approximately 5 mW/cm$^2$ supplied by a white LED array. The excitation beam coming from a 300 W xenon lamp (ILC Technology) was focused through a Gemini-180 double monochromator (Jobin Yvon Ltd.) and chopped at approximately 4 Hz.

Figure 4:
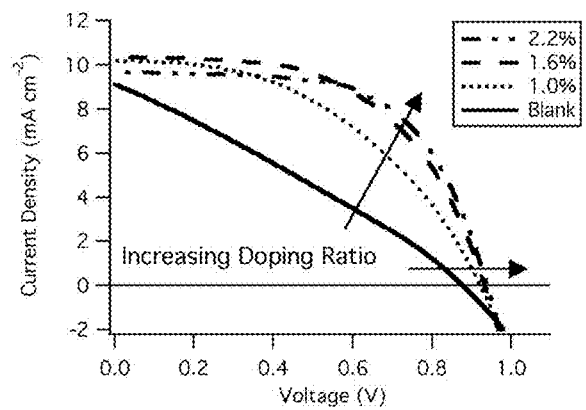
FIG. 4 shows J-V characteristics of ssDSCs containing different amounts of a dopant (complex 2) in accordance with the invention, compared to a device devoid of any dopant (Blank). Addition of the dopant in accordance with the invention mainly increases the fill factor and thus the performance of the device.

J-V characteristics measured under simulated AM1.5G solar irradiance (100 mW cm$^{-2}$) are represented in FIG. 4 and the extracted photovoltaic parameters summarized in Table 1 below.

TABLE 1

Photovoltaic parameters derived from J-V measurements for devices containing different doping ratios of complex 2 and an undoped reference (Blank).

|  |  |  | Blank | 1.0% | 1.6% | 2.2% |
|---|---|---|---|---|---|---|
| Initial Data | 10 mW cm$^{-2}$ | $V_{oc}$ (mV) | 808 | 846 | 845 | 846 |
|  |  | $J_{sc}$ (mA cm$^{-2}$) | 1.0 | 1.0 | 1.0 | 0.9 |
|  |  | FF | 0.66 | 0.75 | 0.77 | 0.77 |
|  |  | η (%) | 5.8 | 6.8 | 7.2 | 6.5 |
|  | 100 mW cm$^{-2}$ | $V_{oc}$ (mV) | 878 | 923 | 934 | 940 |
|  |  | $J_{sc}$ (mA cm$^{-2}$) | 9.1 | 10.2 | 10.4 | 9.6 |
|  |  | FF | 0.29 | 0.46 | 0.55 | 0.62 |
|  |  | η (%) | 2.3 | 4.3 | 5.3 | 5.6 |
| After 5 d | 100 mW cm$^{-2}$ | $V_{oc}$ (mV) | 887 | 925 | 943 | 947 |
|  |  | $J_{sc}$ (mA cm$^{-2}$) | 9.9 | 10.3 | 10.2 | 9.8 |
|  |  | FF | 0.30 | 0.54 | 0.63 | 0.65 |
|  |  | η (%) | 2.6 | 5.2 | 6.1 | 6.1 |

For the undoped reference we find an open-circuit potential $V_{OC}$, short-circuit current density $J_{SC}$ and fill factor FF of 878 mV, 9.1 mA cm$^{-2}$ and 0.29, respectively, yielding an overall PCE η of 2.3%. This device suffers from a relatively poor fill factor that can be attributed to the low conductivity and therefore high charge-transport resistance of the undoped spiro-MeOTAD film contributing to a high series resistance. Upon the addition of 1.0%, 1.6% and 2.2% of complex 2, the fill factor improves to 0.46, 0.55 and 0.62, respectively, resulting in power conversion efficiencies of 4.3%, 5.3% and 5.6%. Concerning the photo current density, the addition of FK102 leads to an increase of $J_{SC}$ to 10.2 mA cm$^{-2}$ (1.0% FK102) and 10.4 mA cm$^{-2}$ (1.6% FK102) and a subsequent decrease to 9.6 mA cm$^{-2}$ (2.2% FK102) at higher doping ratios. This decrease may be linked to a loss of current generation, as the oxidized species of Spiro-MeOTAD strongly absorb at 520 nm (c=4.01×10$^4$ mol$^{-1}$ cm$^{-1}$) and therefore compete with the sensitizer for light harvesting.

The open-circuit potential increases to 923 mV upon the addition of 1.0% complex 2 and surprisingly further increases to 934 and 940 mV when the doping ratio is raised to 1.6% and 2.2%, respectively. This may be due to a lowering of the Fermi level in the Spiro-MeOTAD film when the dopant is added, expanding the gap to the TiO$_2$ conduction band and therefore the maximum potential difference theoretically achievable. Moreover, a higher conductivity facilitates charge extraction and consequently obviates the accumulation of holes near the sensitized junction.

At full sunlight intensity (100 mW cm$^{-2}$) a maximum power conversion efficiency of 5.6% is achieved for the device containing 2.2% of complex 2. It is interesting to note that at low light intensity (10 mW cm$^{-2}$) the maximum is reached for a doping ratio of 1.6% yielding a remarkable PCE of 7.2% (Table 1).

In general we observe that the power conversion efficiency of solar cells based on the aforementioned system significantly increases over time when the devices are stored under dark. The comparison between J-V data measured several days after cell fabrication and the photovoltaic parameters initially obtained, reveals that this performance boost mainly results from an increase in FF (Table 1).

Devices based on the system presented herein generally reach power conversion efficiencies between 6-7% measured 1-2 weeks after their fabrication. For a champion device containing 1.6% of complex 2 dopant we achieved an unprecedented power conversion efficiency of 7.2% measured under simulated AM1.5G solar irradiance (100 mW cm$^{-2}$) (FIG. 5). To the best of our knowledge, this is the first time that such a high PCE has been obtained for an all solid-state dye-sensitized solar cell. For this device, we derive photovoltaic parameters $V_{OC}$, $J_{SC}$, and FF of 986 mV, 9.5 mA cm$^{-2}$ and 0.76, respectively, the corresponding J-V characteristics are illustrated in FIG. 4.

In conclusion we have shown that chemical p-type doping is an effective tool to tune the charge transport properties of spiro-MeOTAD in solid-state DSCs and capable of replacing commonly employed photo-doping. Preliminary studies demonstrate that the reported Co$^{(III)}$ complex (complex 2) fulfils the necessary requirements for this kind of application and promising results could have been achieved.

Example 13: Synthesis of copper 2,2'-dimethyl phenanthroline trifluoromethanesulfonimide (Cu(I))(dmp)$_2$(TFSI) (1) and (Cu(II)(dmp)$_2$(TFSI)$_2$ (96)

The synthesis is based on the synthesis for copper 2,2'-dimethyl phenanthroline described in Energy Environ. Sci., 2015, 8, 2634-2637. For (Cu(dmp)$_2$TFSI) (1), one equivalent of CuI (35 mg, 0.175 mmol) was mixed with 4 equivalents of Neocuproine hydrate (100 mg, 0.7 mmol) in ethanol, under nitrogen atmosphere, at room temperature for 2 hours. Complex (1) was collected by filtration and washed with water and diethyl ether. The resulted complex (1) was obtained as intense red, crystalline powder. The yield was 90% (0.16 mmol). For Cu(dmp)$_2$(TFSI)$_2$ (96), Complex (1) (100 mg, 0.13 mmol) was dissolved in acetonitrile. To this solution, 1 equivalent of NOBF$_4$ (16 mg, 0.13 mmol) followed with 5 equivalents of LiTFSI (37 mg, 0.65 mmol) were added after 30 min. The solution was further stirred for 2 hours at room temperature and under nitrogen atmosphere. The solvent was removed by rotary evaporation and the crude re-dissolved in minimum amount of dichloromethane. Complex (96) was collected by filtration after precipitation from diethylether and washed with diethyl ether. The yield was 72% (mol). The product was a bright violet powder. (see FIG. 1)

$^1$H NMR (400 MHz, acetone d6): δ 8.75 (d, J(H—H)=8.21 Hz, 1H), 8.23 (s, 1H), 7.98 (d, J(H—H)=8.24 Hz, 1H), 2.52 (s, 3H).

Example 14: Effect of the (Cu(II)(Dmp)$_2$(TFSI)$_2$ (96) Complex of the Invention as Dopant for Hole Transport Material Complex of formula (96) used as dopant was added in the hole transport layer comprising spiro-OMeTAD as hole transport material of a perovskite solar cell based on methylammonium lead iodide perovskite light absorber.

Preparation of Perovskite Solar Cell Devices

A compact TiO$_2$ layer of 20 nm thick was deposited on top of FTO coated glass via spray pyrolysis at 450° C. from a precursor solution of titanium diisopropoxide bis(acetylacetonate) in anhydrous ethanol. On top of this compact layer a mesoporous TiO$_2$ layer of 150-200 nm was deposited by the spin-coating method, applying 30 nm particle paste (Dyesol 30 NR-D) diluted in ethanol. The substrates were immediately dried at 100° C. for 10 min and then sintered again at 450° C. for 30 min under dry air flow. After cooling down to 150° C. the substrates were immediately transferred to a nitrogen atmosphere glove box for depositing the perovskite films. The perovskite films were deposited from a precursor solution containing MAI (1 M), PbI$_2$ (1 M), in anhydrous DMSO. The perovskite solution was spin coated in a two steps procedure at 1000 and 4000 rpm for 10 and 30 s respectively. During the second step, 100 μL of Chlorobenzene was added on top of the spinning substrate 10 s prior to ending the spin coating. The substrates were then annealed at 100° C. for 1 hour in a nitrogen filled glove box. After that the substrates were cooled down for few minutes and a Hole transporting material doped with complex of formula (96) solution (70 mM in chlorobenzene) was spun at 4000 rpm for 20 s. Finally 70-80 nm of gold as a top contact was thermally evaporated under high vacuum.

Photovoltaic Properties Characterisation of Perovskite Solar Cell

The perovskite solar cells were measured using a 450 W xenon light source (Oriel). The light intensity was calibrated with a Si photodiode equipped with an IR-cutoff filter (KG3, Schott) and it was recorded during each measurement. Current-voltage characteristics of the cells were obtained by applying an external voltage bias while measuring the current response with a digital source meter (Keithley 2400). The voltage scan rate was 10 mV s$^{-1}$. The cells were masked with a black metal mask (0.16 cm$^2$) to estimate the active area and reduce the influence of the scattered light.

The spiro-OMeTAD comprise in the HTL of a perovskite solar cell was doped with only 3% of complex of formula (96) This perovskite solar cell is compared with a perovskite solar cell, which does not contain doped hole transport material. The photovoltaic parameters are reported in Table 2.

TABLE 2

PV parameters of devices with and without the Cu dopant in the HTL

|  | $V_{oc}$ | $J_{sc}$ | FF | PCE |
|---|---|---|---|---|
| HTL no doped | 995 | 16.9 | 0.33 | 5.7 |
| HTL doped with 3% Cu complex | 1092 | 19.3 | 0.71 | 15.4 |

Example 14: Effect of the Optimization of the HTL with Additives (Tert-Butyl Pyridine and Lithium Salts) in the Perovskite Solar Cell of the Invention HTLs have been optimized with other additives such as tert-butyl pyridine and Lithium salts. The role of these additives is still under debate. And perovskite solar cells use them in conjunction with doped hole transport material.

Figure 19:
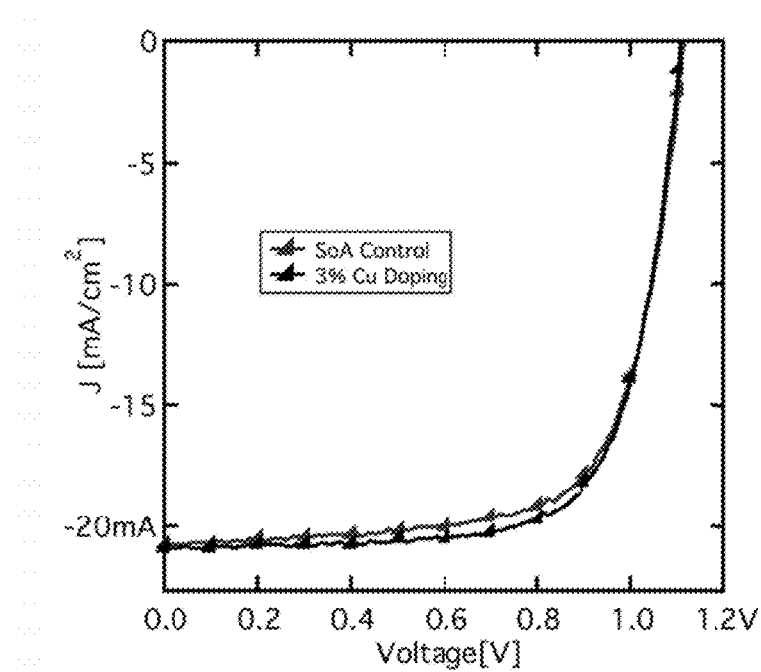
FIG. 19 shows J-V curves of perovskite solar cells with HTM doped with a tris(2-(1H-pyrazol-1-yl)-4-tert-butylpyridine)-cobalt(III) tris(bis(trifluoromethylsulfonyl)imide) complex (FK-209) (top curve in dark grey) or with a copper (II) 2,2'-dimethyl 1,10-phenanthroline trifluoromethanesulfonimide (Cu(II)(dmp)$_2$(TFSI)$_2$ complex (bottom curve in black) of the invention. In both devices, HTL further comprises Lithium salt and TBP.

FIG. 19 shows J-V curves of two perovskite solar cells containing HTM (spiro-OMeTAD) doped with either a Cobalt complex (tris(2-(1H-pyrazol-1-yl)-4-tert-butylpyridine)-cobalt(III) tris(bis(trifluoromethylsulfonyl)imide) (FK209, from Dyenamo) or a Cu(II) complex of formula (96) of the present invention. Lithium salt (bis(trifluoromethylsulfonyl)imide lithium salt (Li-TFSI)) is added in HTL comprising spiro-OMeTAD doped with Co complex and 4-tert-Butylpyridine (TBP) is added in HTL comprising spiro-OMeTAD doped with Cu(II) complex of the invention. The molar ratio of additives with respect to spiro-OMeTAD (0.08M) was: 0.5, 0.03 and 3.3 for Li-TFSI, FK209/Copper (II) complex and TBP, respectively. The fabrication of devices was done as described above.

TABLE 3

Photovoltaic parameters of devices having HTL doped with Co complex (FK-209) or Cu complex of formula (96) as dopant and additives

|  | Voc (mV) | Jsc (mA/cm2) | FF | PCE (%) |
|---|---|---|---|---|
| HTL with Co complex as dopant and additives | 1118 | 20.7 | 0.69 | 16.5 |
| HTL with Cu complex as dopant and additives | 1128 | 20.8 | 0.71 | 16.8 |

From Table 3, the performances of the device with copper complex as dopant are comparable to those of the device with Co complex as dopant. Thus the fact that the copper complex doping provides comparable photovoltaic performance supports that copper complex doping can advantageously replace Co complex doping. In particular, the copper complexes are easily synthesizable and at lower cost and present a low environment impact because they are nontoxic compared to the Co complexes. These advantages will besides favor for the industrial production of copper complexes.

Example 16: Cu(II) Complexes Used as HTM in Perovskite Solar Cells

Various Cu(II) complexes having different redox potentials have been tested as HTM (without Spiro-OMeTAD).

HTLs of the tested devices comprise 0.2 M Copper(I) complex, 0.04 M Copper (II) complex, the complexes used in this experiment were, 4-ethoxy-6,6'-dimethyl-2,2'-bipyridine trifluoromethanesulfonimide $(Cu(I)(eto)_2(TFSI)$ and $(Cu(II)(eto)_2(TFSI)_2$, 2, dibenzo[b, j][1,10]phenanthroline trifluoromethanesulfonimide $(Cu(I)(bi)_2(TFSI)$ and $(Cu(II)(bi)_2(TFSI)_2$, 2,9-diphenyl-1,10-phenanthroline trifluoromethanesulfonimide $(Cu(I)(pp)_2(TFSI)$ and $(Cu(II)(pp)_2(TFSI)_2$, and 0.5 M 4-tert-Butylpyridine, or 0.2M 2,2'-dimethyl phenanthroline trifluoromethanesulfonimide $(Cu(II)(dmp)_2(TFSI)_2$, (as HTM). 0.5M TBP 0.1 M LiTFSI were also added as additive to the HTM solution. The experimental procedure for the device fabrication was the same of example 14.

The solar cells were measured using a 450 W xenon light source (Oriel). The light intensity was calibrated with a Si photodiode equipped with an IR-cutoff filter (KG3, Schott) and it was recorded during each measurement. Current-voltage characteristics of the cells were obtained by applying an external voltage bias while measuring the current response with a digital source meter (Keithley 2400). The voltage scan rate was 10 mV s$^{-1}$. The cells were masked with a black metal mask (0.16 cm$^2$) to estimate the active area and reduce the influence of the scattered light.

Figure 20:
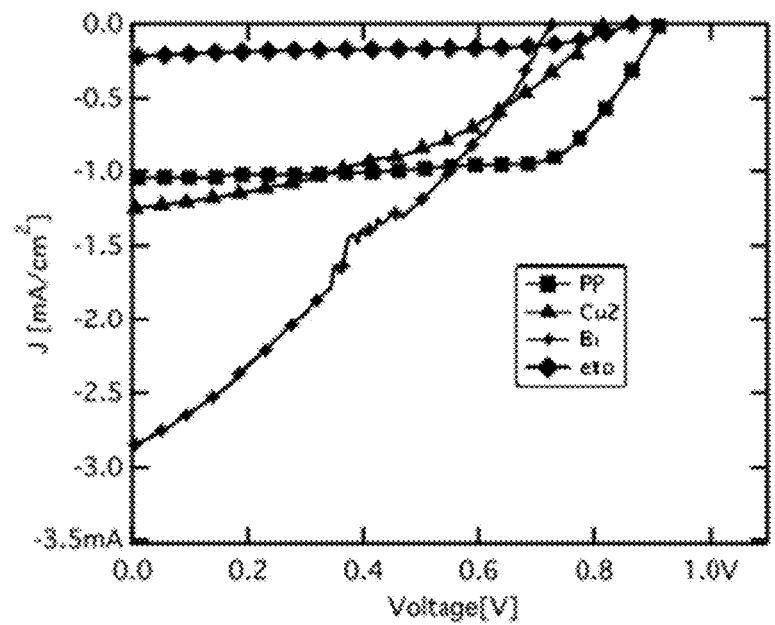
FIG. 20 shows J-V curves of perovskite solar cells comprising various copper complexes of the invention having different redox potentials as HTMs. HTLs (Hole Transporting Layers) of the tested devices comprise 0.2 M Copper(I) complex, 0.04 M Copper (II) complex. 1) Diamond curve: Copper(I/II) 4-ethoxy-6,6'-dimethyl-2,2'-bipyridine trifluoromethanesulfonimide (Cu(I)(eto)$_2$(TFSI) and (Cu(II)(eto)$_2$(TFSI)$_2$ (named "eto"). 2) Small diamond curve: copper(I/II) dibenzo[b, j][1,10]phenanthroline trifluoromethanesulfonimide (Cu(I)(bi)$_2$(TFSI) and (Cu(II)(bi)$_2$(TFSI)$_2$ (named "bi"). 3) square curve: copper(I/II) 2,9-diphenyl-1,10-phenanthroline trifluoromethanesulfonimide (Cu(I)(pp)$_2$(TFSI) and (Cu(II)(pp)$_2$(TFSI)$_2$ (named "pp"). 4) triangle curve: 0.5 M 4-tert-Butylpyridine or 0.2M 2,2'-dimethyl phenanthroline trifluoromethanesulfonimide (Cu(II)(dmp)$_2$(TFSI)$_2$ (named "Cu2").

The results presented in FIG. 20 show that Cu(II) complexes do not work as HTM in a perovskite solar cell of the invention.

The invention claimed is:

1. A p-dopant comprising a complex of formula (XX)

$$M(La)_n(Xb)_m \quad (XX)$$

wherein
M is selected from $Cu^{2+}$, $Pd^{2+}$, $Au^{2+}$, $Ag^{2+}$, and $V^{2+}$;
n is an integer selected from 1, 2, 3 or 4;
m is an integer selected from 0, 1, 2, or 3;
La is a ligand independently selected from mono-, bi-, or tridentate ligands comprising a moiety independently selected from a moiety according to any one of formulae (XX-1)-(XX-5) and (XX-8)-(XX-69)

(XX-1)

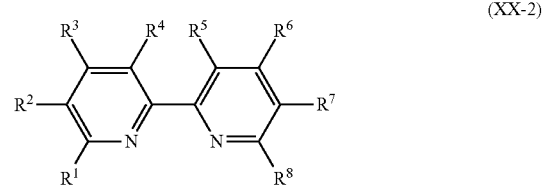

(XX-2)

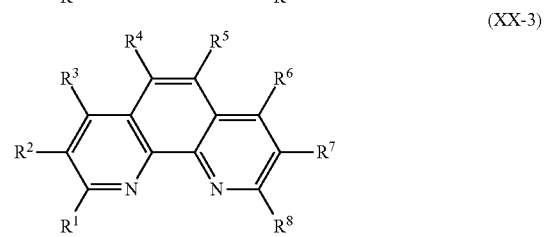

(XX-3)

-continued
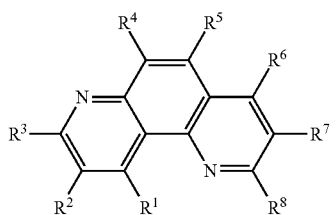 (XX-4)
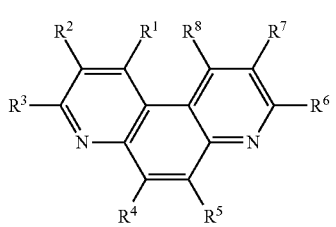 (XX-5)
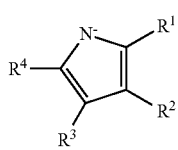 (XX-8)
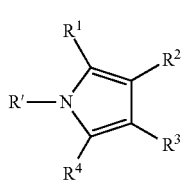 (XX-9)
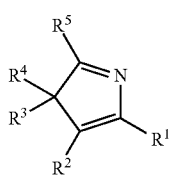 (XX-10)
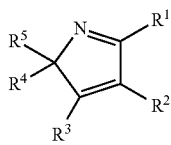 (XX-11)
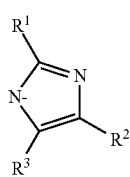 (XX-12)
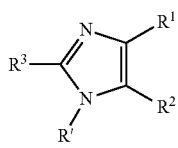 (XX-13)
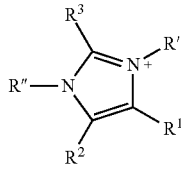 (XX-14)
-continued
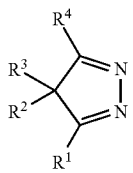 (XX-15)
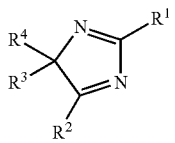 (XX-16)
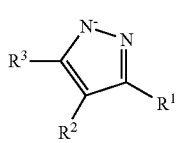 (XX-17)
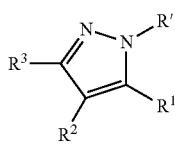 (XX-18)
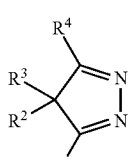 (XX-19)
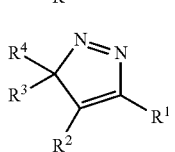 (XX-20)
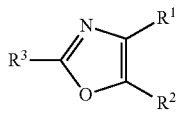 (XX-21)
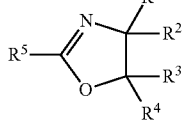 (XX-22)
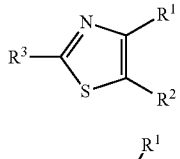 (XX-23)
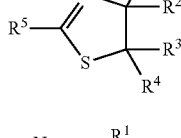 (XX-24)
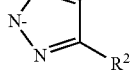 (XX-25)

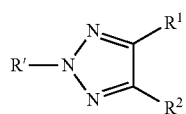 (XX-26)
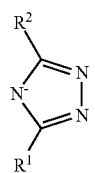 (XX-27)
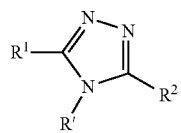 (XX-28)
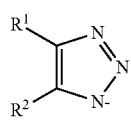 (XX-29)
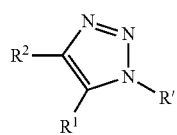 (XX-30)
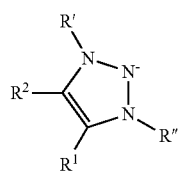 (XX-31)
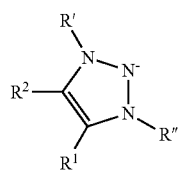 (XX-32)
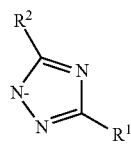 (XX-33)
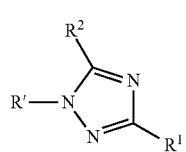 (XX-34)
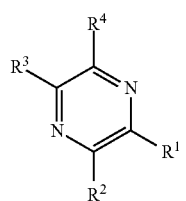 (XX-35)
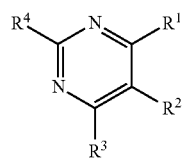 (XX-36)
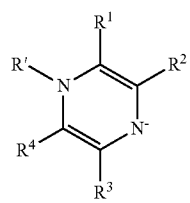 (XX-37)
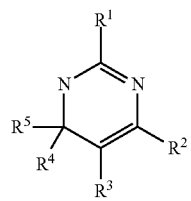 (XX-38)
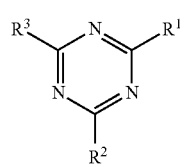 (XX-39)
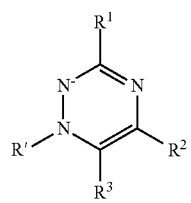 (XX-40)
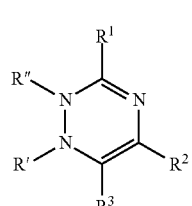 (XX-41)
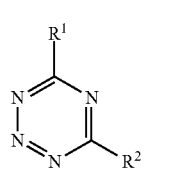 (XX-42)
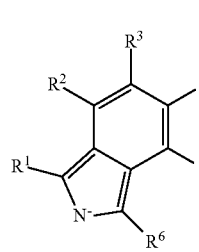 (XX-43)

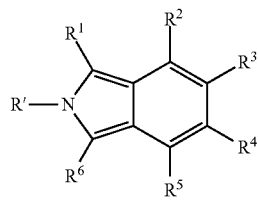 (XX-44)
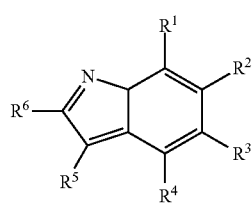 (XX-45)
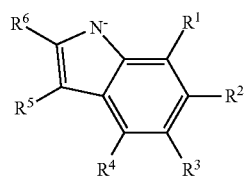 (XX-46)
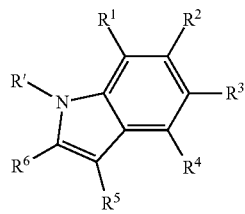 (XX-47)
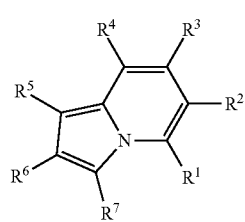 (XX-48)
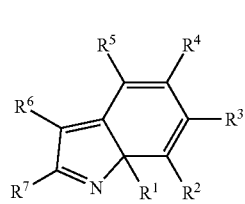 (XX-49)
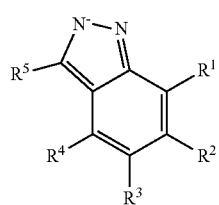 (XX-50)
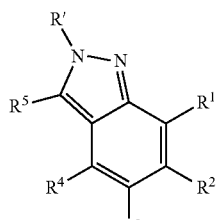 (XX-51)
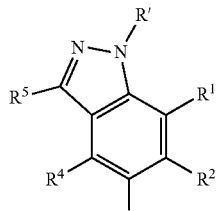 (XX-52)
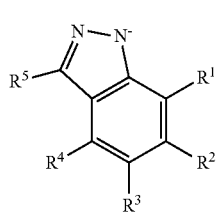 (XX-53)
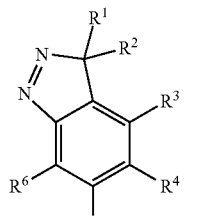 (XX-54)
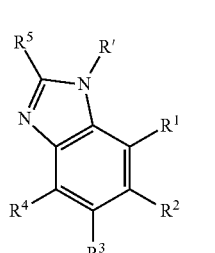 (XX-55)
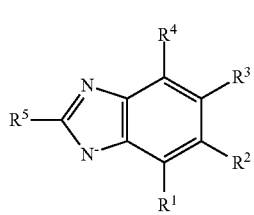 (XX-56)
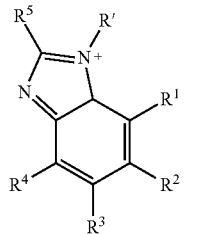 (XX-57)

(XX-58) 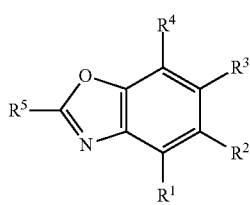

(XX-59) 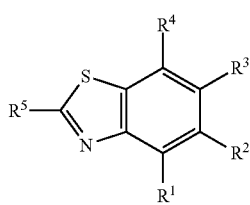

(XX-60) 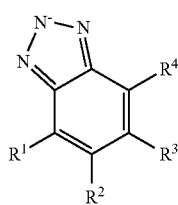

(XX-61) 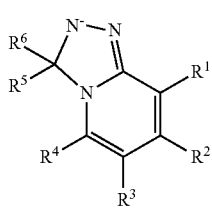

(XX-62) 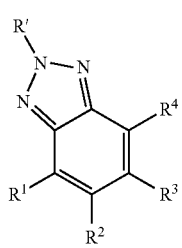

(XX-63) 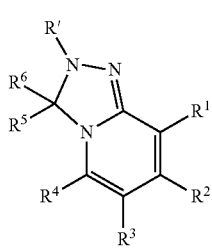

(XX-64) 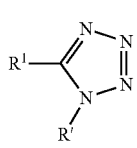

(XX-65) 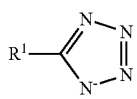

(XX-66) 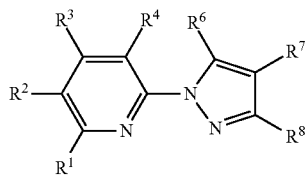

(XX-67) 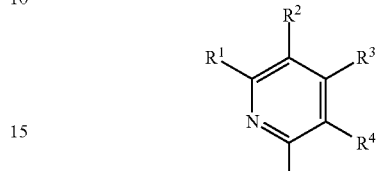

(XX-68) 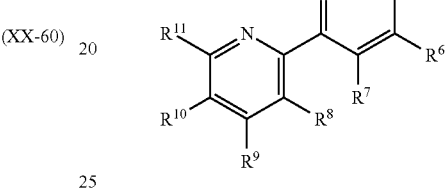

(XX-69) 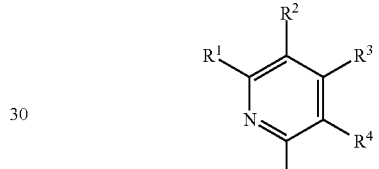

wherein:

$R^1$, $R^2$, $R^3$, $R^4$, $R^5$, $R^6$, $R^7$, $R^8$, $R^9$, $R^{10}$, $R^{11}$ and $R^{12}$ of moieties (XX-1)-(XX-5) and (XX-8)-(XX-69) are independently selected from H, halogen, Cl—, Br—, I⁻, —NO₂, —OH, —NH₂, —COOH, —CN, —OCN—, isocyanate group, sulfonyl group, from C1-C6 alkyl, C1-C6 heteroalkyl, C4-C20 aryl group, C4-C20 arylalkyl group and C4-C20 heteroaryl group, wherein heteroatom is selected from N, S, or O, said alkyl, heteroalkyl, arylalkyl and heteroaryl groups being optionally perfluorinated, and from a moiety according to any one of formulae (XXA-1) to (XXG-2) below:
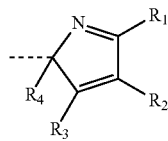
(XXA-1)
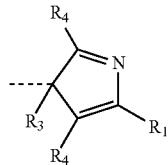
(XXA-2)
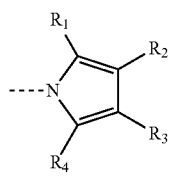
(XXA-3)
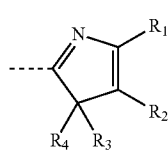
(XXA-4)
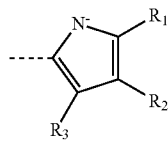
(XXA-5)
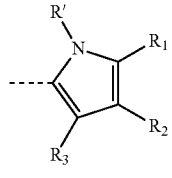
(XXA-6)
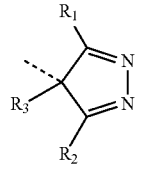
(XXB-1)
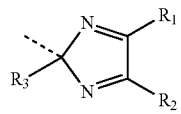
(XXB-2)
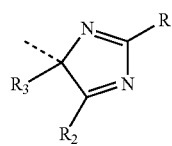
(XXB-3)
-continued
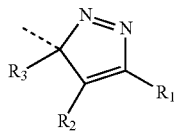
(XXB-4)
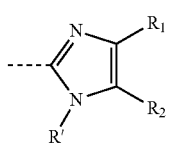
(XXB-5)
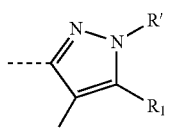
(XXB-6)
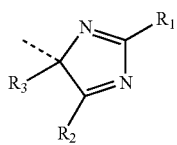
(XXB-7)
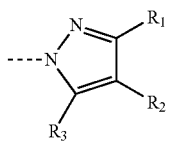
(XXB-8)
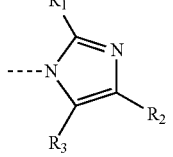
(XXB-9)
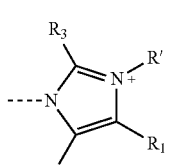
(XXB-10)
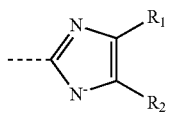
(XXB-11)
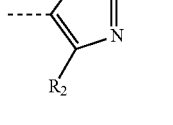
(XXB-12)
(XXB-13)

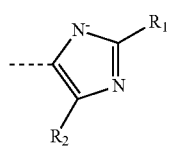 (XXB-14)
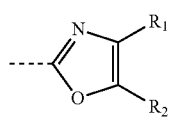 (XXB-15)
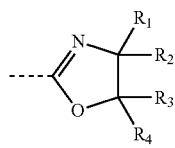 (XXB-16)
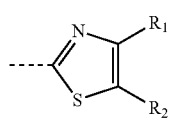 (XXB-17)
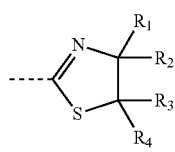 (XXB-18)
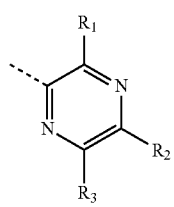 (XXB-21)
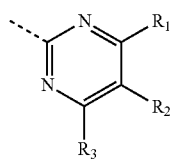 (XXB-22)
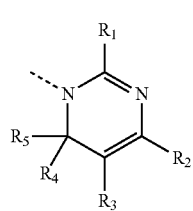 (XXB-23)
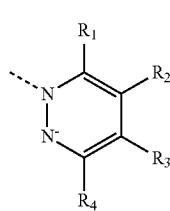 (XXB-24)
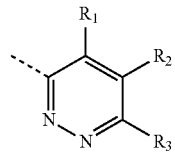 (XXB-25)
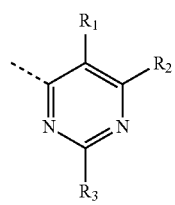 (XXB-26)
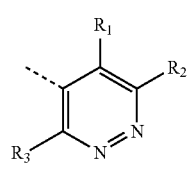 (XXB-27)
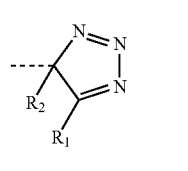 (XXC-1)
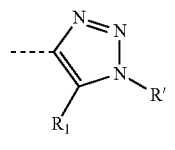 (XXC-2)
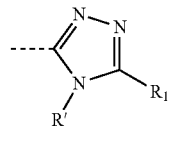 (XXC-3)
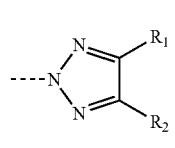 (XXC-4)
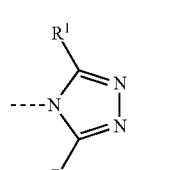 (XXC-5)
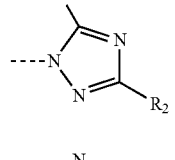 (XXC-6)
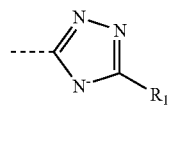 (XXC-7)

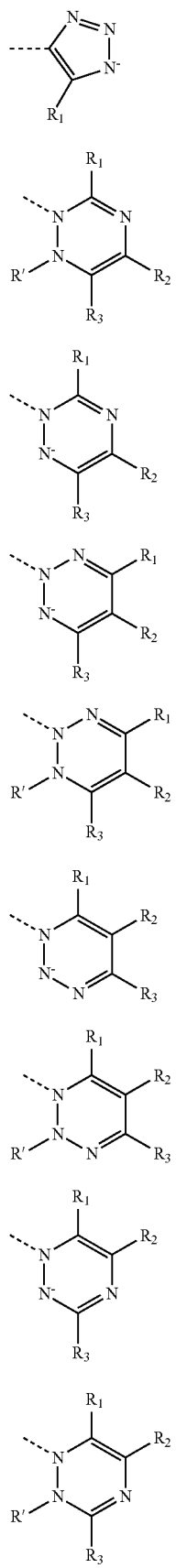
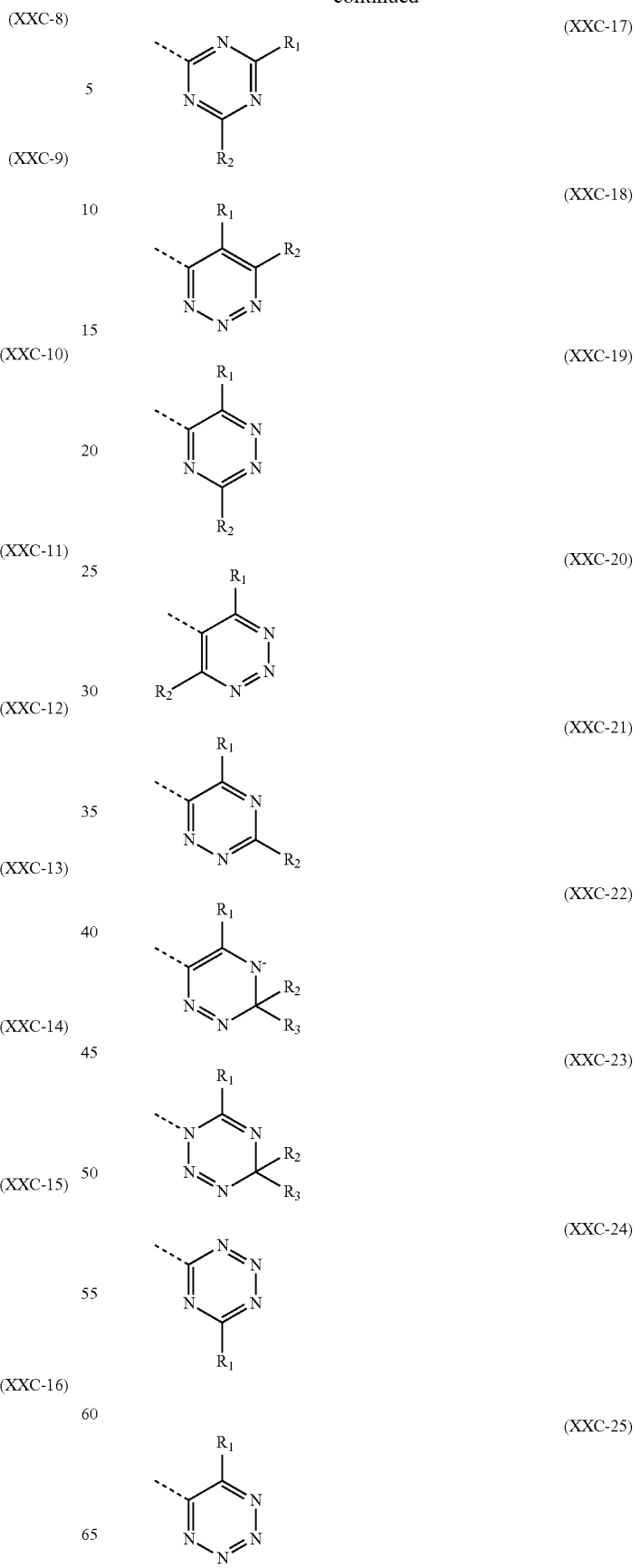

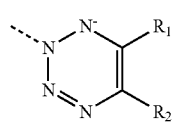 (XXC-26)
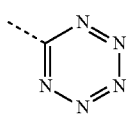 (XXC-27)
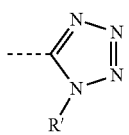 (XXD-1)
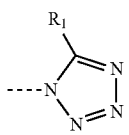 (XXD-2)
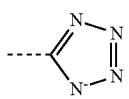 (XXD-3)
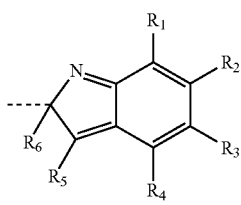 (XXE-1)
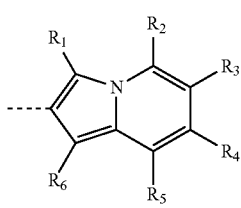 (XXE-2)
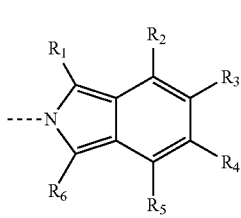 (XXE-3)
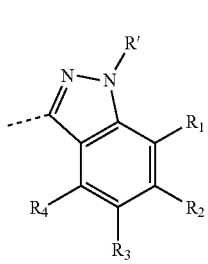 (XXF-1)
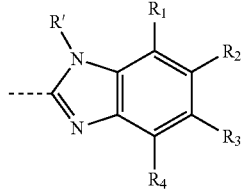 (XXF-2)
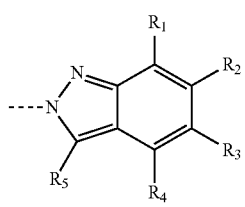 (XXF-3)
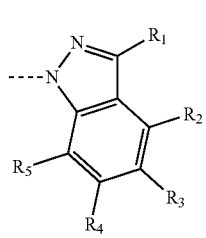 (XXF-4)
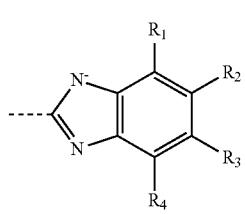 (XXF-5)
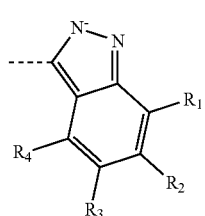 (XXF-6)
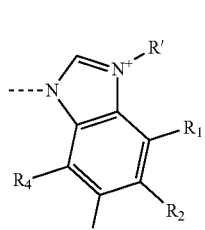 (XXF-7)
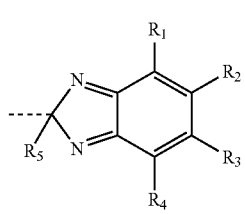 (XXF-8)

-continued

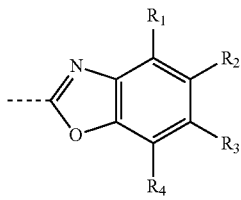
(XXF-9)

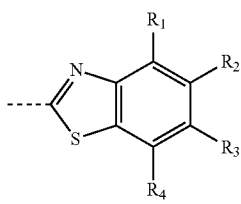
(XXF-10)

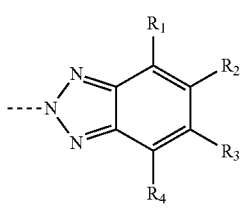
(XXG-1)

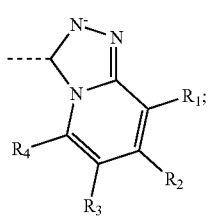
(XXG-2)

wherein:
the dotted line represents the bond connecting the substituent of (XXA-1) to (XXG-2) on the ligand La according to any one of formulae (XX-1)-(XX-5) and (XX-8)-(XX-69); and, $R_1$, $R_2$, $R_3$, $R_4$, $R_5$, and $R_6$ of moieties (XXA-1) to (XXG-2) are independently selected from H, halogen, Cl⁻, Br⁻, I⁻, —NO$_2$, —OH, —NH$_2$, —COOH, —CN, —OCN⁻, isocyanate group, sulfonyl group and substituents comprising 1 to 40 carbons and 0 to 20 heteroatoms and/or groups selected from —O—, —C(O)—, —C(O)O—, —S—, —S(O)—, SO$_2$—, —S(O)$_2$O—, —N=, —P=, —NR$^{13}$—, —PR$^{13}$—, —P(O)(OR$^{13}$)—, —P(O)(OR$^{13}$)O—, —P(O)(NR$^{13}$R$^{13}$)—, —P(O)(NR$^{13}$R$^{13}$)O—, —P(O)(NR$^{13}$R$^{13}$)NR$^{13}$—, —S(O)NR$^{13}$—, and —S(O)$_2$NR$^{13}$, with R$^{13}$ being independently selected from H, C1-C6 alkyl, C4-C20 aryl group, C4-C20 arylalkyl group and C4-C20 heteroaryl group, said alkyl, arylalkyl and heteroaryl groups being optionally perfluorinated;

R' and R" are independently selected from —CH$_2$R$^1$, —CHR$^1$R$^2$ and —CR$^1$R$^2$R$^3$, R$^1$, R$^2$ and R$^3$ being defined as above; and Xb is a monodentate co-ligand independently selected from H$_2$O, Cl⁻, Br⁻, I⁻, CN⁻, NCO⁻, NCS⁻, NCSe, NH$_3$, NR$_7$R$_8$R$_9$, or PR$_7$R$_8$R$_9$, wherein R$_7$, R$_8$, and R$_9$ are selected independently from substituted or unsubstituted C1-C20 alkyl, C2-C20 alkenyl, C2-C20 alkynyl, and C4 to C20 aryl.

2. The p-dopant according to claim 1, wherein the complex of formula (XX) is under cationic form and provided with an anionic species independently selected from ClO$_4$⁻, PF$_6$⁻, BF$_4$⁻, [B(CN)$_4$]⁻, CF$_3$SO$_3$⁻, [(CF$_3$SO$_2$)$_2$N]⁻ (TFSI), [B(C$_6$H$_3$(m-CF$_3$)$_2$)$_4$]⁻, [B(C$_6$F$_5$)$_4$]⁻, [B(C$_6$H$_5$)$_4$]⁻, [Al(OC(CF$_3$)$_3$)$_4$]⁻, or [CB$_{11}$H$_{12}$]⁻.

3. The p-dopant according to claim 1, wherein M of the complex of formula (XX) is Cu'.

4. The p-dopant according to claim 1, wherein n of the complex of formula (XX) is 2, 3 or 4.

5. The p-dopant according to claim 1, wherein, provided that n of the complex of formula (XX) is 2, said La ligands of the complex of formula (XX) are identical or different from each other.

6. The p-dopant according to claim 1, wherein m of the complex of formula (XX) is 0.

7. The p-dopant according to claim 1, wherein La of the complex of formula (XX) is a ligand selected from a moiety according to any one of formulae (XX-1)-(XX-5) and (XX-66) to (XX-69).

8. The p-dopant according to claim 1, wherein, provided that m is 0, the complex of formula (XX) is selected from a complex according to any one of formulae (XXIII) to (XXV)

M L1 L2 L3 L4     (XXIII), wherein L1, L2, L3 and L4 are selected from monodentate ligands,

M L1 L2 L3     (XXIV), wherein L1 and L2 are selected from monodentate ligands and L3 is selected from bidentate ligands,

M L1 L2     (XXV), wherein L1 and L2 are selected from bidentate ligands, or L1 is selected from monodentate ligands and L2 is selected from tridentate ligands;
wherein said mono-, bi-, or tridentate ligands are independently selected from La ligand.

9. The p-dopant according to claim 1, wherein the complex of formula (XX) is selected from a complex according to any one of formulae (XXI) and (XXII)

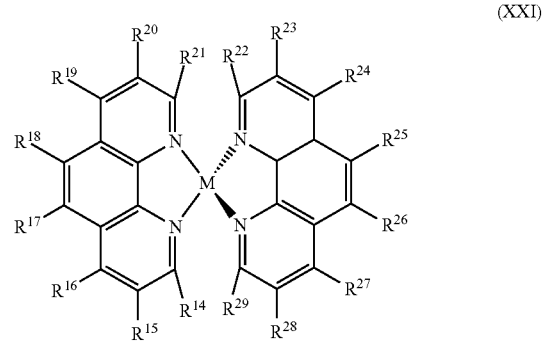
(XXI)

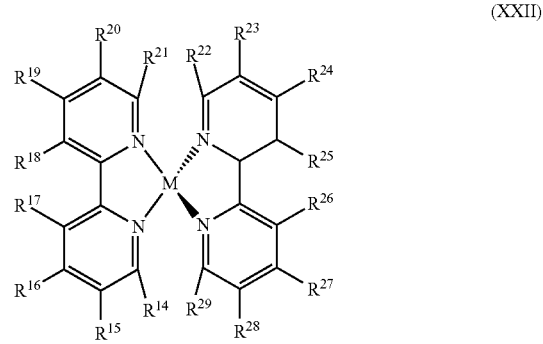
(XXII)

wherein, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$ of complexes (XXI)-(XXII) are independently selected from H, halogen, Cl—, Br—, I⁻, —NO₂, —OH, —NH₂, —COOH, —CN, —OCN—, isocyanate group, sulfonyl group, from C1-C6 alkyl, C1-C6 heteroalkyl, C4-C20 aryl group, C4-C20 arylalkyl group and C4-C20 heteroaryl group, wherein heteroatom is selected from N, S, or O, said alkyl, heteroalkyl, arylalkyl and heteroaryl groups being optionally perfluorinated, and from a moiety according to any one of formulae (XXA-I) to (XXG-2) below:

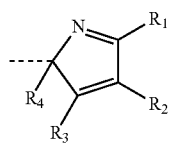
(XXA-1)

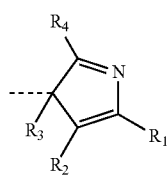
(XXA-2)

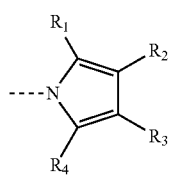
(XXA-3)

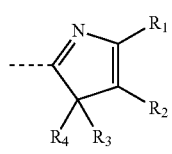
(XXA-4)

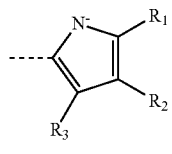
(XXA-5)

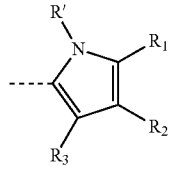
(XXA-6)

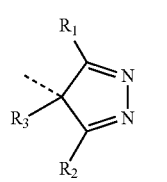
(XXB-1)

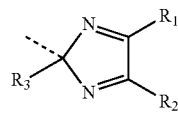
(XXB-2)

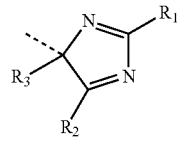
(XXB-3)

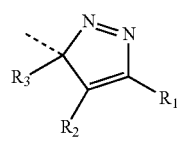
(XXB-4)

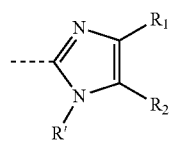
(XXB-5)

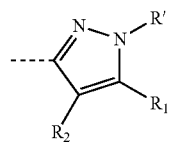
(XXB-6)

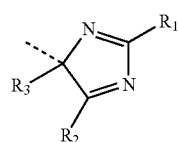
(XXB-7)

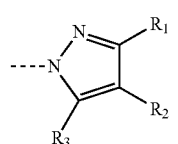
(XXB-8)

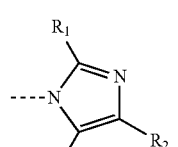
(XXB-9)

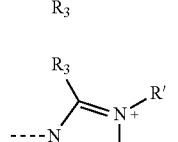
(XXB-10)

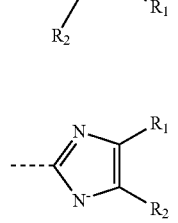
(XXB-11)

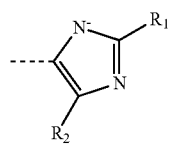 (XXB-12)
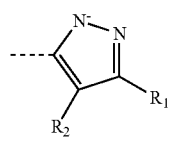 (XXB-13)
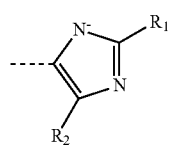 (XXB-14)
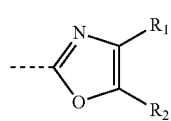 (XXB-15)
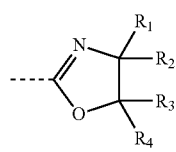 (XXB-16)
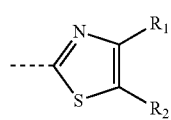 (XXB-17)
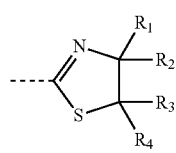 (XXB-18)
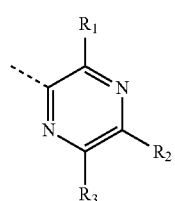 (XXB-21)
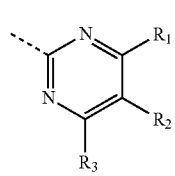 (XXB-22)
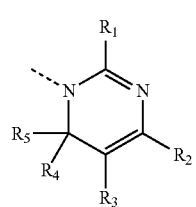 (XXB-23)
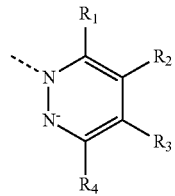 (XXB-24)
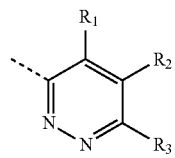 (XXB-25)
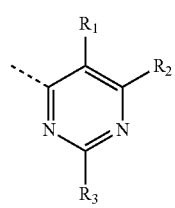 (XXB-26)
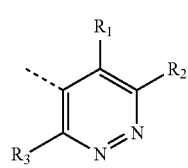 (XXB-27)
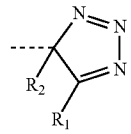 (XXC-1)
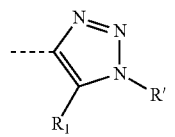 (XXC-2)
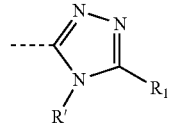 (XXC-3)
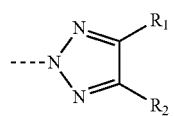 (XXC-4)
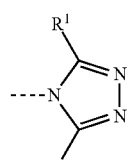 (XXC-5)
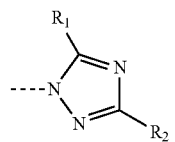 (XXC-6)

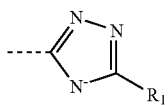 (XXC-7)
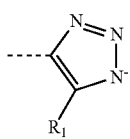 (XXC-8)
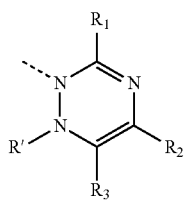 (XXC-9)
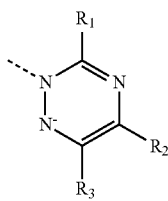 (XXC-10)
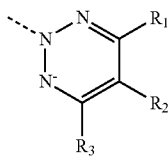 (XXC-11)
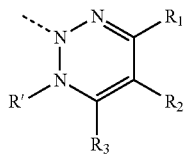 (XXC-12)
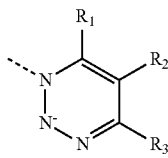 (XXC-13)
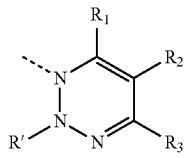 (XXC-14)
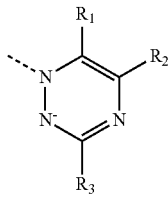 (XXC-15)
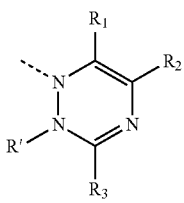 (XXC-16)
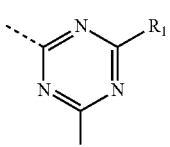 (XXC-17)
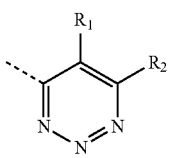 (XXC-18)
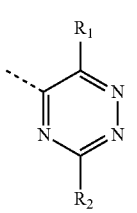 (XXC-19)
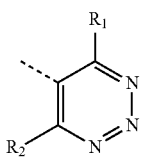 (XXC-20)
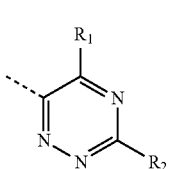 (XXC-21)
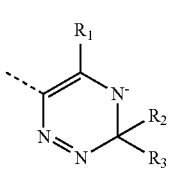 (XXC-22)
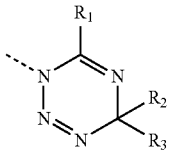 (XXC-23)
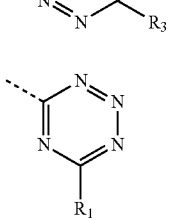 (XXC-24)

(XXC-25) 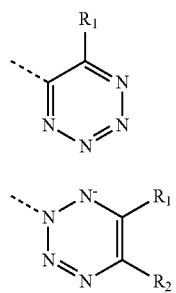
(XXC-26) 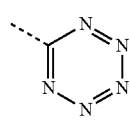
(XXC-27) 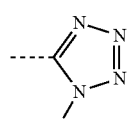
(XXD-1) 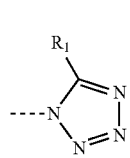
(XXD-2) 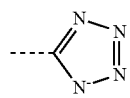
(XXD-3) 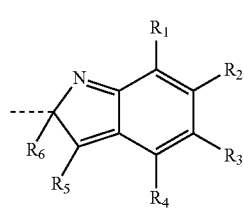
(XXE-1) 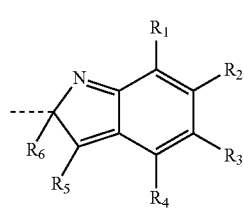
(XXE-2) 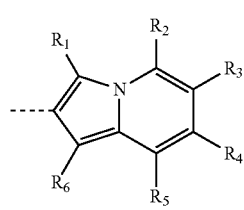
(XXE-3) 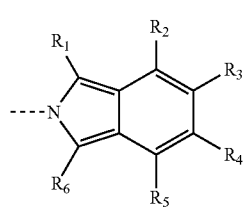
(XXF-1) 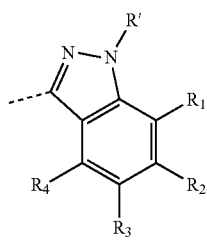
(XXF-2) 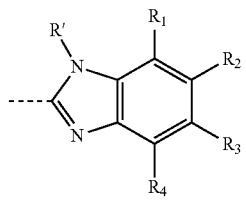
(XXF-3) 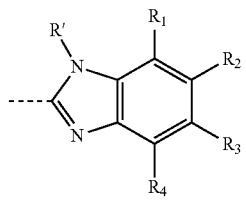
(XXF-4) 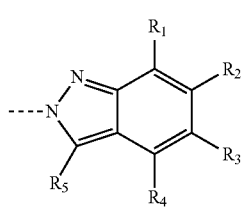
(XXF-5) 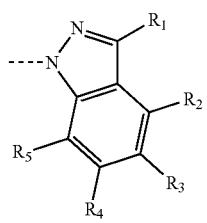
(XXF-6) 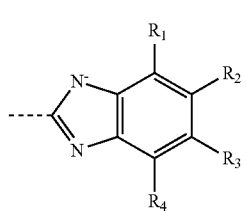
(XXF-7) 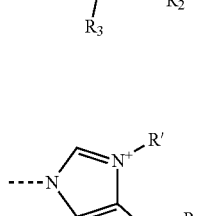

-continued

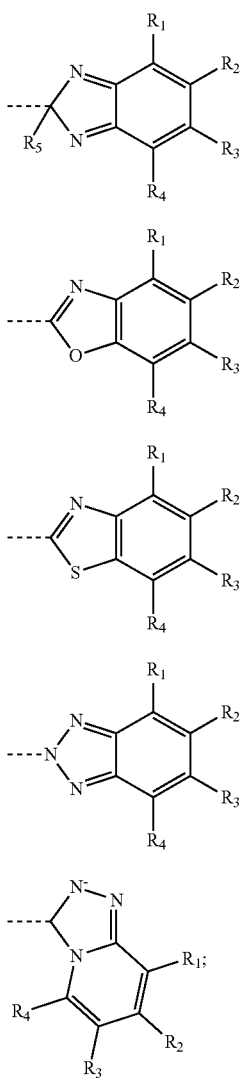

wherein:
the dotted line represents the bond connecting the substituent of (XXA-1) to (XXG-2) on the ligand La according to any one of formulae (XX-1)-(XX-5) and (XX-8)-(XX-69); and,
$R_1$, $R_2$, $R_3$, $R_4$, $R_5$, and $R_6$ of moieties (XXA-1) to (XXG-2) are independently selected from H, halogen, Cl⁻, Br⁻, I⁻, -NO₂, —OH, —NH₂, —COOH, —CN, —OCN⁻, isocyanate group, sulfonyl group and substituents comprising 1 to 40 carbons and 0 to 20 heteroatoms and/or groups selected from O—, —C(O)—, —C(O)O—, —S—, —S(O)—, SO₂—, —S(O)₂O—, —N═, —P═, —NR¹³—, —PR¹³—, —P(O)(OR¹³)—, —P(O)(OR¹³)O—, —P(O)(NR¹³R¹³)—, —P(O)(NR¹³R¹³)O—, —P(O)(NR¹³R¹³)NR¹³—, —S(O)NR¹³—, and S(O)₂NR¹³, with R¹³ being independently selected from H, C1-C6 alkyl, C4-C20 aryl group, C4-C20 arylalkyl group and C4-C20 heteroaryl group, said alkyl, arylalkyl and heteroaryl groups being optionally perfluorinated.

10. An electrochemical and/or optoelectronic device being a solid state solar cell comprising the p-dopant as defined in claim 1.

11. The electrochemical and/or optoelectronic device according to claim 10, wherein the p-dopant comprises a complex being selected from a complex according to any one of formulae (XXI) and (XXII)

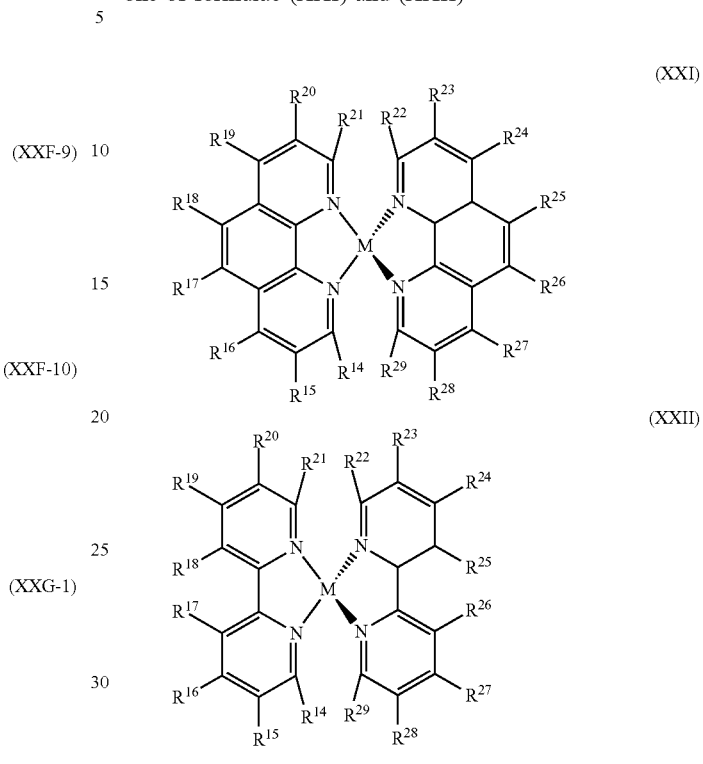

wherein,
$R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$ of complexes (XXI)-(XXII) are independently selected from H, halogen, Cl—, Br—, I⁻, —NO₂, —OH, —NH₂, —COOH, —CN, —OCN—, isocyanate group, sulfonyl group, from C1-C6 alkyl, C1-C6 heteroalkyl, C4-C20 aryl group, C4-C20 arylalkyl group and C4-C20 heteroaryl group, wherein heteroatom is selected from N, S, or O, said alkyl, heteroalkyl, arylalkyl and heteroaryl groups being optionally perfluorinated, and from a moiety according to any one of formulae (XXA-1) to (XXG-2) below:

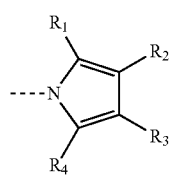 (XXA-3)
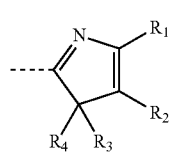 (XXA-4)
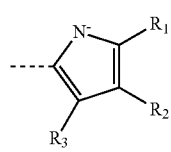 (XXA-5)
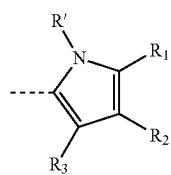 (XXA-6)
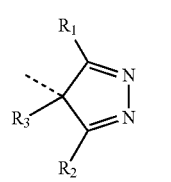 (XXB-1)
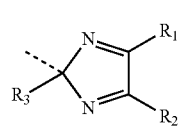 (XXB-2)
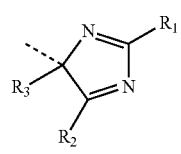 (XXB-3)
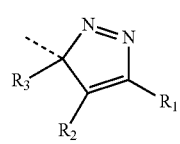 (XXB-4)
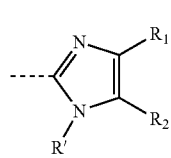 (XXB-5)
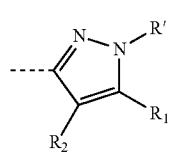 (XXB-6)
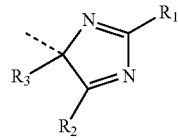 (XXB-7)
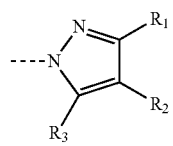 (XXB-8)
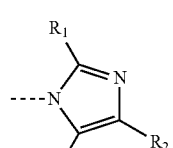 (XXB-9)
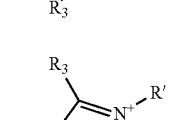 (XXB-10)
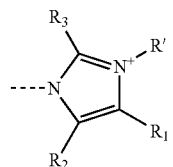 (XXB-11)
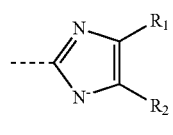 (XXB-12)
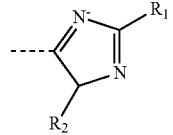 (XXB-13)
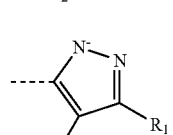 (XXB-14)
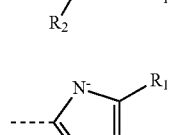 (XXB-15)
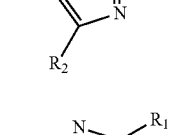 (XXB-16)

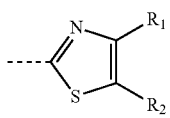 (XXB-17)
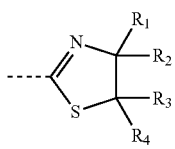 (XXB-18)
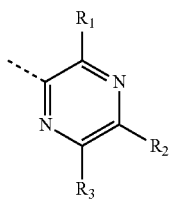 (XXB-21)
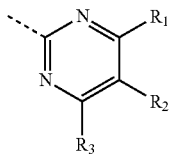 (XXB-22)
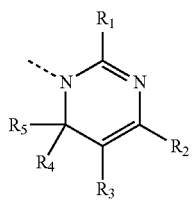 (XXB-23)
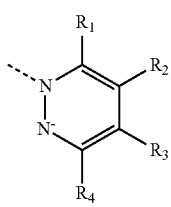 (XXB-24)
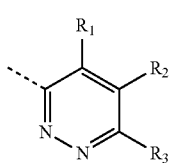 (XXB-25)
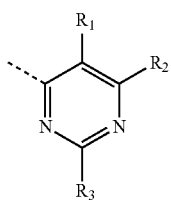 (XXB-26)
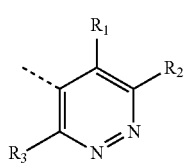 (XXB-27)
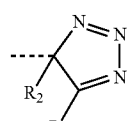 (XXC-1)
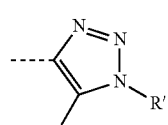 (XXC-2)
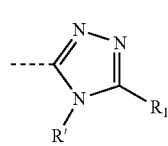 (XXC-3)
(XXC-4)
(XXC-5)
(XXC-6)
(XXC-7)
(XXC-8)
(XXC-9)
(XXC-10)

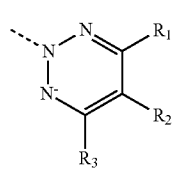 (XXC-11)
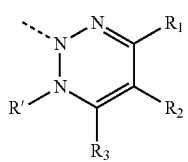 (XXC-12)
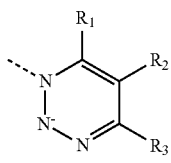 (XXC-13)
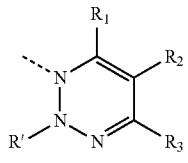 (XXC-14)
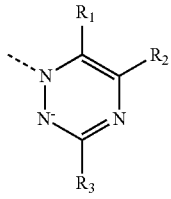 (XXC-15)
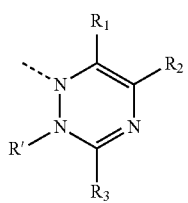 (XXC-16)
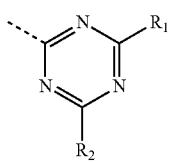 (XXC-17)
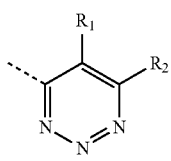 (XXC-18)
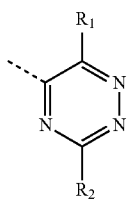 (XXC-19)
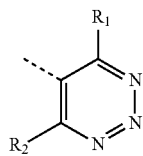 (XXC-20)
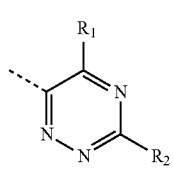 (XXC-21)
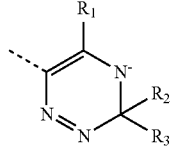 (XXC-22)
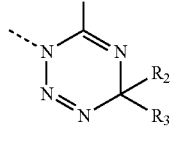 (XXC-23)
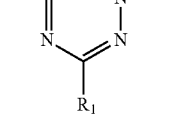 (XXC-24)
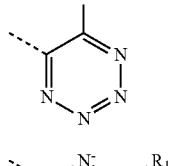 (XXC-25)
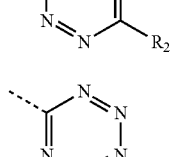 (XXC-26)
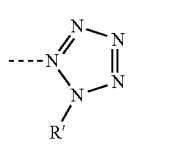 (XXC-27)
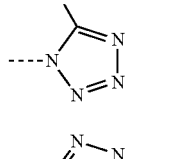 (XXD-1)
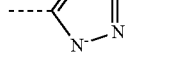 (XXD-2)
(XXD-3)

-continued
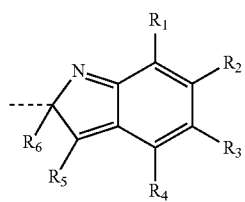
(XXE-1)
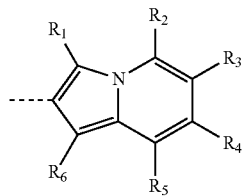
(XXE-2)
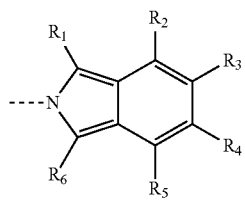
(XXE-3)
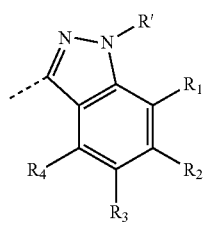
(XXF-1)
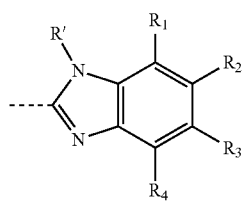
(XXF-2)
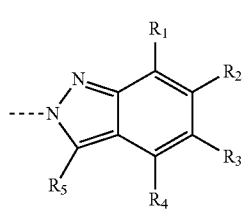
(XXF-3)
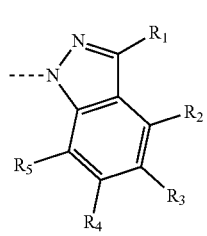
(XXF-4)
-continued
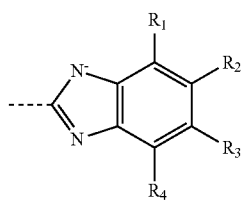
(XXF-5)
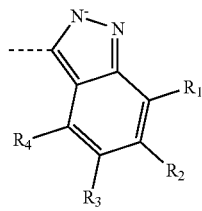
(XXF-6)
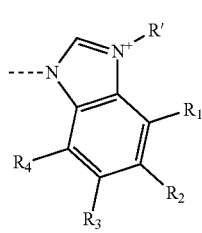
(XXF-7)
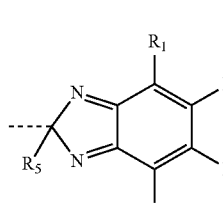
(XXF-8)
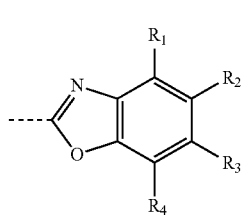
(XXF-9)
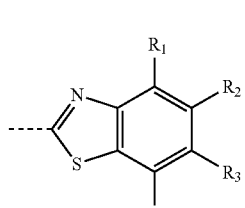
(XXF-10)
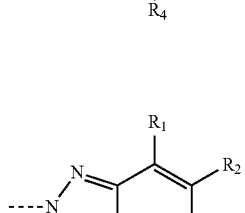
(XXG-1)

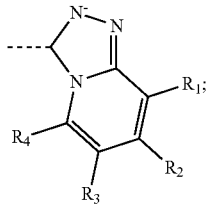
(XXG-2)

wherein:
the dotted line represents the bond connecting the substituent of (XXA-1) to (XXG-2) on the ligand La according to any one of formulae (XX-1)-(XX-5) and (XX-8)-(XX-69); and, $R_1$, $R_2$, $R_3$, $R_4$, $R_5$, and $R_6$ of moieties (XXA-1) to (XXG-2) are independently selected from H, halogen, Cl$^-$, Br$^-$, I$^-$, —NO$_2$, —OH, —NH$_2$, —COOH, —CN, —OCN$^-$, isocyanate group, sulfonyl group and substituents comprising 1 to 40 carbons and 0 to 20 heteroatoms and/or groups selected from —O—, —C(O)—, —C(O)O—, —S—, —S(O)—, SO$_2$—, —S(O)$_2$O—, —N=, —P=, —NR$^{13}$—, —PR$^{13}$—, —P(O)(OR$^{13}$)—, —P(O)(OR$^{13}$)O—, —P(O)(NR$^{13}$R$^{13}$)—, —P(O)(NR$^{13}$R$^{13}$)O—, —P(O)(NR$^{13}$R$^{13}$)NR$^{13}$—, —S(O)NR$^{13}$—, and —S(O)$_2$NR$^{13}$, with R$^{13}$ being independently selected from H, C1-C6 alkyl, C4-C20 aryl group, C4-C20 arylalkyl group and C4-C20 heteroaryl group, said alkyl, arylalkyl and heteroaryl groups being optionally perfluorinated.

12. The electrochemical and/or optoelectronic device according to claim 10 further comprising an organic-inorganic perovskite as light absorber under the form of a layer.

13. The electrochemical and/or optoelectronic device according to claim 10, wherein the complex of formula (XX) is under cationic form and provided with an anionic species independently selected from ClO$_4^-$, PF$_6^-$, BF$_4^-$, [B(CN)$_4$]$^-$, CF3SO$_3^-$, [(CF$_3$SO$_2$)$_2$N]$^-$ (TFSI), [B(C$_6$H$_3$(m-CF$_3$)$_2$)$_4$]$^-$, [B(C$_6$F$_5$)$_4$]$^-$, [B(C$_6$H$_5$)$_4$]$^-$, [Al(OC(CF$_3$)$_3$)$_4$]$^-$, or [CB$_{11}$H$_{12}$]$^-$.

14. The electrochemical and/or optoelectronic device according to claim 10, wherein M of the complex of formula (XX) is Cu$^{2+}$.

15. The electrochemical and/or optoelectronic device according to claim 10, wherein n of the complex of formula (XX) of the p-dopant is 2, 3 or 4.

16. The electrochemical and/or optoelectronic device according to claim 10, wherein n of the complex of formula (XX) is 2, 3 or 4.

17. The electrochemical and/or optoelectronic device according to claim 10, wherein m of the complex of formula (XX) is 0.

18. The electrochemical and/or optoelectronic device according to claim 10, wherein La of the complex of formula (XX) is a ligand selected from a moiety according to any one of formulae (XX-1)-(XX-5) and (XX-66) to (XX-69).

19. The electrochemical and/or optoelectronic device according to claim 10, wherein, provided that m is 0, the complex of formula (XX) is selected from a complex according to any one of formulae (XXIII) to (XXV)

M L1 L2 L3 L4         (XXIII), wherein L1, L2, L3 and L4 are selected from monodentate ligands,

M L1 L2 L3         (XXIV), wherein L1 and L2 are selected from monodentate ligands and L3 is selected from bidentate ligands,

M L1 L2         (XXV), wherein L1 and L2 are selected from bidentate ligands, or L1 is selected from monodentate ligands and L2 is selected from tridentate ligands;
wherein said mono-, bi-, or tridentate ligands are independently selected from La ligand.

\* \* \* \* \*

UNITED STATES PATENT AND TRADEMARK OFFICE
CERTIFICATE OF CORRECTION

PATENT NO.       : 10,038,150 B2
APPLICATION NO.  : 15/099089
DATED            : July 31, 2018
INVENTOR(S)      : Julian Burschka et al.

Page 1 of 2

It is certified that error appears in the above-identified patent and that said Letters Patent is hereby corrected as shown below:

Column 39
- Line 62: "... A, B and C; ..." to be replaced with "... A, B and C; ..."

Column 40
- Line 18: "... A. B. C and G; ..." to be replaced with "... A, B, C and G; ..."

Column 82
- Line 3: "... $Sn^2$, ..." to be replaced with "... $Sn^{2+}$, ..."

Column 82
- Line 6: "... $BF_4$, $PF_6$, ..." to be replaced with "... $BF_4^-$, $PF_6^-$, ..."

Column 85
- Line 45: "... for$C_{27}H_{27}CoN_9P2F_{12}$826.1005. ..." to be replaced with "... for $C_{27}H_{27}CoN_9P_2F_{12}$ 826.1005; ..."

Column 86
- Line 2: "... C, 40.69; H, 3.86; N, 13.56%. ..." to be replaced with "... C 40.69, H 3.86, N 13.56%. ..."

Column 86
- Line 15: "... 868.1475. ..." to be replaced with "... 868.1475; ..."

Column 86
- Lines 39 and 40: "... C, 35.18; H, 1.77; N, 8.21. found: C, 36.58; H, 1.76; N, 8.25%. ..." to be replaced with "... C 35.18, H 1.77, N 8.21; found: C 36.58, H 1.76, N 8.25%. ..."

Column 86
- Lines 60 and 61: "... C, 30.82; H, 1.55; N, 7.19. found: C, 31.04; H, 1.35; N, 7.35%. ..." to be replaced with "... C 30.82, H 1.55, N 7.19; found: C 31.04, H 1.35, N 7.35%. ..."

Signed and Sealed this
Twenty-fifth Day of September, 2018

Andrei Iancu
*Director of the United States Patent and Trademark Office*

CERTIFICATE OF CORRECTION (continued)
U.S. Pat. No. 10,038,150 B2

Column 87
- Line 4: "...20 m..." to be replaced with "... 20 µm ..."

Column 87
- Line 36: "... $2.0\times10^{+5}$ S cm$^{-1}$..." to be replaced with "... $2.0\times10^{-5}$ S cm$^{-1}$ ..."

Column 88
- Line 19: "... 25 m ..." to be replaced with "... 25 µm ..."

Column 89
- Line 11: "... (c$^=$4.01×10$^4$ ..." to be replaced with "... (ε $^=$4.01×10$^4$ ..."

Column 110
- Line 6: "... Cu'. ..." to be replaced with "... Cu$^{2+}$. ..."

Column 110
- Line 9: "... is 2, ..." to be replaced with "... is ≥ 2, ..."